United States Patent
Jung et al.

(10) Patent No.: US 9,818,952 B2
(45) Date of Patent: Nov. 14, 2017

(54) CONDENSED CYCLIC COMPOUND AND ORGANIC LIGHT EMITTING DEVICE INCLUDING THE SAME

(71) Applicant: SAMSUNG DISPLAY CO., LTD., Yongin, Gyeonggi-Do (KR)

(72) Inventors: Hye-Jin Jung, Yongin (KR); Jin-O Lim, Yongin (KR); Sang-Hyun Han, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 685 days.

(21) Appl. No.: 14/300,540

(22) Filed: Jun. 10, 2014

(65) Prior Publication Data
US 2015/0108440 A1   Apr. 23, 2015

(30) Foreign Application Priority Data
Oct. 22, 2013   (KR) .................. 10-2013-0126105

(51) Int. Cl.
| | | |
|---|---|---|
| H01L 51/00 | (2006.01) | |
| H01L 51/50 | (2006.01) | |
| C09K 11/06 | (2006.01) | |
| C07D 493/06 | (2006.01) | |

(52) U.S. Cl.
CPC .......... *H01L 51/006* (2013.01); *C07D 493/06* (2013.01); *C09K 11/06* (2013.01); *H01L 51/0061* (2013.01); *H01L 51/0073* (2013.01); *H01L 51/0081* (2013.01); *H01L 51/5012* (2013.01); *H01L 51/5056* (2013.01); *H01L 51/5072* (2013.01)

(58) Field of Classification Search
CPC ..... C07D 493/06; C09K 11/06; H01L 51/006; H01L 51/0061; H01L 51/0073; H01L 51/0081; H01L 51/5012; H01L 51/5056; H01L 51/5072
See application file for complete search history.

(56) References Cited

U.S. PATENT DOCUMENTS

| | | | |
|---|---|---|---|
| 7,053,255 B2 | 5/2006 | Ikeda et al. | |
| 7,233,019 B2 | 6/2007 | Ionkin et al. | |
| 2004/0185300 A1* | 9/2004 | Hatwar | ............... H01L 51/5064 |
| | | | 428/690 |
| 2005/0156164 A1 | 7/2005 | Sotoyama | |
| 2005/0221124 A1* | 10/2005 | Hwang | ................. C07F 9/5728 |
| | | | 428/690 |
| 2008/0193797 A1 | 8/2008 | Heil et al. | |
| 2010/0013381 A1 | 1/2010 | Stoessel et al. | |
| 2010/0032658 A1 | 2/2010 | Lee et al. | |
| 2011/0284831 A1* | 11/2011 | Kaiser | ................ H01L 51/0056 |
| | | | 257/40 |
| 2012/0228584 A1* | 9/2012 | Wigglesworth | ..... C07D 493/06 |
| | | | 257/40 |

FOREIGN PATENT DOCUMENTS

| | | | |
|---|---|---|---|
| CN | 103497758 A | * | 1/2014 |
| EP | 2100941 A2 | * | 12/2008 |
| JP | 2009-033067 A | | 2/2009 |
| JP | 2010-034451 A | | 2/2010 |
| JP | 2010-109360 A | * | 5/2010 |
| JP | 2013-161860 A | * | 8/2013 |
| KR | 10-2006-0006760 A | | 1/2006 |
| KR | 10-2008-0049770 A | | 6/2008 |
| KR | 10-2009-0033493 A | | 4/2009 |
| KR | 10-2010-0007780 A | | 1/2010 |
| WO | WO-2012/070226 A1 | | 5/2012 |

OTHER PUBLICATIONS

Machine translation of JP 2013-161860 A (publication date Aug. 2013).*
Machine translation of JP 2010-109360 A (publication date May 2010).*
Machine translation of CN 103497758 A (publication date Jan. 2014).*

* cited by examiner

*Primary Examiner* — Dawn Garrett
(74) *Attorney, Agent, or Firm* — Lee & Morse, P.C.

(57) ABSTRACT

A condensed cyclic compound and an organic light-emitting device, the compound being represented by Formula 1:

<Formula 1>

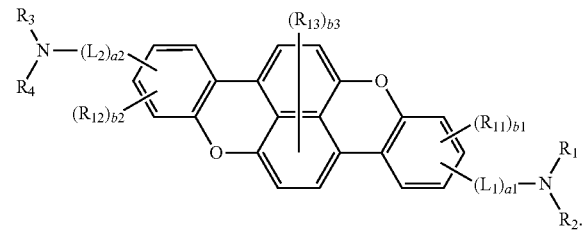

20 Claims, 1 Drawing Sheet

10

| 190 |
| 150 |
| 110 |

CONDENSED CYCLIC COMPOUND AND ORGANIC LIGHT EMITTING DEVICE INCLUDING THE SAME

CROSS-REFERENCE TO RELATED APPLICATION

Korean Patent Application No. 10-2013-0126105, filed on Oct. 22, 2013, in the Korean Intellectual Property Office, and entitled: "Condensed Cyclic Compound And Organic Light Emitting Device Comprising The Same," is incorporated by reference herein in its entirety.

BACKGROUND

1. Field

Embodiments relate to a condensed cyclic compound and an organic light-emitting device including the same.

2. Description of the Related Art

Organic light-emitting devices (OLEDs), which are self-emitting devices, may have advantages such as wide viewing angles, excellent contrast, quick response, high brightness, excellent driving voltage characteristics, and may provide multicolored images.

An organic light-emitting device may have a structure in which a first electrode, a hole transport region, an emission layer, an electron transport region, and a second electrode are sequentially disposed in this order on a substrate. Holes injected from the first electrode may move to the emission layer via the hole transport region, while electrons injected from the second electrode may move to the emission layer via the electron transport region. Carriers, such as the holes and electrons, may recombine in the emission layer to generate exitons. When the exitons drop from an excited state to a ground state, light is emitted.

SUMMARY

Embodiments are directed to a condensed cyclic compound and an organic light-emitting device including the same.

According to one or more embodiments, there is provided a condensed cyclic compound represented by Formula 1:

<Formula 1>

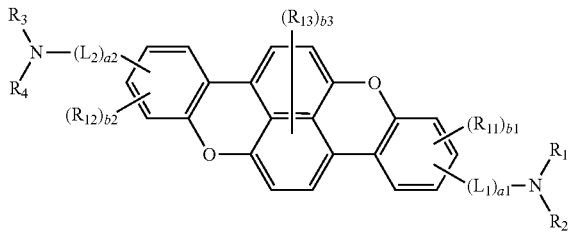

wherein, in Formula 1, $L_1$ and $L_2$ are each independently a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, or a substituted or unsubstituted divalent non-aromatic hetero-condensed polycyclic group, a1 and a2 are each independently an integer of 0 to 5, $R_1$ to $R_4$ are each independently a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group, or a substituted or unsubstituted monovalent non-aromatic hetero-condensed polycyclic group.

$R_{11}$ to $R_{13}$ are each independently a hydrogen, a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cyclo alkyl group, a substituted or unsubstituted $C_2$-$C_{10}$ heterocyclo alkyl group, a substituted or unsubstituted $C_3$-$C_{10}$ cyclo alkenyl group, a substituted or unsubstituted $C_2$-$C_{10}$ heterocyclo alkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic hetero-condensed polycyclic group, —S($Q_1$)($Q_2$)($Q_3$), or —B($Q_4$)($Q_5$), b1 and b2 are each independently an integer of 1 to 3, and b3 is an integer of 1 to 4, wherein at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, the substituted monovalent non-aromatic hetero-condensed polycyclic group, the substituted $C_2$-$C_{60}$ alkynyl group, and the substituted $C_1$-$C_{60}$ alkoxy group is a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_3$-$C_{60}$ alkynyl group, or a $C_1$-$C_{60}$ alkoxy group, each substituted with at least one of a deuterium —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_3$-$C_{10}$ cyclo alkyl group, a $C_2$-$C_{10}$ heterocyclo alkyl group, a $C_3$-$C_{10}$ cyclo alkenyl group, a $C_2$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —N($Q_{13}$)($Q_{12}$), —Si($Q_{13}$)($Q_{14}$)($Q_{15}$), and —B($Q_{16}$)($Q_{17}$);

a $C_3$-$C_{10}$ cyclo alkyl group, a $C_2$-$C_{10}$ heterocyclo alkyl group, a $C_3$-$C_{10}$ cyclo alkenyl group, a $C_2$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic hetero-condensed polycyclic group;

a $C_3$-$C_{10}$ cyclo alkyl condensed, a $C_2$-$C_{10}$ heterocyclo alkyl group, a $C_3$-$C_{10}$ cyclo alkenyl group, a $C_2$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic hetero-condensed polycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cyclo alkyl group, a $C_2$-$C_{10}$ heterocyclo alkyl group, a $C_3$-$C_{10}$ cyclo alkenyl group, a $C_2$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —N($Q_{21}$)($Q_{22}$), —Si($Q_{23}$)($Q_{24}$)($Q_{25}$), and —B($Q_{26}$)($Q_{27}$); or —Si($Q_{31}$)($Q_{32}$)($Q_{33}$), or —B($Q_{34}$)($Q_{35}$), wherein $Q_1$ to $Q_5$, $Q_{11}$ to $Q_{17}$, $Q_{21}$ to $Q_{27}$, and $Q_{31}$ to $Q_{35}$ are each independently a hydrogen, a $C_1$-$C_{60}$ alkyl group, a $C_2$-$C_{60}$ alkynyl group, a $C_1$-$C_{60}$ alkoxy group, a $C_3$-$C_{10}$ cyclo alkyl group, a $C_2$-$C_{10}$ heterocyclo alkyl group, a $C_3$-$C_{10}$ cyclo alkenyl group, a $C_2$-$C_{10}$ heterocyclo alkenyl group, a $C_6$-$C_{60}$ aryl group, a $C_2$-$C_{60}$ heteroaryl group, a monovalent non-aromatic condensed polycyclic group, or a monovalent non-aromatic hetero-condensed polycyclic group.

According to one or more embodiments, an organic light-emitting device includes: a first electrode; a second electrode disposed opposite to the first electrode; and an organic layer disposed between the first electrode and the second electrode and including an emission layer, wherein the organic layer includes at least one of the condensed cyclic compounds of Formula 1 above.

BRIEF DESCRIPTION OF THE DRAWING

Features will be apparent to those of skill in the art by describing in detail exemplary embodiments with reference to the attached drawing in which:

The FIGURE illustrates a schematic view of a structure of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

According to an embodiment, there may be provided a condensed cyclic compound represented by Formula 1.

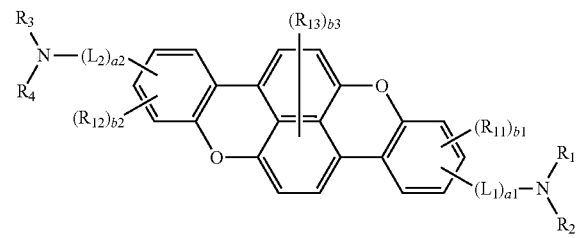

<Formula 1>

In formula 1, $L_1$ and $L_2$ may be each independently:

a phenylene group, a pentalenylene group, an indeylene group, a naphthylene group, an azulenylene group, a heptalenylene group, an indazenylene group, an acenaphthylene group, a fluorenylene group, a spiro-fluorenylene group, a benzofluorenylene group, a dibenzofluorenylene group, a phentalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, an imidazolylene group, a pyrazolylene group, a thiazolylene group, an isothiazolylene group, a oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, a oxadiazolylene group, a triazinylene group, a dibenzofuranylene group, a dibenzothiophenylene group, a benzocarbazolylene group, or a dibenzocarbazolylene group; or a phenylene group, a pentalenylene group, an indeylene group, a naphthylene group, an azulenylene group, a heptalenylene group, an indazenylene group, an acenaphthylene group, a fluorenylene group, a spiro-fluorenylene group, a benzofluorenylene group, a dibenzofluorenylene group, a phenalenylene group, a phenanthrenylene group, an anthrazenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, an imidazolylene group, a pyrazolylene group, a thiazolylene group, an isothiazolylene group, a oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, a oxadiazolylene group, a triazinylene group, a dibenzofuranylene group, a dibenzothiophenylene group, a benzocarbazolylene group, or a dibenzocarbazolylene, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, an a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and $Si(Q_{31})(Q_{32})(Q_{33})$ (where $Q_{31}$ to $Q_{33}$ are each independently a hydrogen, a $C_1$-$C_{10}$ alkyl group, a $C_1$-$C_{10}$ alkoxy group, a phenyl group, or a naphthyl group).

For example, L1 and L2 in Formula 1 may be each independently represented by one of Formulae 3-1 to 3-32.

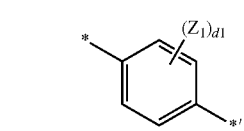

Formula 3-1

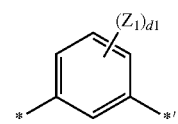

Formula 3-2

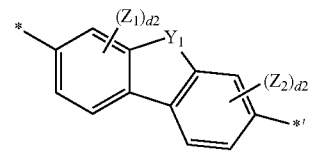

Formula 3-3

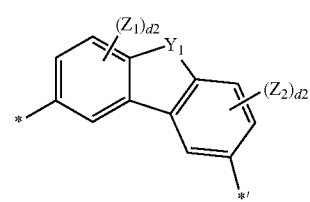

Formula 3-4

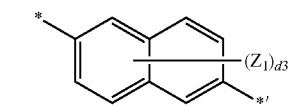

Formula 3-5

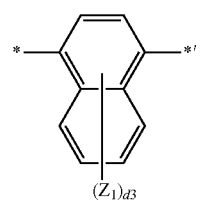

Formula 3-6

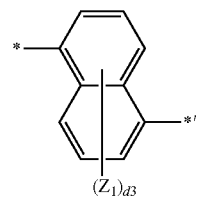

Formula 3-7

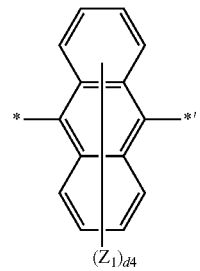

Formula 3-8

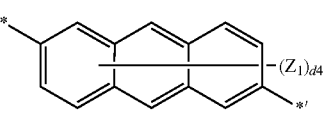

Formula 3-9

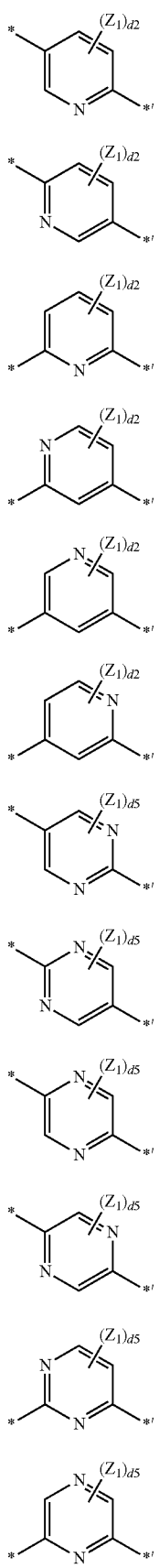
Formula 3-10
Formula 3-11
Formula 3-12
Formula 3-13
Formula 3-14
Formula 3-15
Formula 3-16
Formula 3-17
Formula 3-18
Formula 3-19
Formula 3-20
Formula 3-21
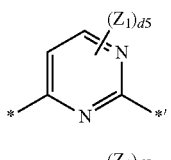
Formula 3-22
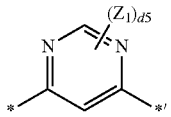
Formula 3-23
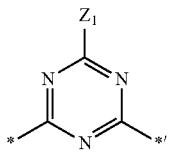
Formula 3-24
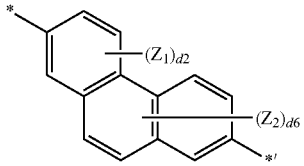
Formula 3-25
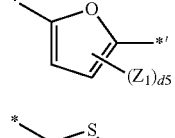
Formula 3-26
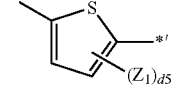
Formula 3-27
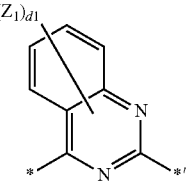
Formula 3-28
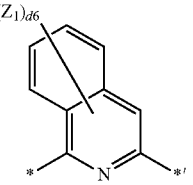
Formula 3-29
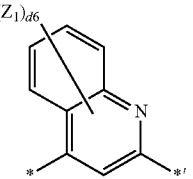
Formula 3-30
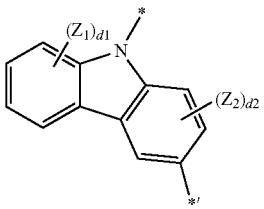
Formula 3-31

Formula 3-32

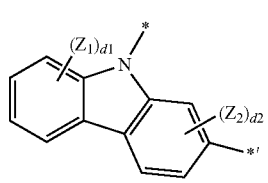

In formulae 3-1 to 3-32, $Z_1$ and $Z_2$ may be each independently a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, a dibenzocarbazolyl group, or —Si($Q_{31}$)($Q_{32}$)($Q_{33}$) (where $Q_{31}$ to $Q_{33}$ may be each independently, a hydrogen, a $C_1$-$C_{10}$ alkyl group, a $C_1$-$C_{10}$ alkoxy group, a phenyl group, or a naphthyl group;

d1 may be an integer of 1 to 4;

d2 may be an integer of 1 to 3;

d3 may be an integer of 1 to 6:

d4 may be an integer of 1 to 8;

d5 may be 1 or 2; and d6 may be an integer of 1 to 5.

In Formulae 3-1 to 3-32, * and *' are binding sites. For example, * may be a binding site to a core, $L_1$, or $L_2$ in Formula 1, and *' may be a binding site to $L_1$, $L_2$, or N in Formula 1.

For example, $L_1$ and $L_2$ in Formula 1 may be each independently represented by one of Formulae Formula 4-1 to 4-23:

Formula 4-1

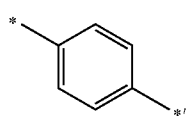

Formula 4-2

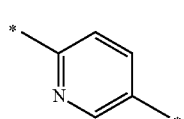

Formula 4-3

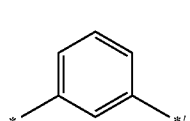

Formula 4-4

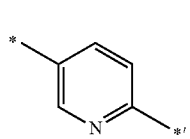

Formula 4-5

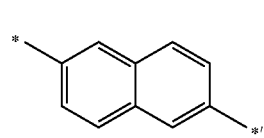

Formula 4-6

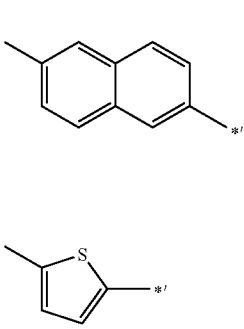

Formula 4-7

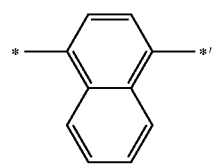

Formula 4-8

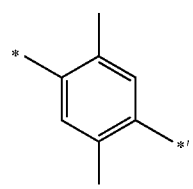

Formula 4-9

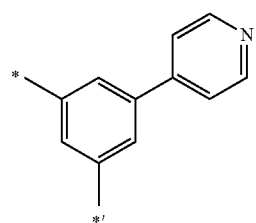

Formula 4-10

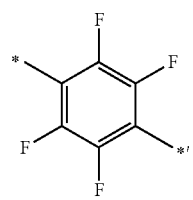

Formula 4-11

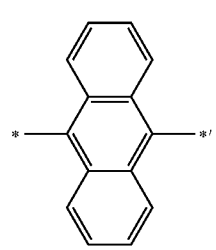

Formula 4-12

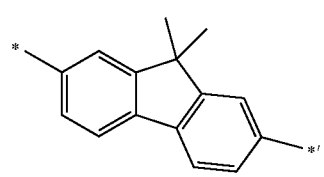

-continued

Formula 4-13
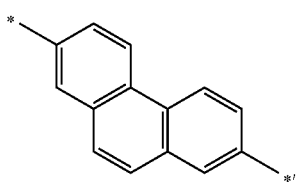

Formula 4-14
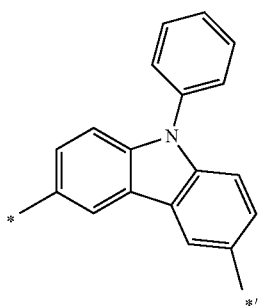

Formula 4-15
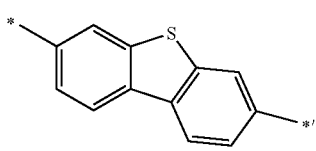

Formula 4-16
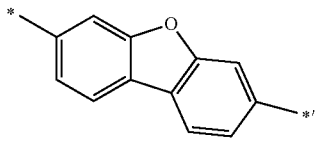

Formula 4-17
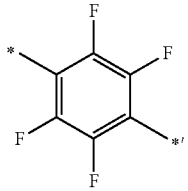

Formula 4-18
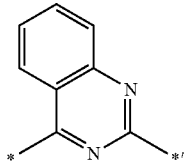

Formula 4-19
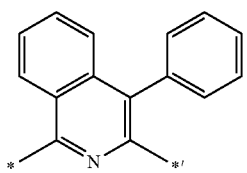

Formula 4-20
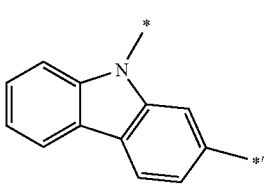

-continued

Formula 4-21
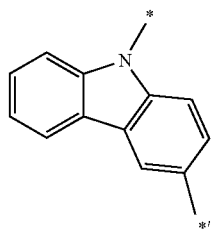

Formula 4-22
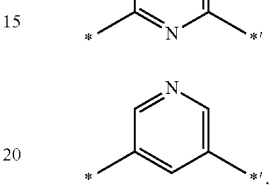

Formula 4-23

In Formula 1, a1, which indicates the number of $L_1$s, may be an integer of 0 to 5, e.g., may be 0, 1, or 2. When a1 is 0, $L_1$ may be a single bond. When a1 is 2 or greater, a plurality of $L_1$s may be identical to or different from each other.

In Formula 1, a2, which indicates the number of $L_2$s, may be an integer of 0 to 5, e.g., may be 0, 1, or 2. When a2 is 0, $L_2$ may be a single bond. When a2 is 2 or greater, a plurality of $L_2$s may be identical to or different from each other.

In Formula 1, $R_1$ to $R_4$ may be each independently:

a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group; or a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, or a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and $Si(Q_{31})(Q_{32})(Q_{33})$ (where $Q_{31}$ to $Q_{33}$ are each independently a hydrogen, a $C_1$-$C_{10}$ alkyl group, a $C_1$-$C_{10}$ alkoxy group, a phenyl group, or a naphthyl group).

For example, $R_1$ and $R_4$ in Formula 1 may be each independently;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, or a dibenzocarbazolyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, or a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, a dibenzocarbazolyl group, and —$Si(Q_{31})(Q_{32})(Q_{33})$ (where $Q_{31}$ to $Q_{33}$ may be each independently a hydrogen, a $C_1$-$C_{10}$ alkyl group, a $C_1$-$C_{10}$ alkoxy group, a phenyl group, or a naphthyl group).

For example, $R_1$ to $R_4$ in Formula 1 may be each independently represented by one of Formulae 5-1 to 5-14.

Formula 5-1
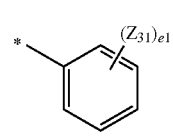

Formula 5-2
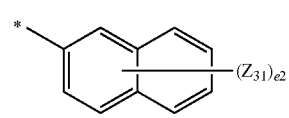

Formula 5-3
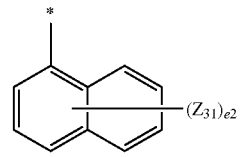

Formula 5-4
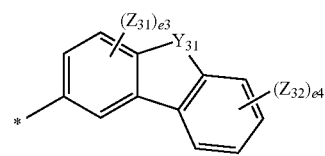

Formula 5-5
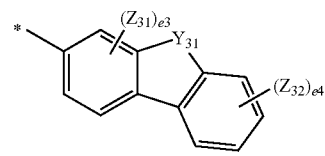

-continued

Formula 5-6
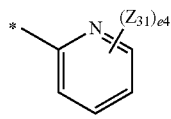

Formula 5-7
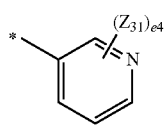

Formula 5-8
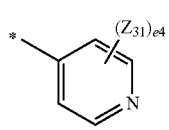

Formula 5-9
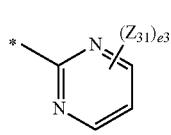

Formula 5-10
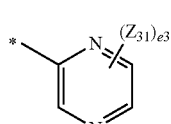

Formula 5-11
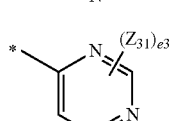

Formula 5-12
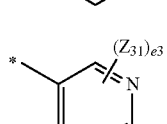

Formula 5-13
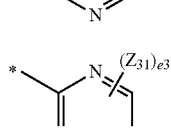

Formula 5-14
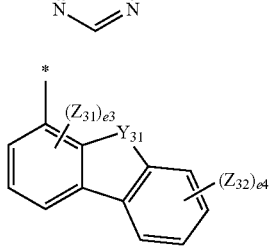

In Formulae 5-1 to 5-14, $Y_{31}$ may be O, S, $C(Z_{33})(Z_{34})$, or $N(Z_{35})$;

$Z_{31}$ to $Z_{35}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, or dibenzocarbazolyl group, or —$Si(Q_{31})(Q_{32})(Q_{33})$ (where $Q_{31}$ to $Q_{33}$ may be each independently, a hydrogen, a $C_1$-$C_{10}$ alkyl group, a $C_1$-$C_{10}$ alkoxy group, a phenyl group, or a naphthyl group);

e1 may be an integer of 1 to 5;

e2 may be an integer of 1 to 7;

e3 may be as integer of 1 to 3;

e4 may be an integer of 1 to 4;

e5 may be 1 or 2; and

* is a binding site to N in Formula 1.

In an implementation, $R_1$ to $R_4$ in Formula 1 may be each independently represented by one of Formulae 6-1 to 6-45.

Formula 6-1
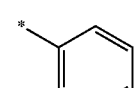

Formula 6-2
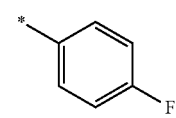

Formula 6-3
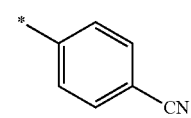

Formula 6-4
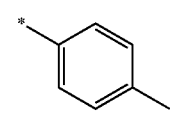

Formula 6-5
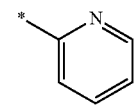

Formula 6-6
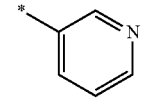

Formula 6-7
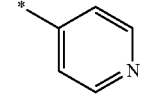

Formula 6-8
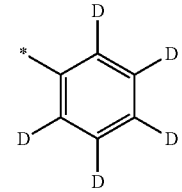

Formula 6-9
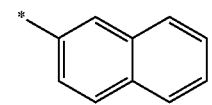

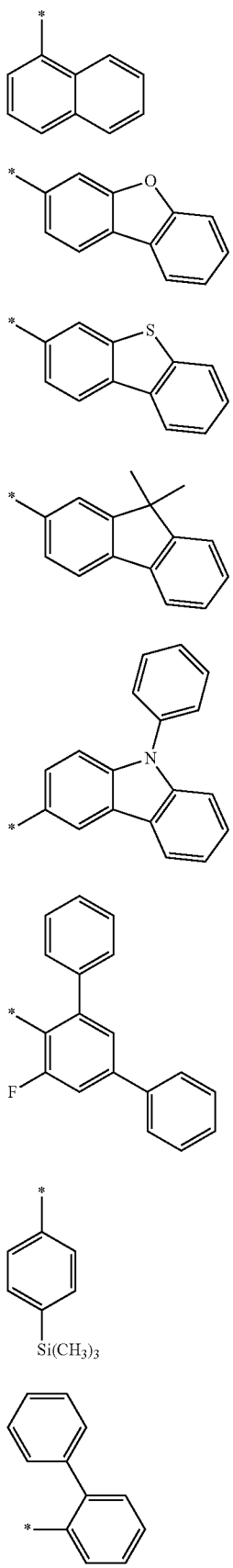
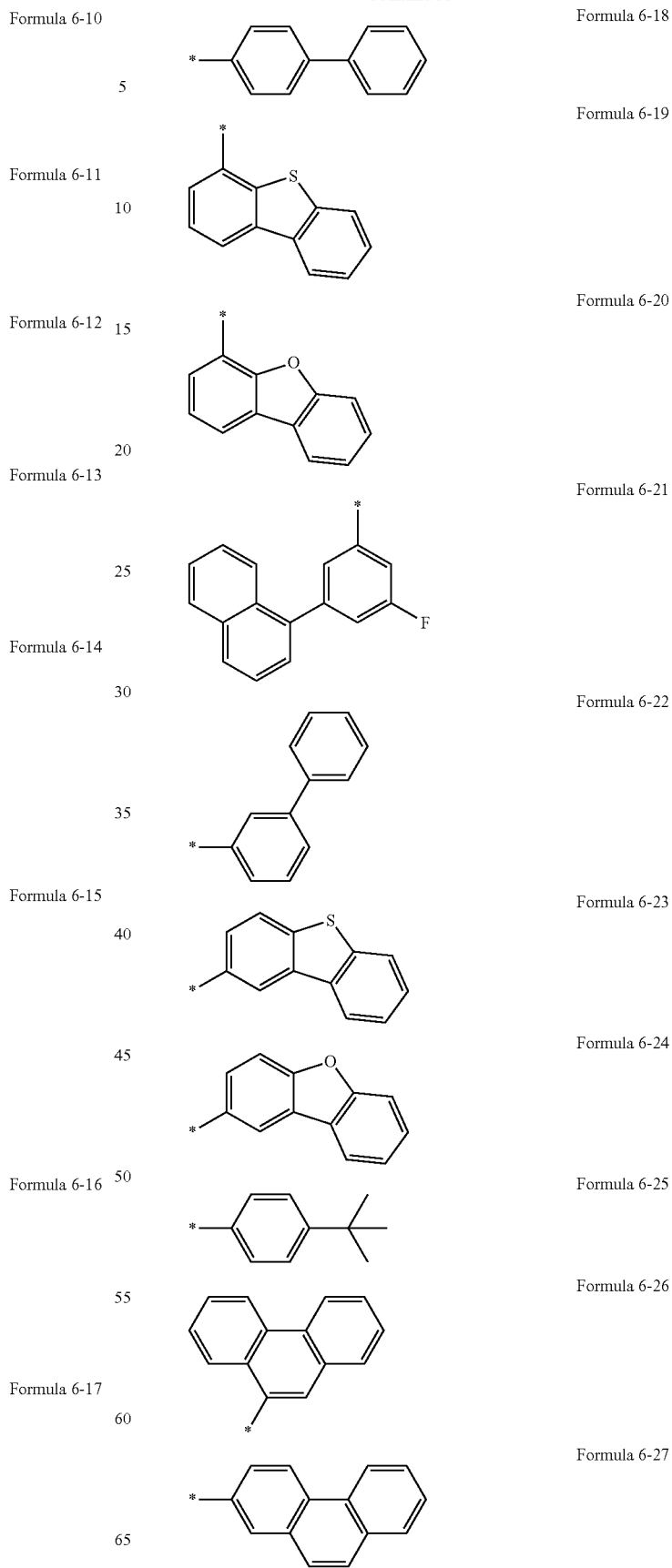

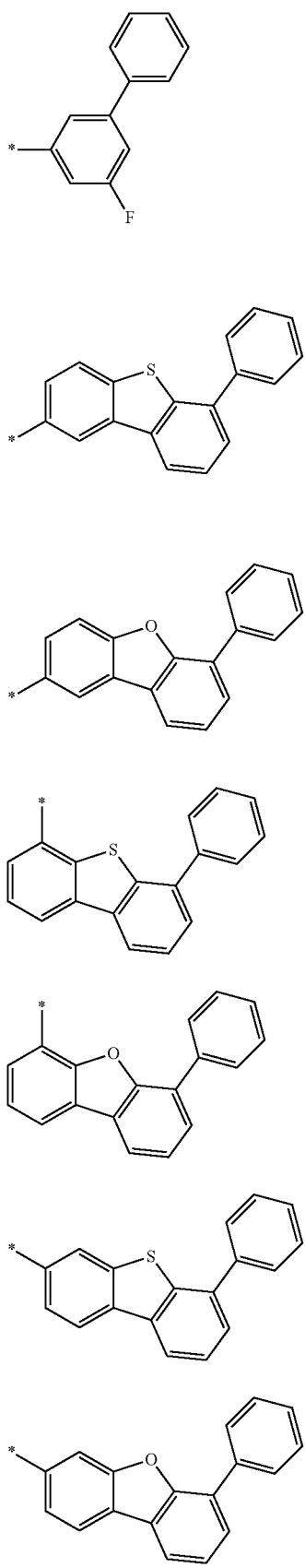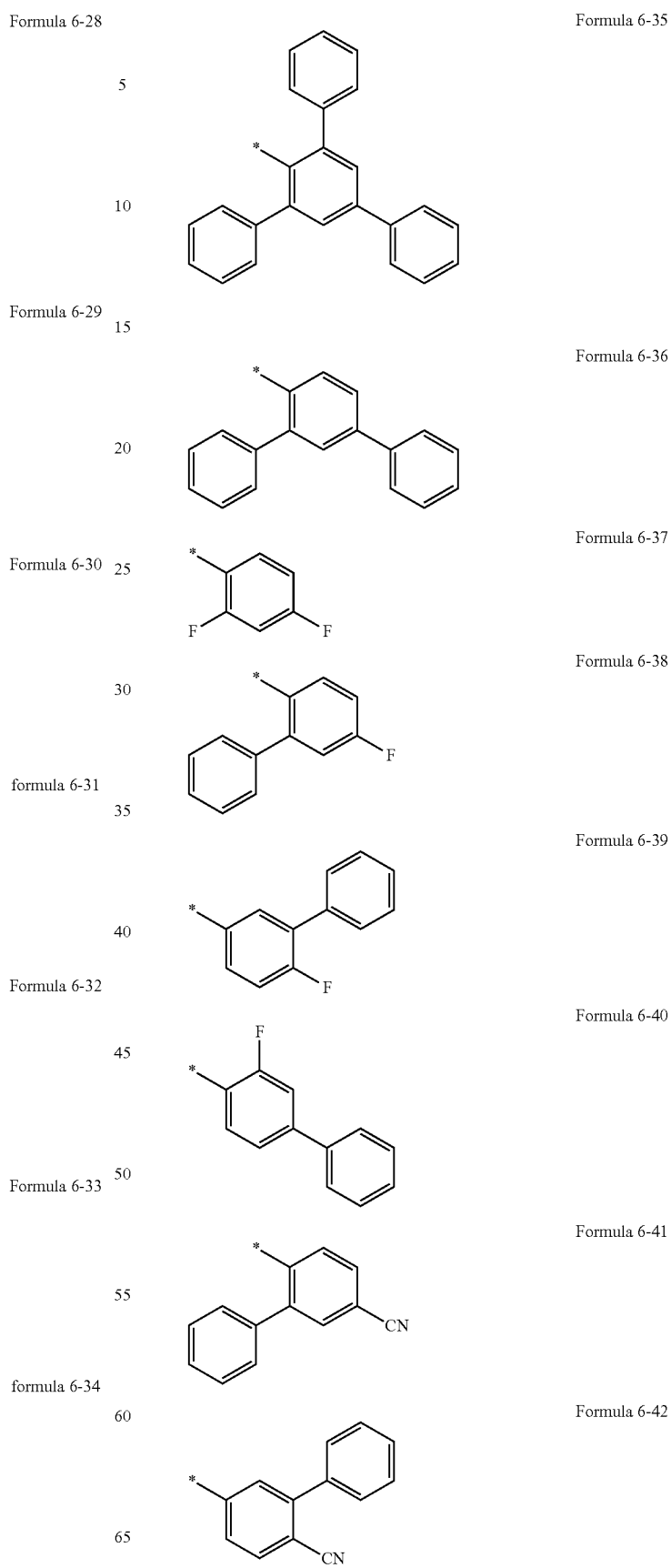

-continued

Formula 6-43

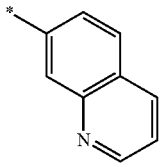

Formula 6-44

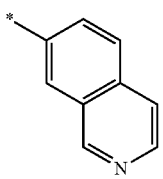

Formula 6-45

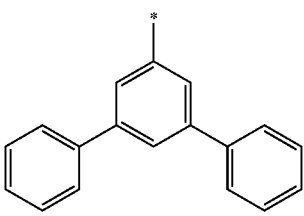

In Formula 1 above, $R_1=R_2=R_3=R_4$; $R_1=R_3$, $R_1=R_2$, and $R_2=R_4$; $R_2=R_3$, $R_1\neq R_2$, and $R_1=R_4$; $R_1=R_2$, $R_1\neq R_3$, and $R_3=R_4$; $R_2=R_3=R_4$, and $R_1\neq R_2$; $R_3=R_4$, and $R_1\neq R_2\neq R_3$; or $R_1\neq R_2\neq R_3\neq R_4$. For example, in some implementations, some of $R_1$ to $R_4$ may be the same, some of $R_1$ to $R_4$ may be different, all of $R_1$ to $R_4$ may be same, or all of $R_1$ to $R_4$ may be different.

In Formula 1, $R_{11}$ to $R_{13}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{60}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, or a dibenzocarbazolyl group, or —S($Q_1$)($Q_2$)($Q_3$), (where $Q_1$ to $Q_3$ may be each independently selected from a hydrogen, a $C_1$-$C_{10}$ alkyl group, a $C_1$-$C_{10}$ alkoxy group, a phenyl group, or naphthyl group).

In an implementation, $R_{11}$ to $R_{13}$ in Formula 1 may be each independently a hydrogen, a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, or a $C_1$-$C_{20}$ alkoxy group, but are not limited thereto.

In an implementation, $R_{11}$ to $R_{13}$ in Formula 1 may be hydrogen.

In an implementation, the condensed cyclic compound of Formula 1 may be represented by one of Formulae 1A to 1D.

<Formula 1A>

<Formula 1B>

<Formula 1C>

<Formula 1D>

Substituents in Formulae 1A to 1D may be the same as described above with respect to Formula 1.

For example, in Formulae 1A to 1D, $L_1$ and $L_2$ may be each independently represented by one of Formulae 3-1 to 3-32 above (e.g., one of Formulae 4-1 to 4-23 above);

a1 and a2 may be each independently 0, 1, or 2;

$R_1$ to $R_4$ may be each independently represented by one of Formulae 5-1 to 5-14 above (e.g., one of Formulae 6-1 to 6-45 above);

$R_{11}$ to $R_{13}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, a dibenzocarbazolyl group, or —Si($Q_1$)($Q_2$)($Q_3$) (where $Q_1$ to $Q_3$ may be each independently selected from a hydrogen, a $C_1$-$C_{10}$ alkyl group, a $C_1$-$C_{10}$ alkoxy group, a phenyl group, or a naphthyl group); and b1 to b3 may be each independently 1 or 2.

In an implementation, the condensed cyclic compound represented by Formula 1 may be represented by Formula 1A above.

In an implementation, the condensed cyclic compound represented by Formula 1 may include one of Compounds 1 to 96, below.

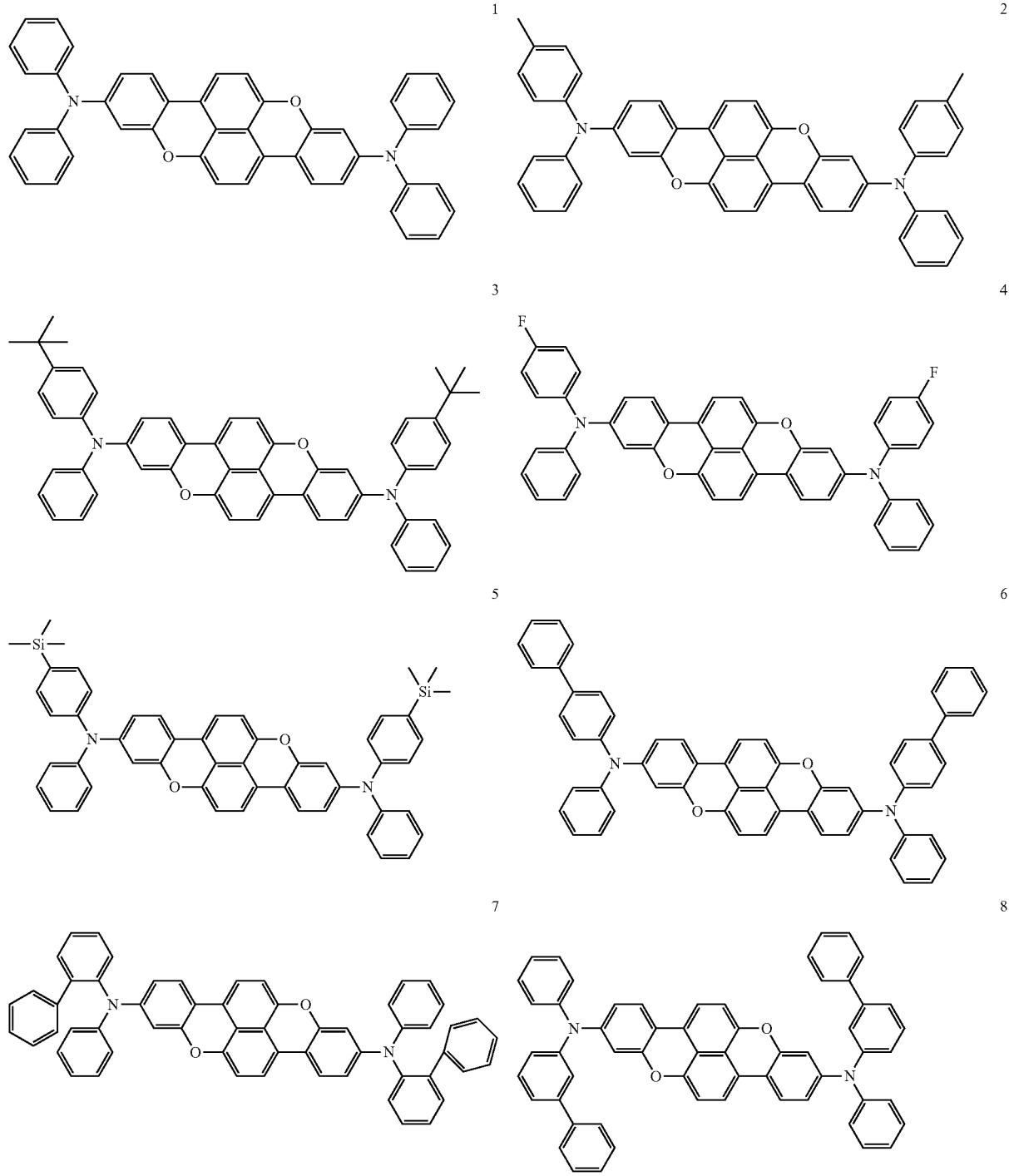

-continued
9
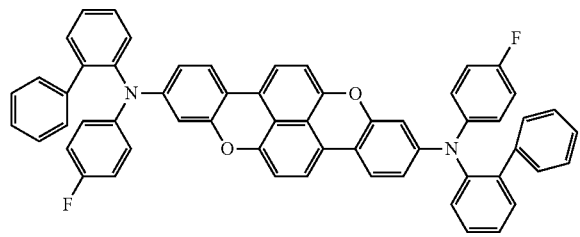
10
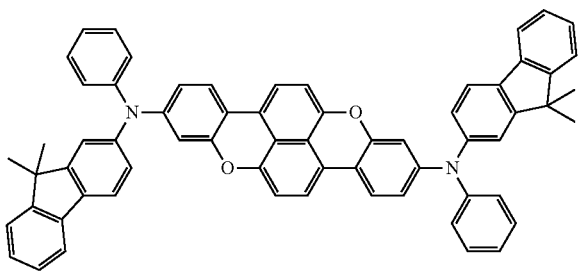
11
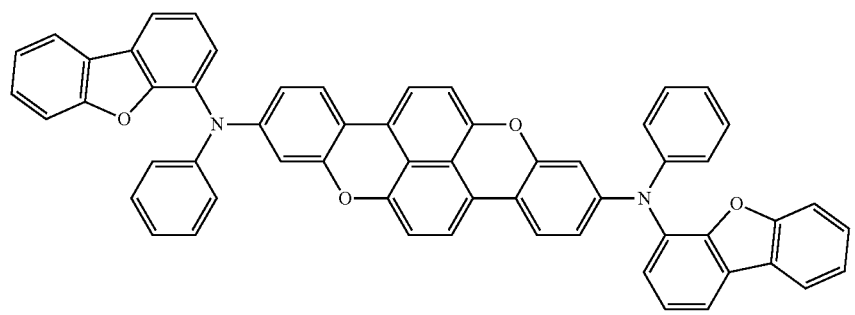
12
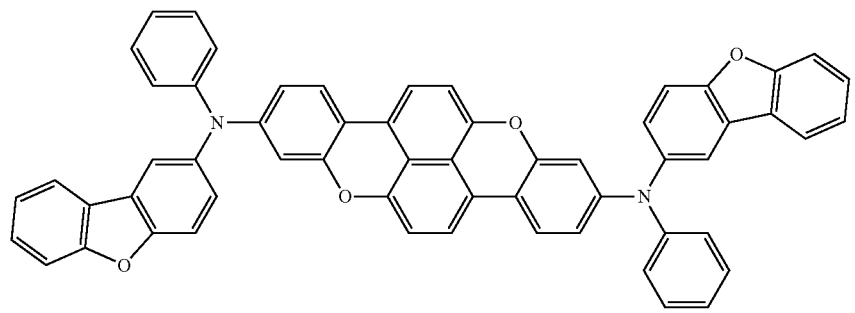
13
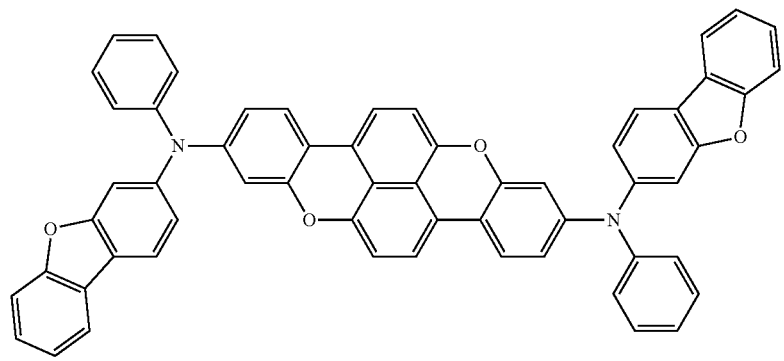
14
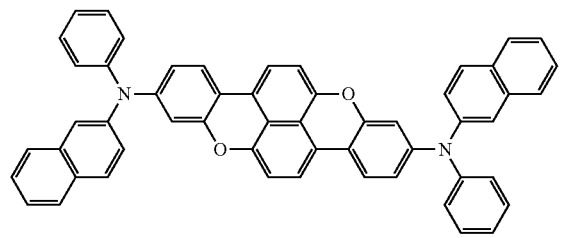
15
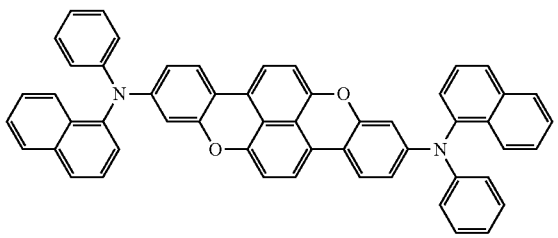

-continued
16
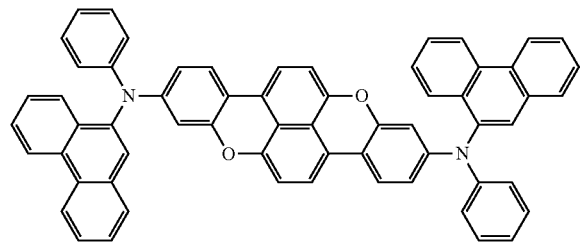
17
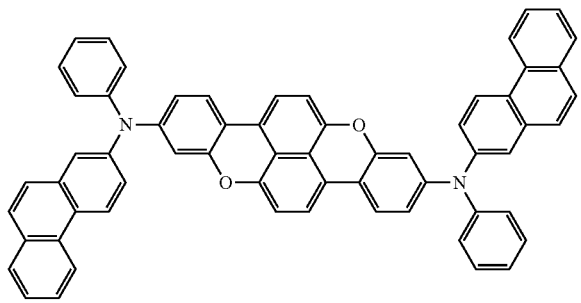
18
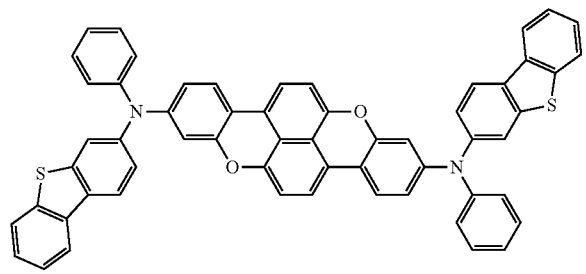
19
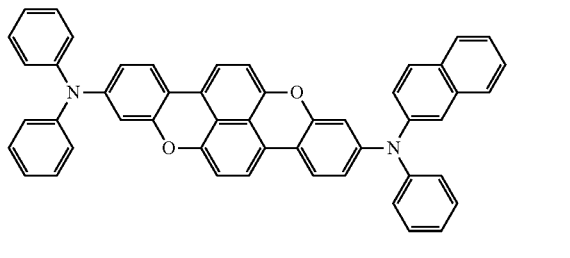
20
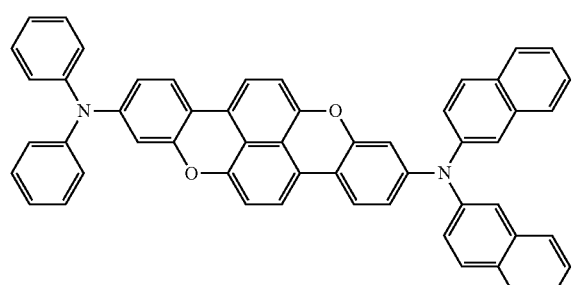
21
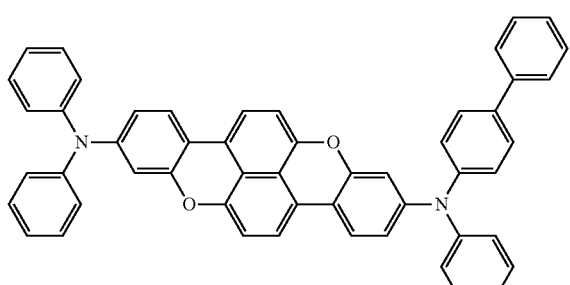
22
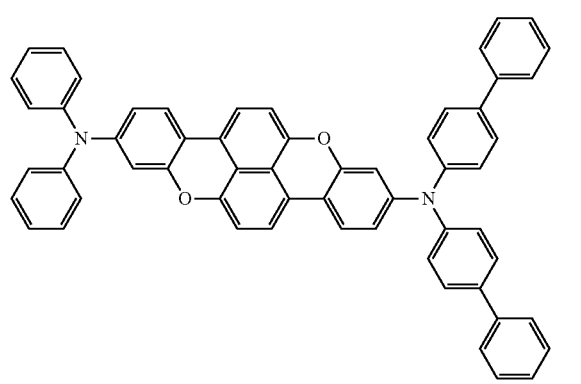
23
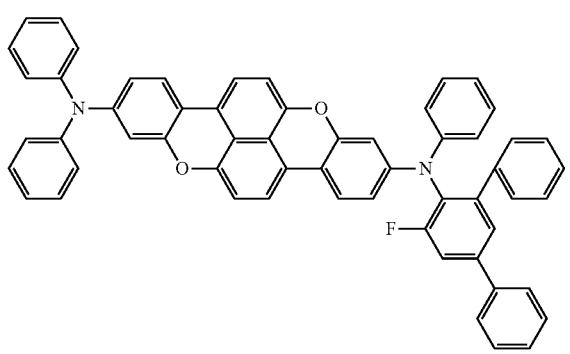
24
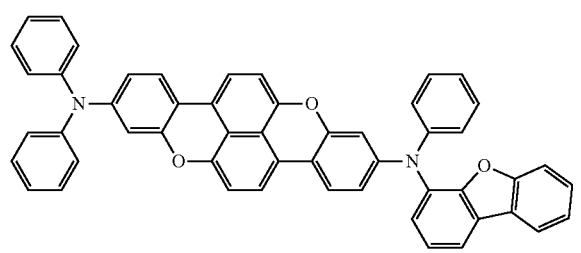
25
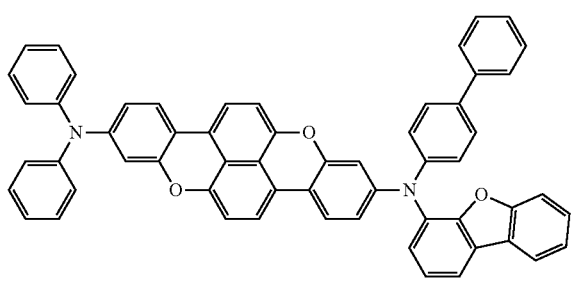

-continued
26
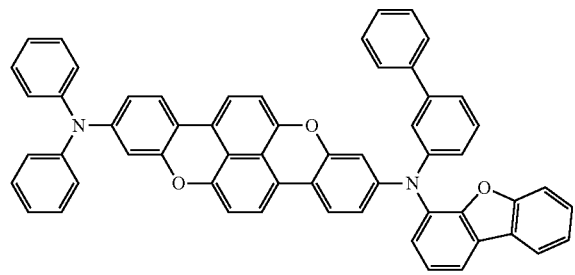
27
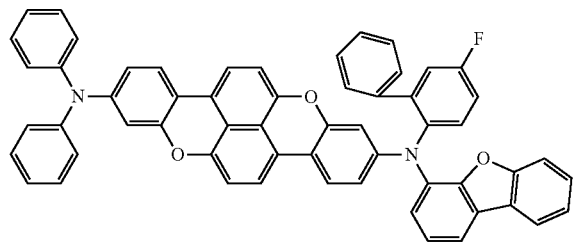
28
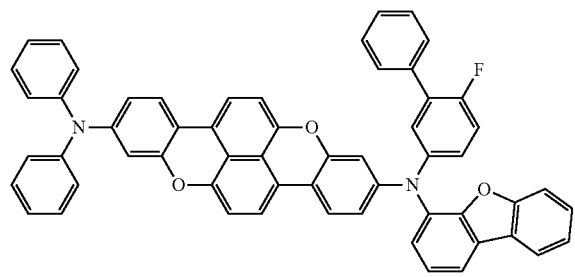
29
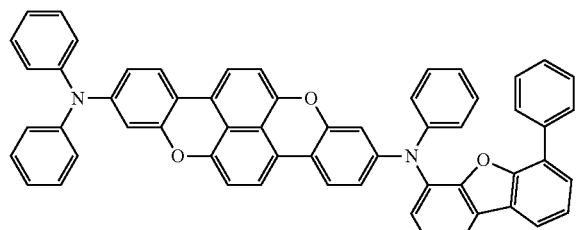
30
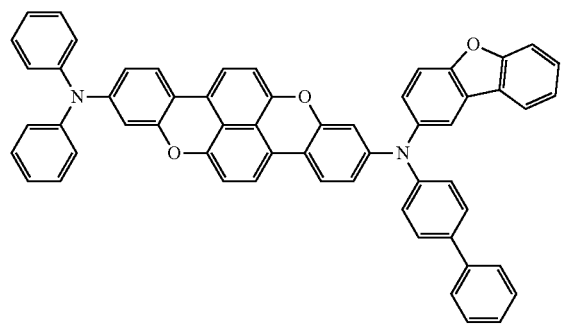
31
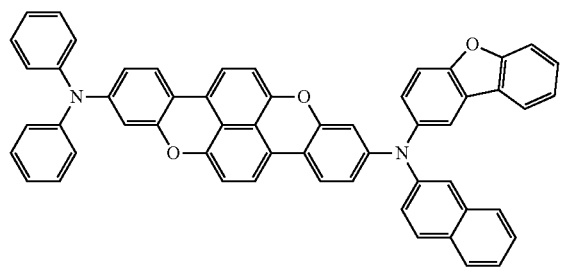
32
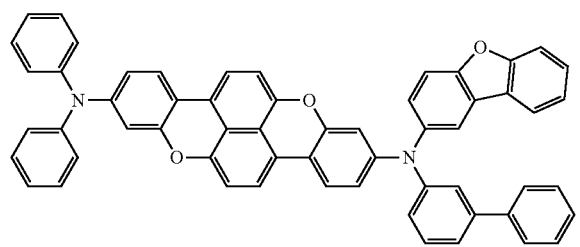
33
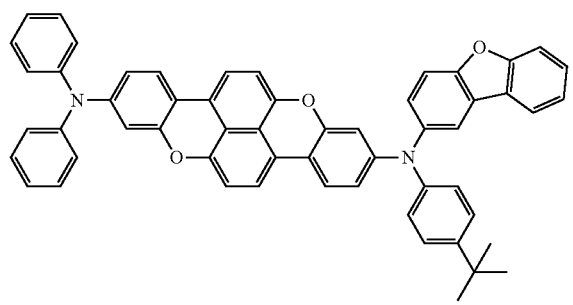
34
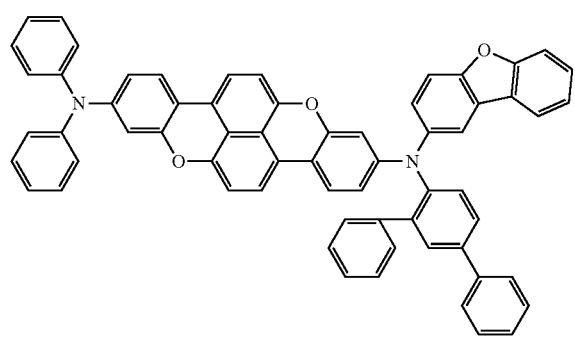
35
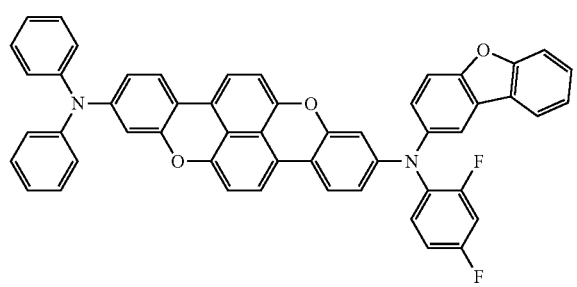

-continued
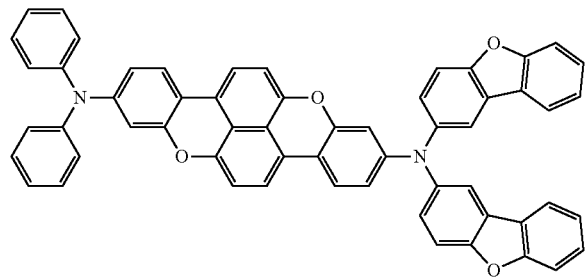
36
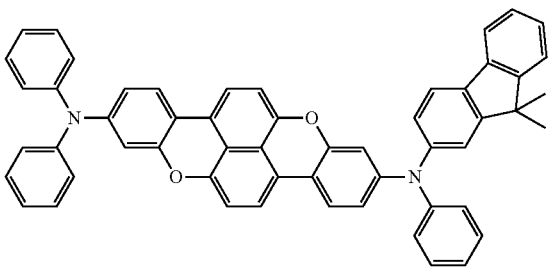
37
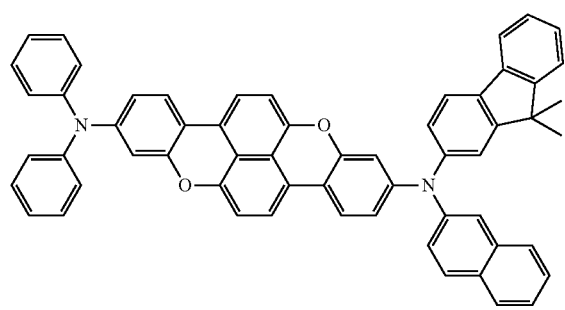
38
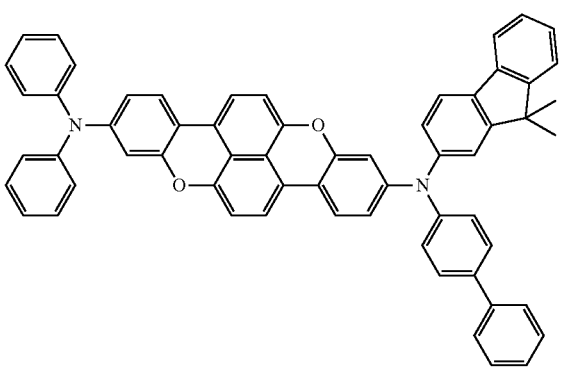
39
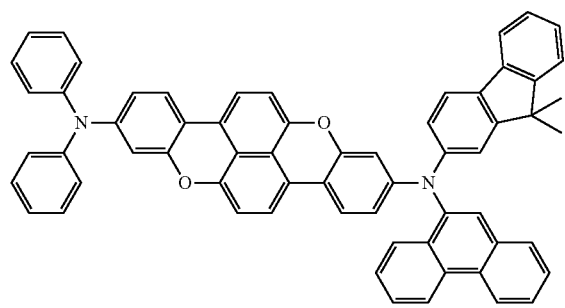
40
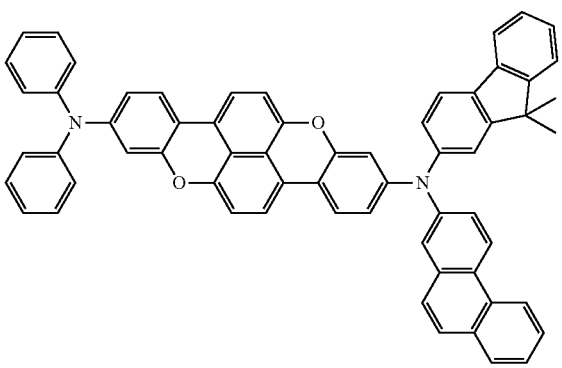
41
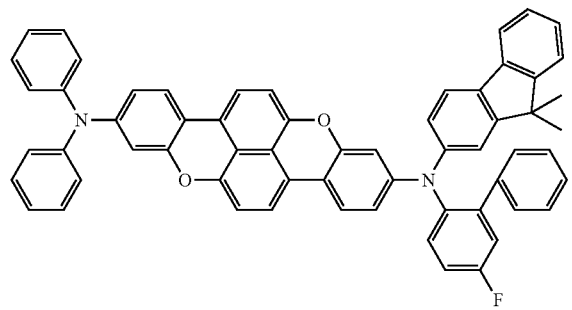
42
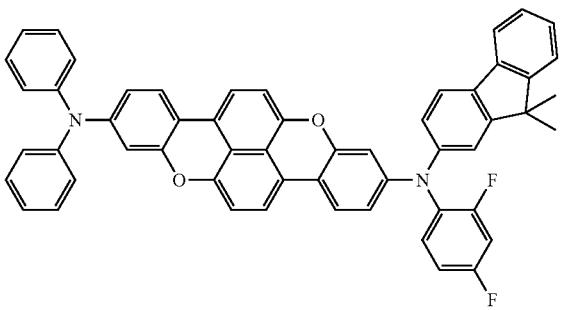
43

-continued
44
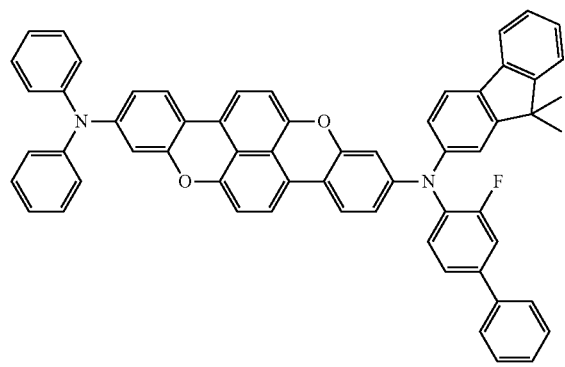
45
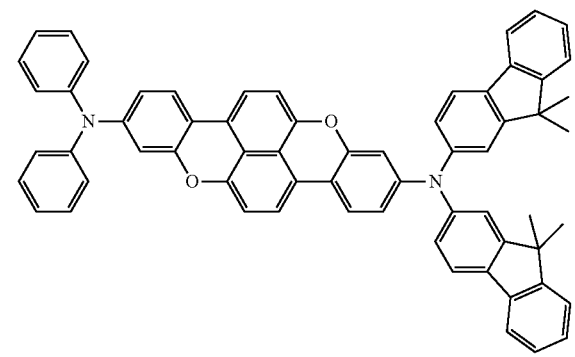
46
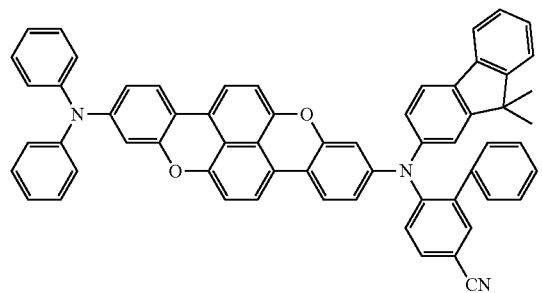
47
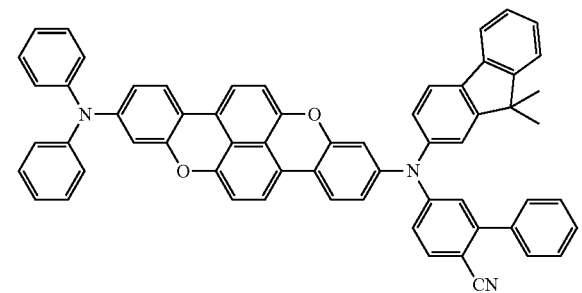
48
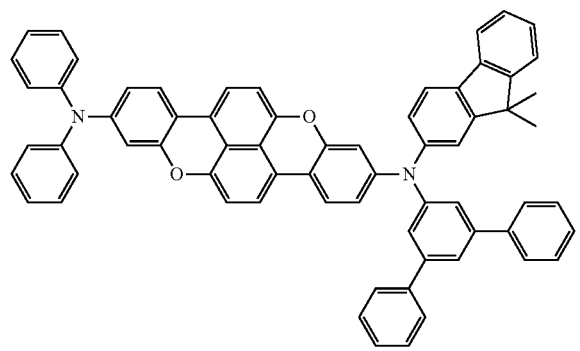
49
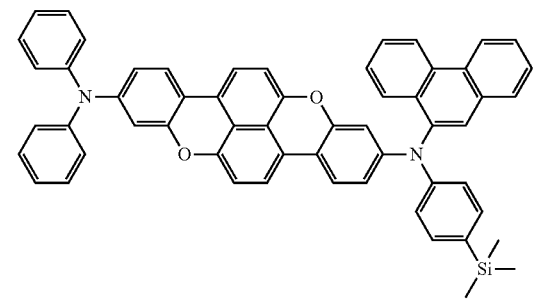
50
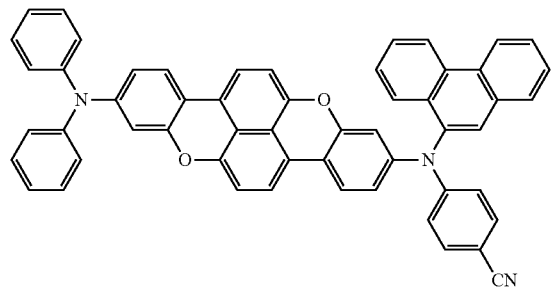
51
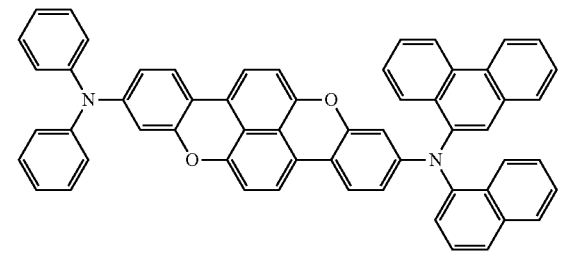

-continued
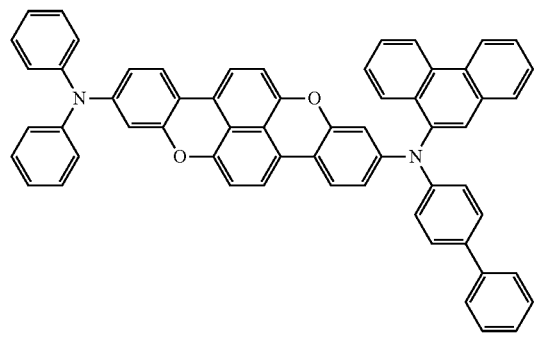
52
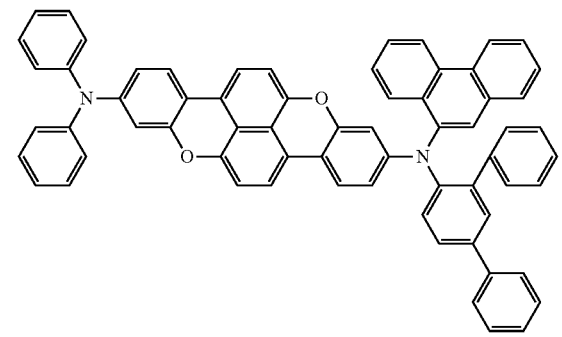
53
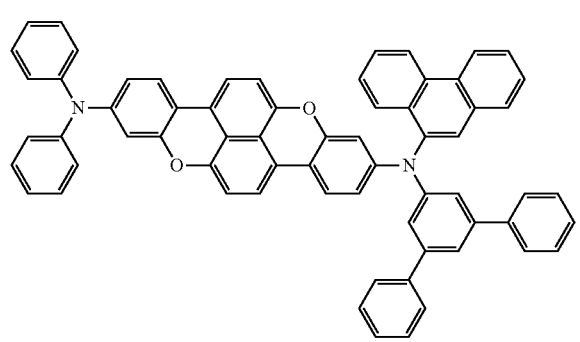
54
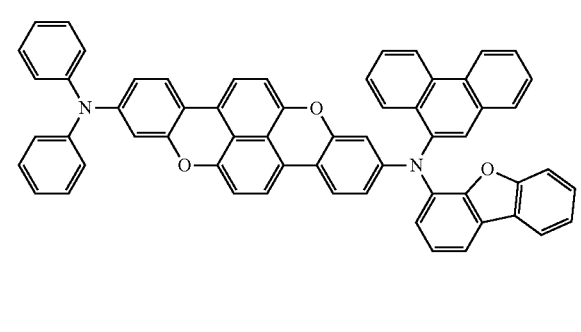
55
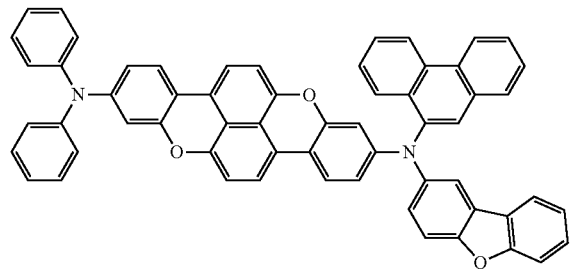
56
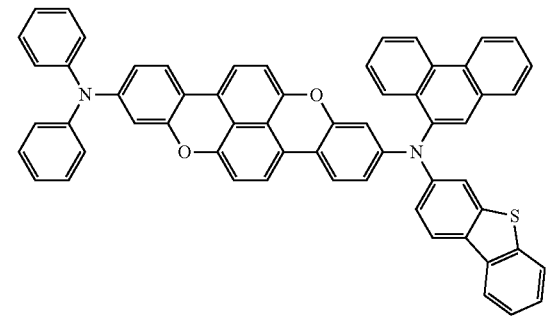
57
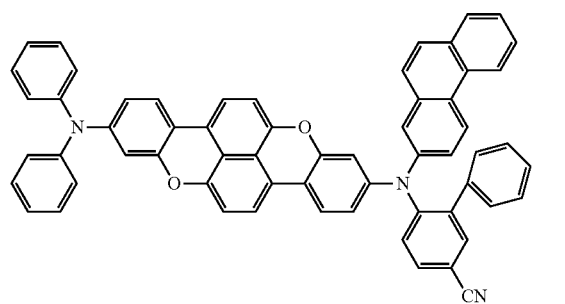
58
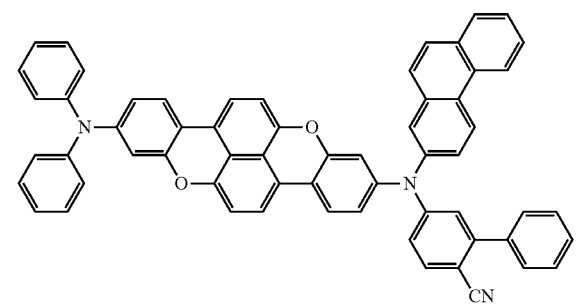
59
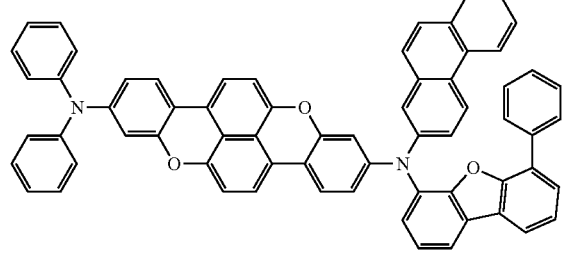
60
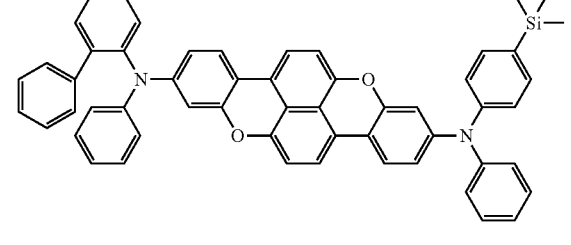
61

-continued
62
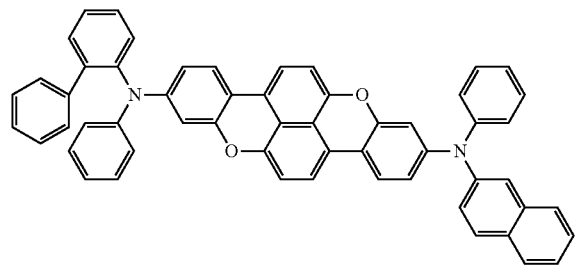
63
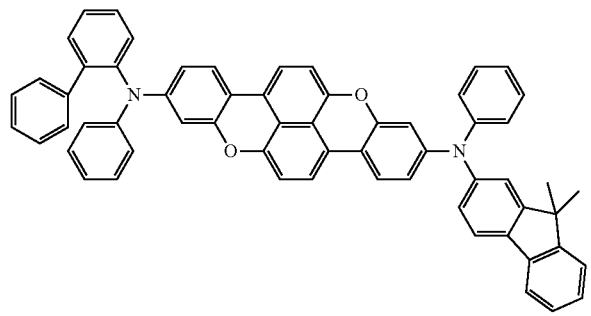
64
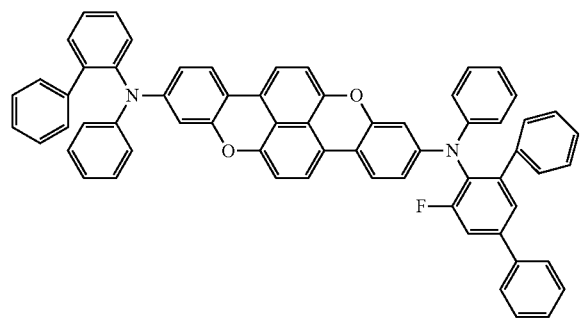
65
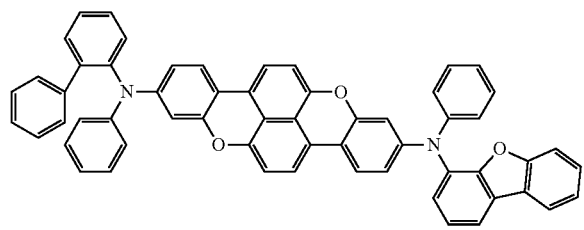
66
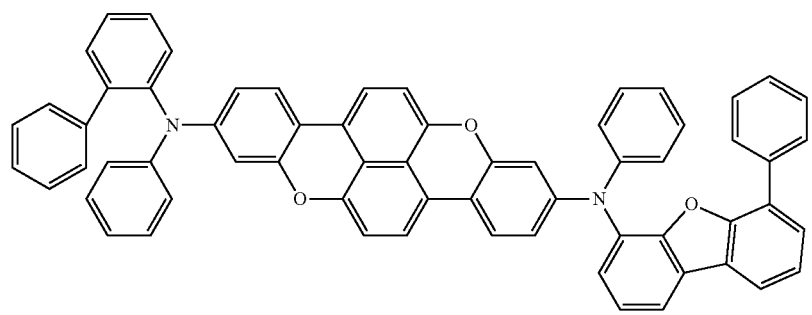
67
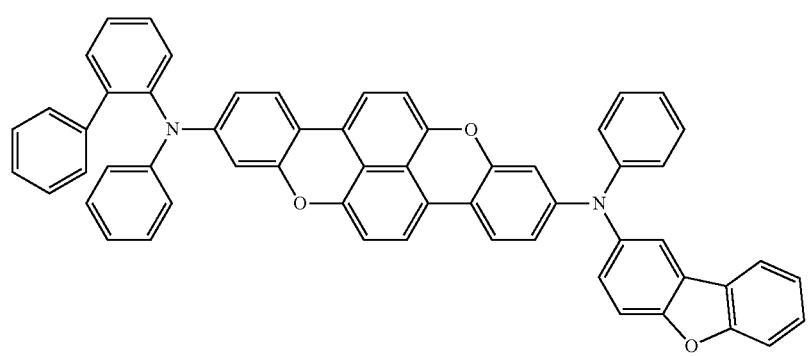

-continued
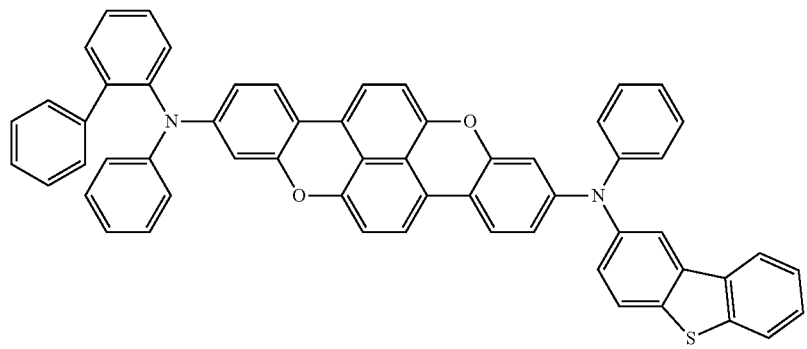
68
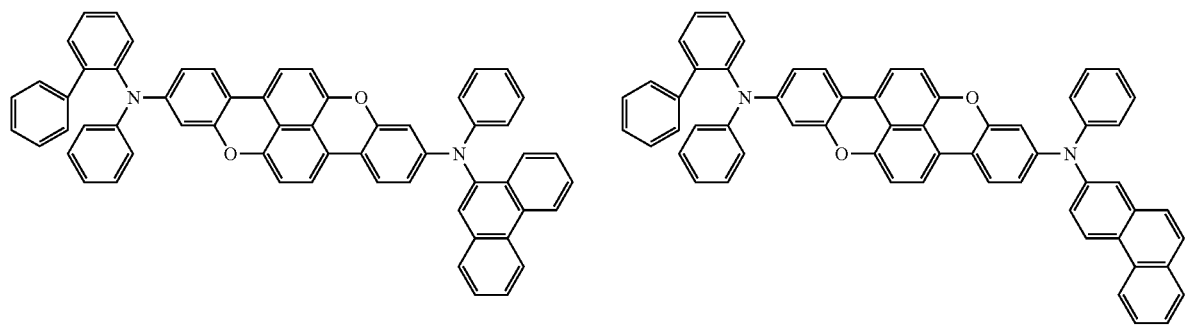
69  70
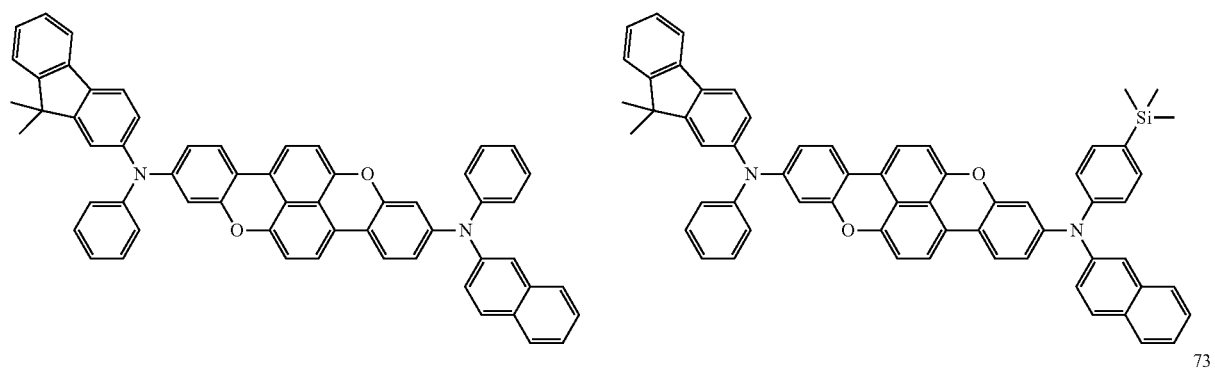
71  72
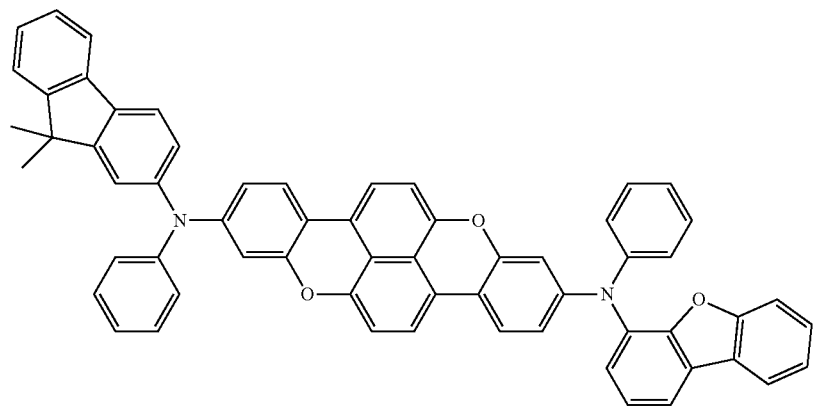
73

74
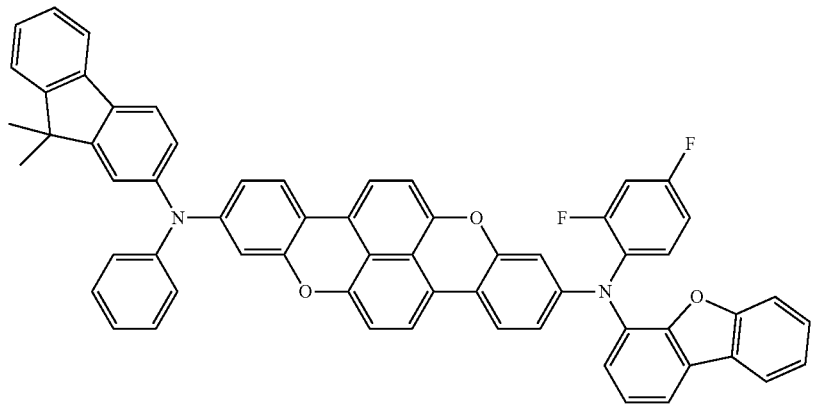
75
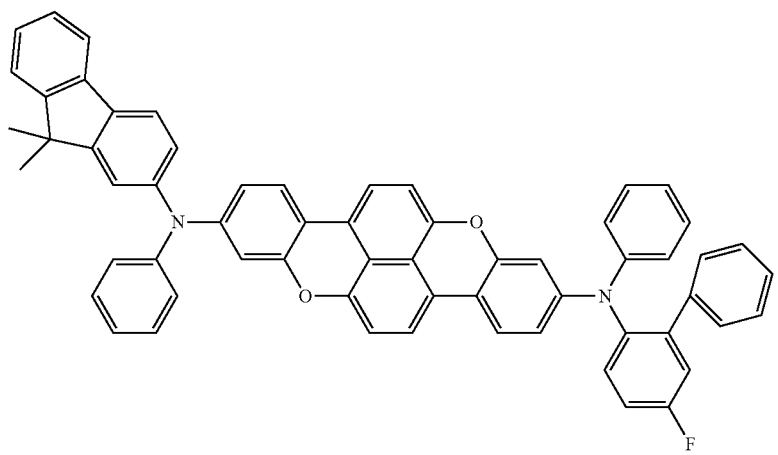
76
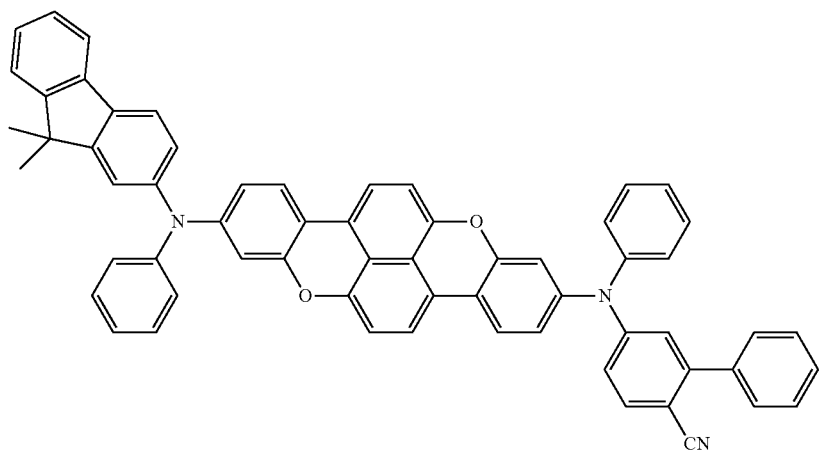

-continued
77
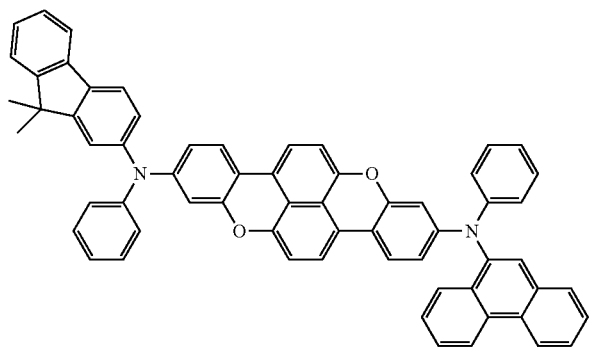
78
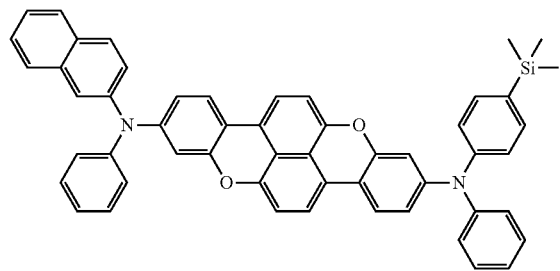
79
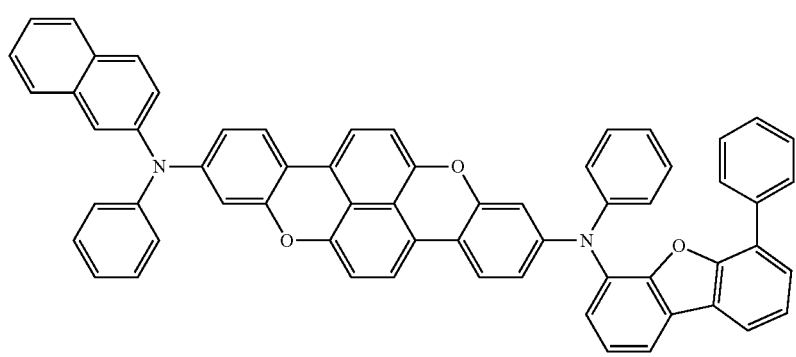
80
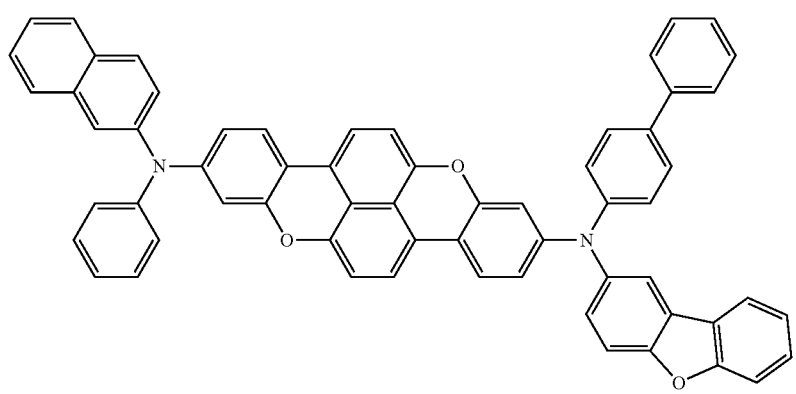
81
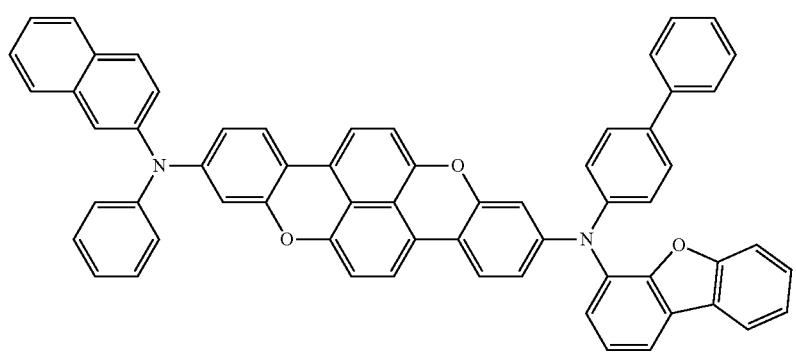

-continued
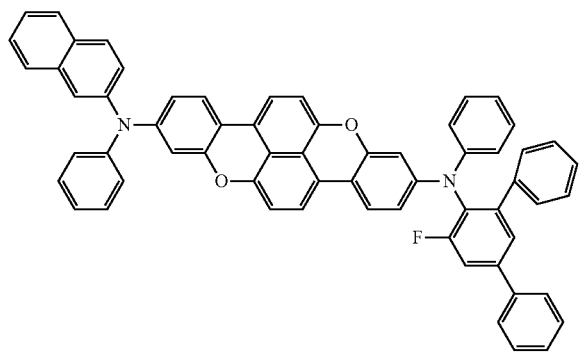
82
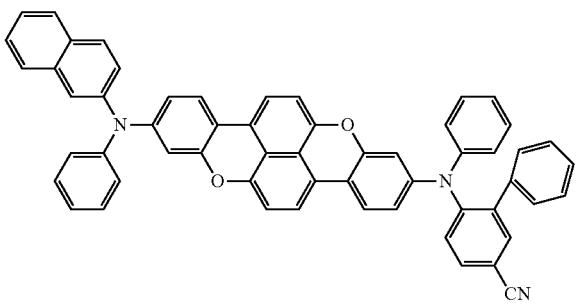
83
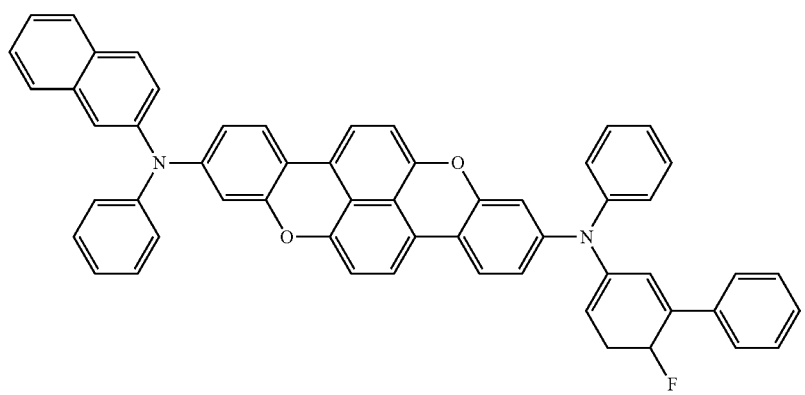
84
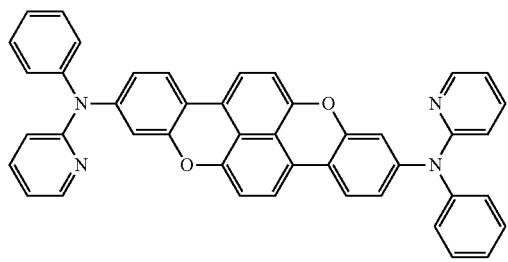
85
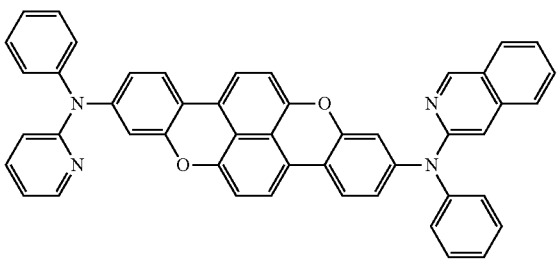
86
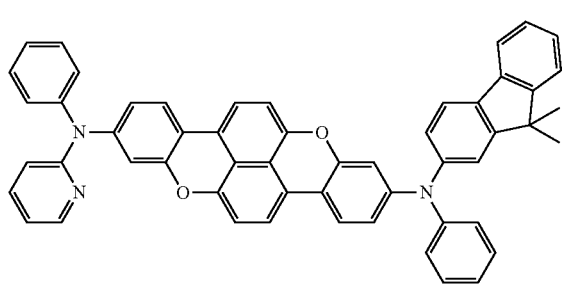
87
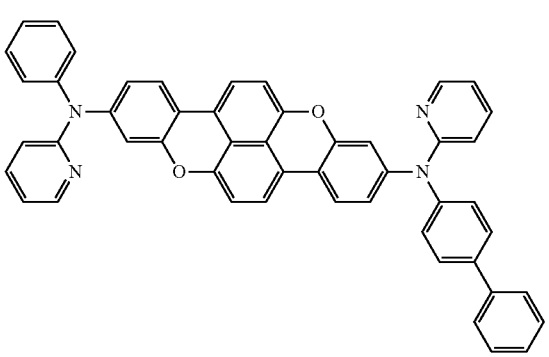
88
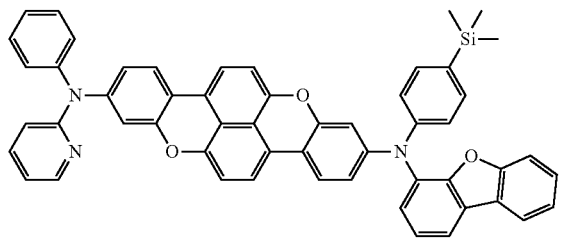
89
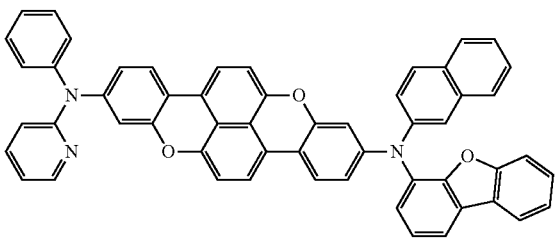
90

-continued
91
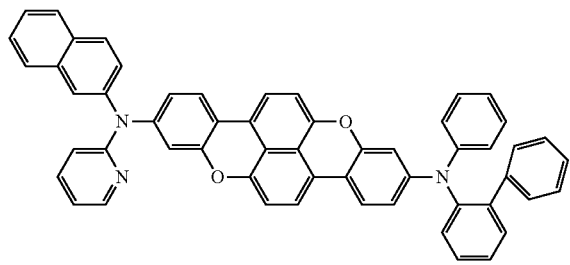
92
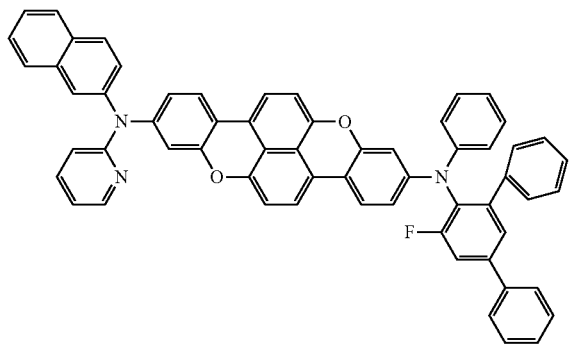
93
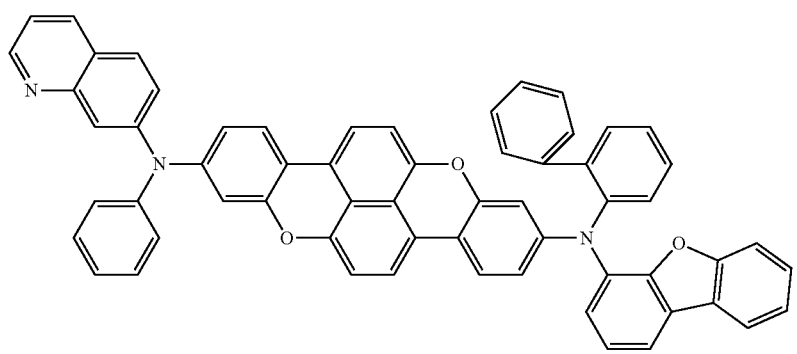
94
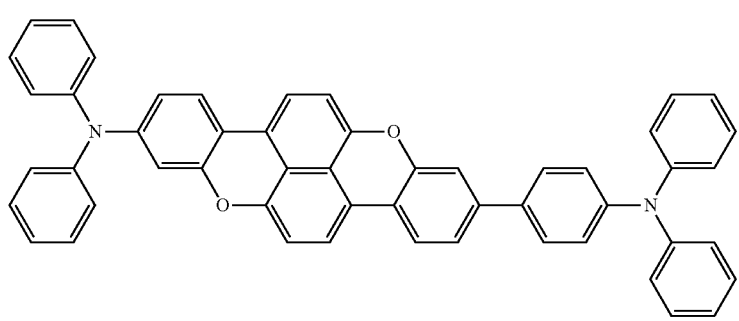
95
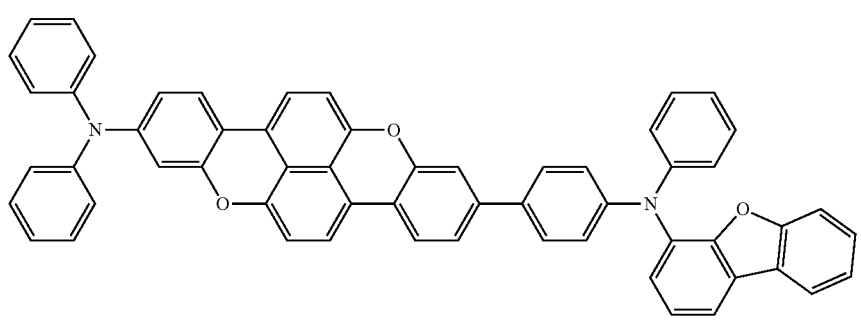

96

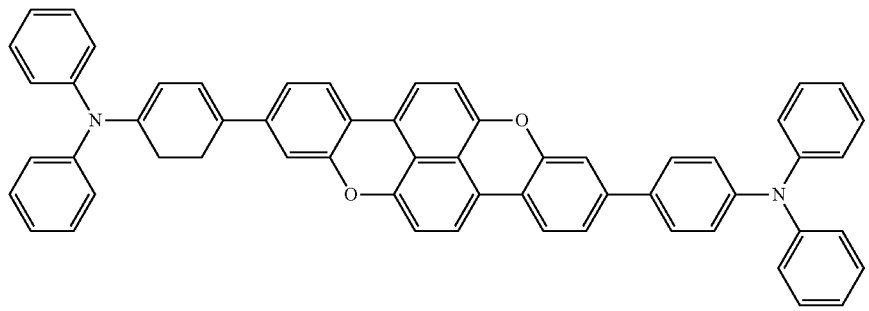

The condensed cyclic compound of Formula 1 may include a core represented by

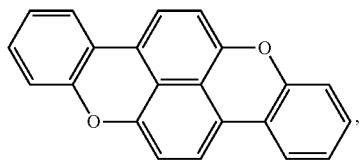

with oxygens in symmetrical positions. Unshared electron pairs of the oxygens may provide extra electrons, so that the condensed cyclic compound has a molecular structure that is rich in π-electrons. This may help increase a transition probability, so that the condensed cyclic compound of Formula 1 may help improve emission efficiency.

An organic light-emitting device including the condensed cyclic compound represented by Formula 1, above, may have a low driving voltage, a high luminance, a high efficiency, and/or a long lifetime.

The condensed cyclic compound of Formula 1 may be synthesized using a suitable organic synthesis method. Methods of synthesizing the condensed cyclic compounds of Formula 1 may be understood based on the examples that will be described below.

The condensed cyclic compound of Formula 1 may be included between a pair of electrodes of an organic light-emitting device. In an implementation, the condensed cyclic compound of Formula 1 may be in an electron transport region, e.g., in an electron transport layer.

According to another embodiment, an organic light-emitting device may include a first electrode, a second electrode opposite to the first electrode, and an organic layer between the first electrode and the second electrode and including an emission layer. The organic layer may include at least one condensed cyclic compound represented by Formula 1, above.

As used herein, "(for example, the organic layer) including at least one condensed cyclic compound means that "(the organic layer) including one of the condensed cyclic compounds of Formula 1 above, or at least two different condensed cyclic compounds of Formula 1 above".

In an implementation, the organic layer may include only Compound 1 above as the condensed cyclic compound. In this regard, Compound 1 may be present in the electron transport layer of the organic light-emitting device. In some embodiments, the organic layer may include Compounds 1 and 2 as the condensed cyclic compounds. In this regard, Compounds 1 and 2 may be present both in the same layer (for example, in the electron transport layer) or may be present in different layers (for example, in the emission layer and the electron transport layer, respectively).

The organic layer may include i) a hole transport region between the first electrode and the emission layer and including at least one of a hole injection layer, a hole transport layer, a buffer layer, and an electron blocking layer; and ii) an electron transport region between the emission layer and the second electrode and including at least one of a hole blocking layer, an electron transport layer, and an election injection layer. The electron transport region may include the condensed cyclic compound represented by Formula 1 above. For example, the electron transport region may include the electron transport layer, the electron transport layer may include the condensed cyclic compound represented by Formula 1 above.

As used herein, the term "organic layer" refers to a single layer and/or a plurality of layers disposed between the first and second electrodes of the organic light-emitting device. A material in the "organic layer" in not limited to an organic material.

Hereinafter, a structure of an organic light-emitting device according to an embodiment and a method of manufacturing the same will now be described with reference to the FIGURE.

The FIGURE illustrates a schematic sectional view of an organic light-emitting device 10 according to an embodiment. Referring to the FIGURE, the organic light-emitting device 10 may include a first electrode 110, an organic layer 150, and a second electrode 190.

A substrate (not shown) may be disposed under the first electrode 110 or on the second electrode 190 in the FIGURE. The substrate may be a glass or transparent plastic substrate with good mechanical strength, thermal stability, transparency, surface smoothness, ease of handling, and water resistance.

For example, the first electrode 110 may be formed by depositing or sputtering a first electrode-forming material on the substrate 11. When the first electrode 110 is an anode, a material having a high work function may be used as the first electrode-forming material to facilitate hole injection. The first electrode 110 may be a reflective electrode, a semi-transmissive electrode, or a transmissive electrode. Transparent and conductive materials such as ITO, IZO, $SnO_2$, and ZnO may be used to form the first electrode. The first electrode 110 as a semi-transmissive electrode or a reflective electrode may be formed of at least one material selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure or a multi-layer structure including a plurality of layers. For example, the first electrode 110 may have a three-layered structure of ITO/Ag/ITO.

The organic layer 150 may be disposed on the first electrode 110. The organic layer 150 may include an emission layer (EML).

The organic layer 150 may include a hole transport region between the first electrode and the EML, and an electron transport region between the EML and the second electrode.

For example, the hole transport region may include at least one of a hole injection layer (HIL), a hole transport layer (HTL), a buffer layer, and an electron blocking layer (EBL). For example, the electron transport layer may include at least one of a hole blocking layer (HBL), an electron transport layer (ETL), and an electron injection layer (EIL).

The hole transport region may have a single-layered structure including a single material, a single-layered structure including a plurality of materials, or a multi-layered structure including a plurality of layers including different materials.

In an implementation, the electron transport region may have a single-layered structure including a plurality of materials, or a multi-layered structure of HIL/HTL, HIL/HTL/buffer layer, HIL/buffer layer, HTL/buffer layer, or HIL/HTL/EBL, wherein these layers forming a multi-layered structure are sequentially disposed on the first electrode 110 in the order stated above.

When the hole transport region includes a HIL, the HIL may be formed on the first electrode 110 by using any of a variety of methods, for example, by using vacuum deposition, spin coating, casting, Langmuir-Blodgett (LB) deposition, inkjet printing, laser printing, laser induced thermal imaging (LITI), or the like.

When the HIL is formed using vacuum deposition, the deposition conditions may vary depending on the material that is used to form the HIL and the structure of the HIL. For example, the deposition conditions may be selected from the following conditions: a deposition temperature of about 100° C. to about 500° C., a degree of vacuum of about $10^{-8}$ to about $10^{-3}$ torr, and a deposition rate of about 0.01 to 100 Å/sec.

When the HIL is formed using spin coating, the coating conditions may vary depending on the material that is used to form the HIL and the structure of the HIL. For example, the coating conditions may be selected from the following conditions: a coating rate of about 2,000 rpm to about 5,000 rpm and a heat treatment temperature of about 800° C. to about 200° C.

When the hole transport region includes a HTL, the HTL may be formed on the first electrode 110 or the HIL by using any of a variety of methods, for example, by using vacuum deposition, spin coating, casting, Langmuir-Blodgett (LB) deposition, inkjet printing, laser printing, laser induced thermal imaging (LITI), or the like. When the HTL is formed using vacuum deposition or spin coating, the conditions for deposition and coating may be similar to the above-described deposition and coating conditions for forming the HIL, and accordingly will not be described in detail.

In an implementation, the hole transport region may include at least one of m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), a compound represented by Formula 201 below, and a compound represented by Formula 202 below.

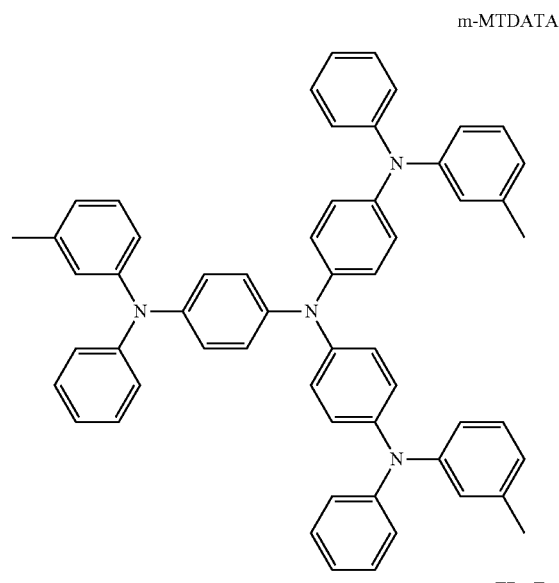

m-MTDATA

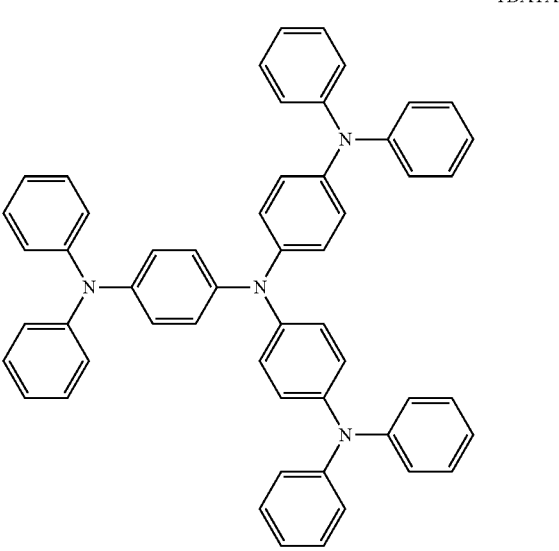

TDATA

2-TNATA
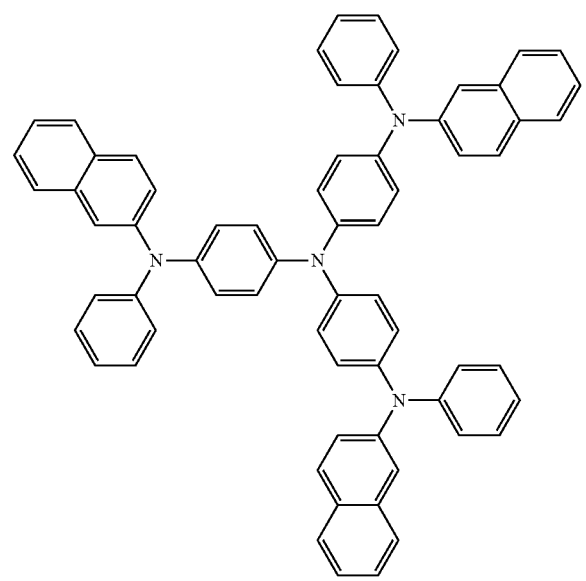
Spiro-TPD
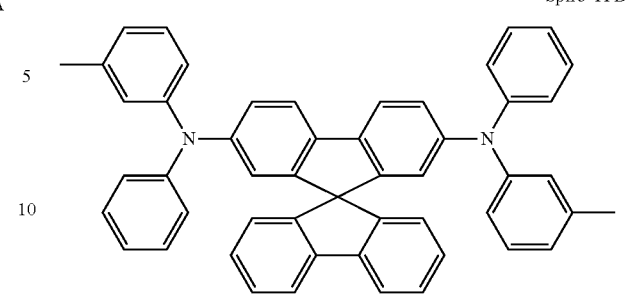
Spiro-NPB
α-NPB
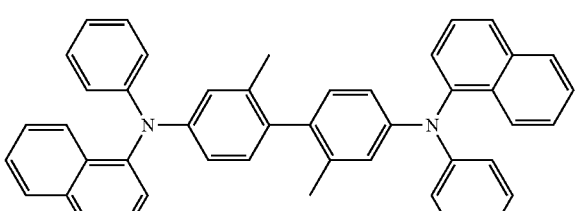
NPB
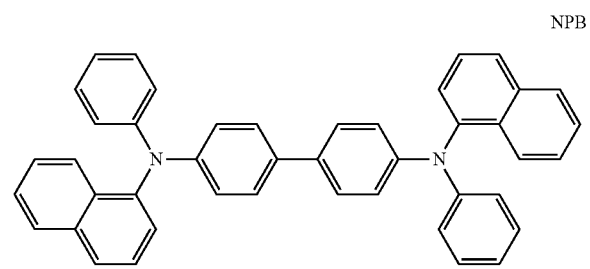
TAPC
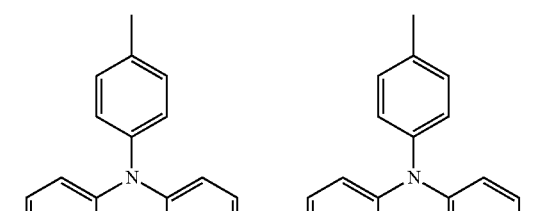
β-NPB
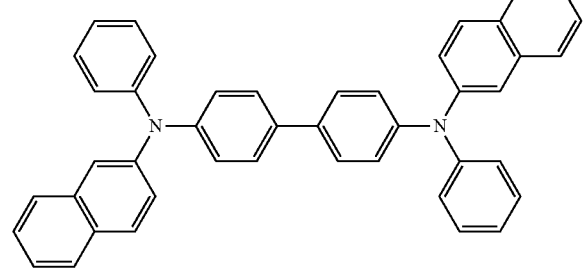
HMTPD
TPD
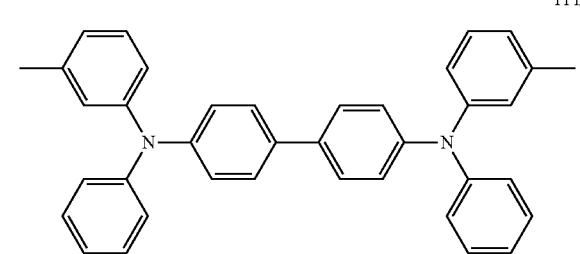
<Formula 201>
$R_{201}-(L_{201})_{xa1}-N\begin{matrix}(L_{202})_{xa2}-R_{202}\\(L_{203})_{xa3}-R_{203}\end{matrix}$ -continued

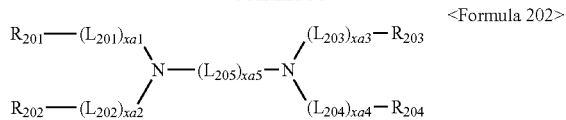
<Formula 202>

In Formulae 201 and 202

$L_{201}$ to $L_{205}$ may be each independently defined as described above in conjunction with $L_1$ in Formula 1;

xa1 to xa4 are each independently selected from 0, 1, 2, and 3;

xa5 may be selected from 1, 2, 3, 4, and 5;

$R_{201}$ to $R_{205}$ may be each independently defined as described above in conjunction with $R_1$ in Formula 1.

For example, in Formulae 201 and 202, $L_{201}$ to $L_{205}$ may be each independently:

a phenylene group, a naphthylene group, a fluorenylene group, a spiro-fluorenylene group, a benzofluoene group, a dibenzofluoene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, or a triazinylene; or a phenylene group, a naphthylene group, a fluorenylene group, a spiro-fluorenylene group, a benzofluoreneylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, or a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, xa1 to xa4 may be each independently 0, 1, or 2;

xa5 may be 1, 2, or 3;

$R_{201}$ to $R_{205}$ may be each independently:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

In an implementation, the compound of Formula 201 may be represented by Formula 201A.

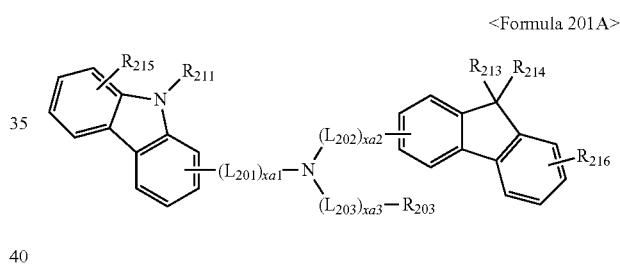
<Formula 201A>

For example, the compound of Formula 201 may be represented by Formula 201A-1.

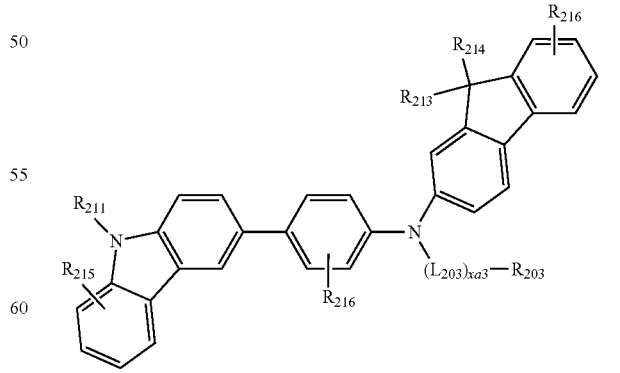
<Formua 201A-1>

In an implementation, the compound of Formula 201 may be represented by Formula 201A.

<Formula 202A>

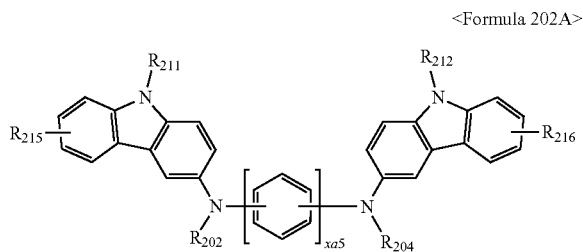

In Formulae 201A, 201A-1, and 202A, $L_{201}$ to $L_{203}$, xa1 to xa3, xa5, and $R_{202}$ to $R_{204}$ may be defined as described in conjunction with Formula 201;

$R_{211}$ may be defined as described in conjunction with $R_{203}$ in Formula 201;

$R_{213}$ to $R_{216}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic group, or a salt thereof, a sulfonic acid group, or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cyclo alkyl group, a $C_2$-$C_{10}$ heterocyclo alkyl group, a $C_3$-$C_{10}$ cyclo alkenyl group, a $C_2$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic hetero-condensed polycyclic group.

In an implementation, in Formulae 201A, 201A-1, and 202A, $L_{201}$ to $L_{203}$ may be each independently:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, or a triazinylene group; or a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, or a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, xa1 to xa3 may be each independently 0 or 1, $R_{203}$, $R_{211}$, and $R_{212}$ may be each independently:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

$R_{213}$ and $R_{214}$ may be each independently:

a $C_1$-$C_{20}$ alkyl group or a $C_1$-$C_{20}$ alkoxy group;

a $C_1$-$C_{20}$ alkyl group or a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

$R_{215}$ and $R_{216}$ may be each independently:

a hydrogen, a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, or a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and xa5 may be 1 or 2.

In an implementation, in Formulae 201A and 201A-1, $R_{213}$ and $R_{214}$ may be linked to each other to form a saturated or unsaturated ring.

The compound represented by Formula 201, and the compound represented by Formula 202 may include compounds HT1 to HT20 illustrated below.

HT1

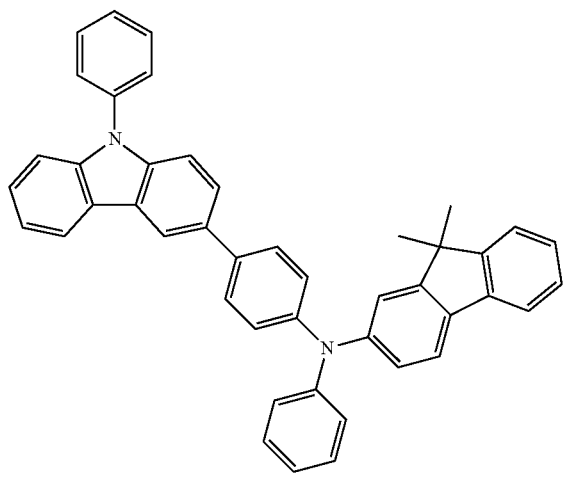

HT2

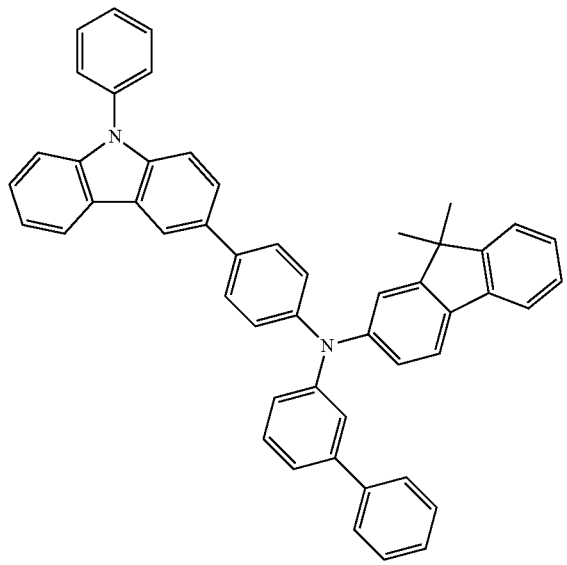

HT3
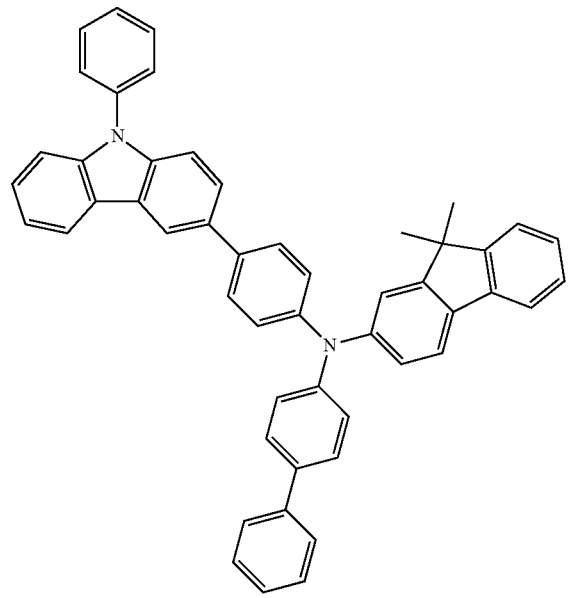
HT5
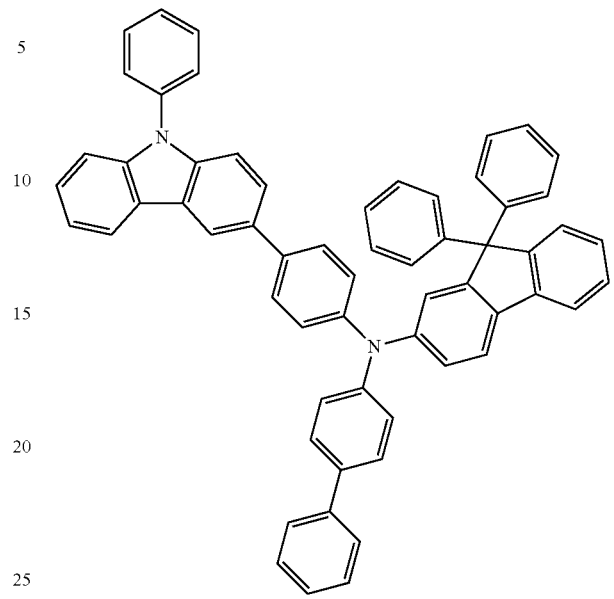
HT4
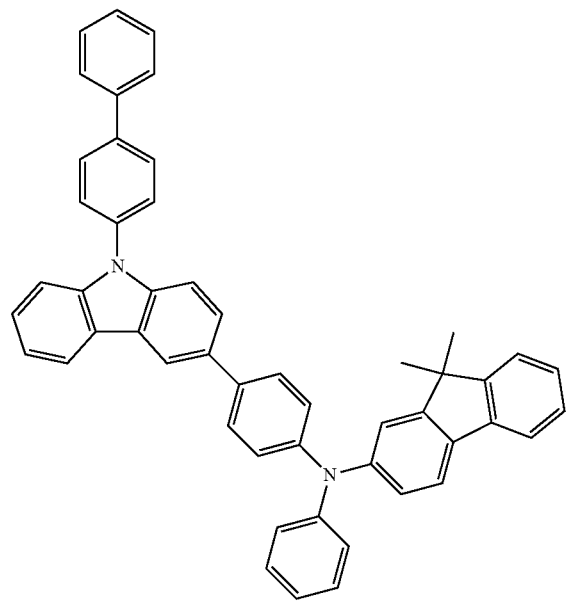
HT6
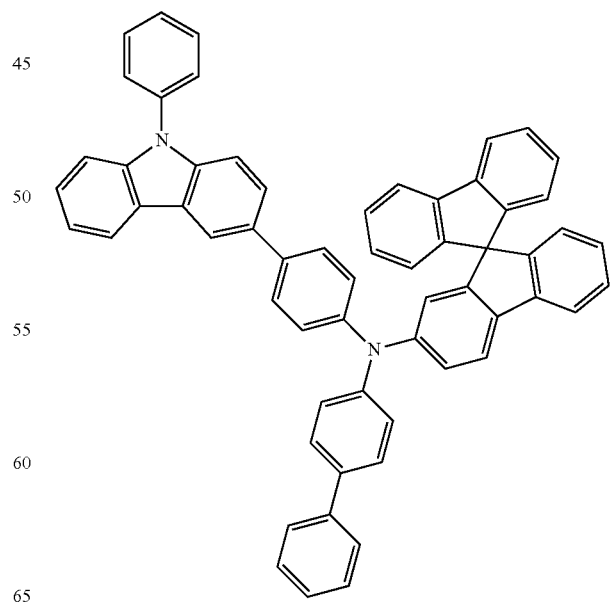

HT7
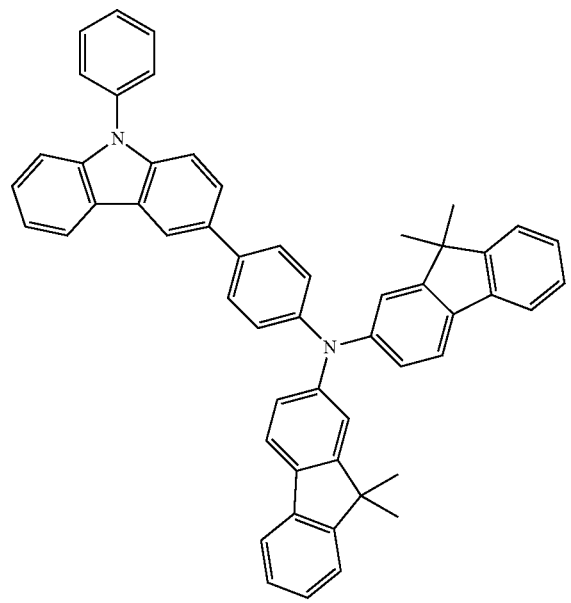
HT9
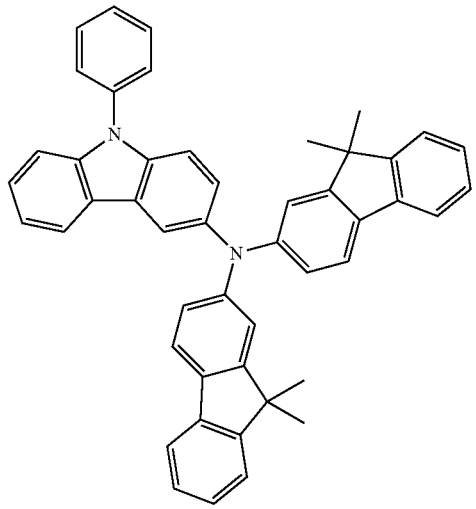
HT8
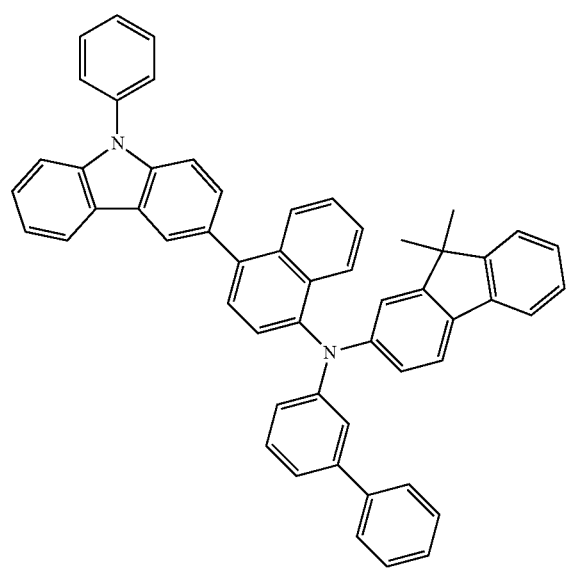
HT10
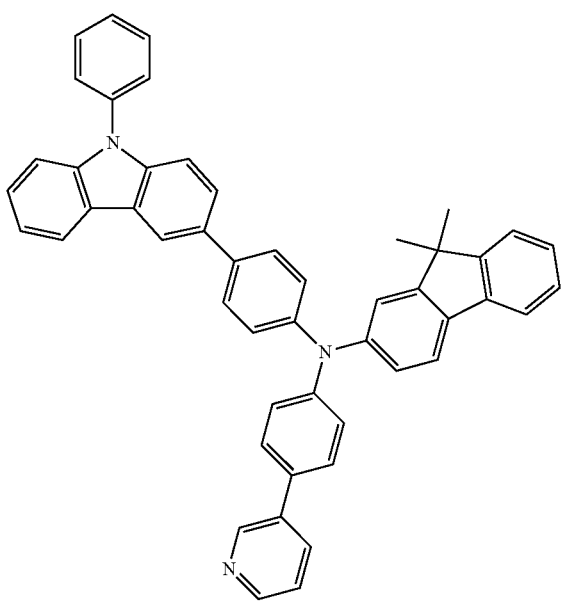

HT11
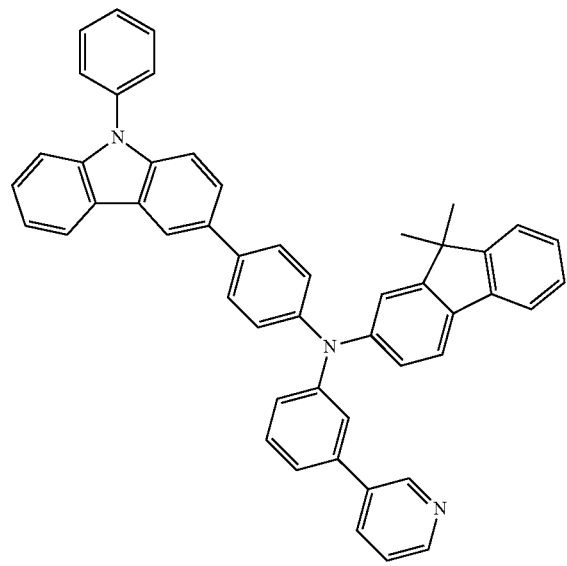
HT12
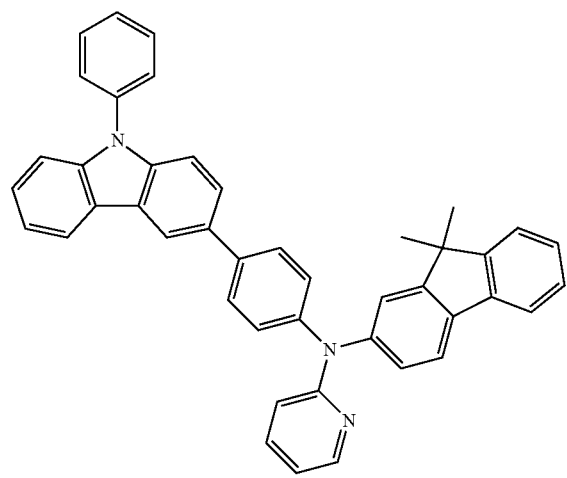
HT13
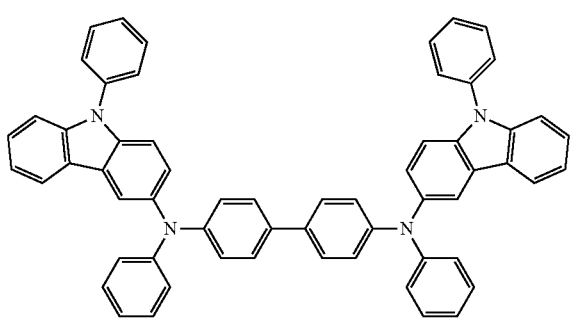
HT14
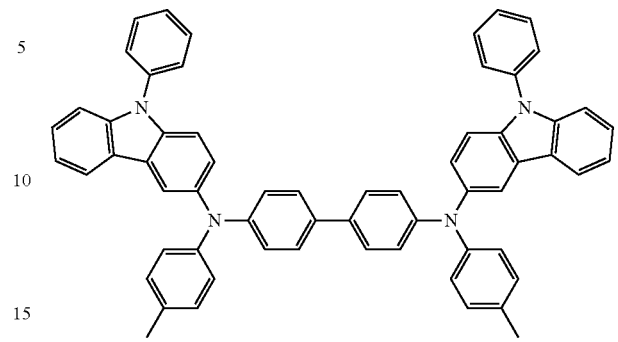
HT15
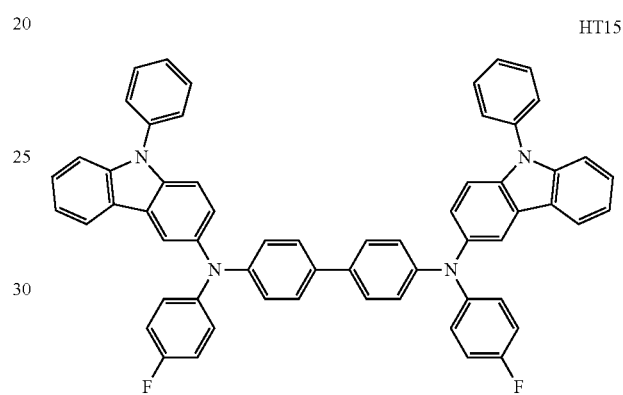
HT16
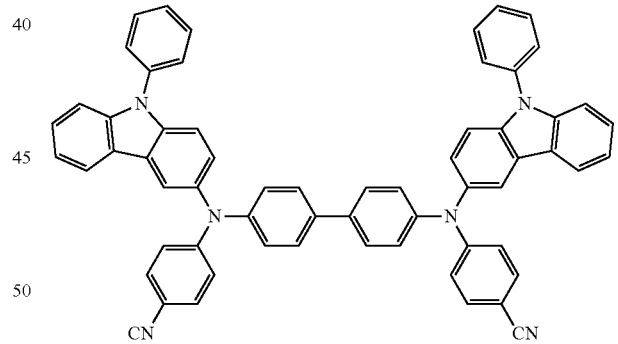
HT17
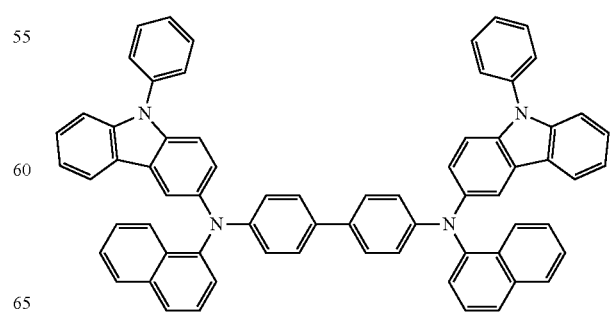

HT18

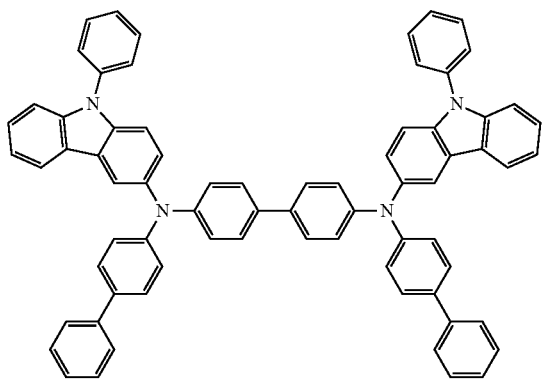

HT19

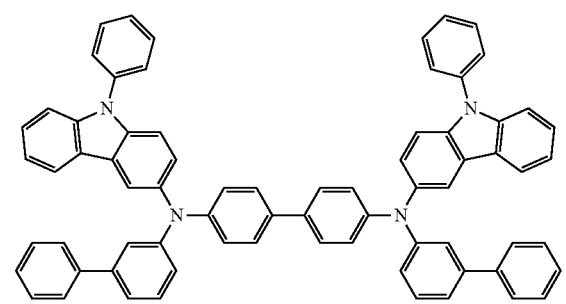

HT20

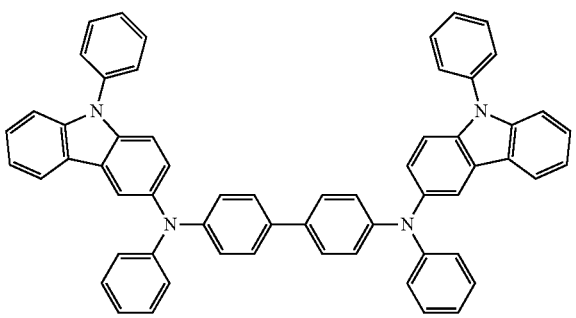

A thickness of the hole transport region may be from about 100 Å to about 10,000 Å, e.g., about 100 Å to about 1000 Å. When the hole transport region includes a HIL and a HTL, a thickness of the HIL may be from about 100 Å to about 10,000 Å, e.g., about 100 Å to about 1,000 Å, and a thickness of the HTL may be from about 50 Å to about 2,000 Å, e.g., about 100 Å to about 1,500 Å. When the thicknesses of the hole transport region, the HIL, and the HTL are within these ranges, satisfactory hole transport characteristics may be obtained without a substantial increase in driving voltage.

The hole transport region may further include a charge-generating material to help improve conductivity, in addition to the materials as described above. The charge-generating material may be homogeneously or inhomogeneously dispersed in the hole transport region.

The charge-generating material may be, e.g., a p-dopant. The p-dopant may be one of quinone derivatives, metal oxides, and compounds with a cyano group. Non-limiting examples of the p dopant may include quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and Compound HT-D1 below.

<Compound HT-D1>

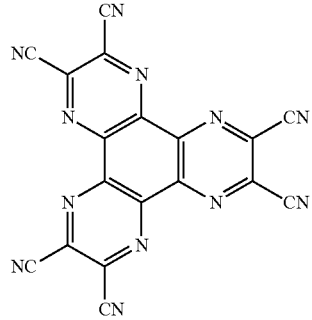

<F4-TCNQ>

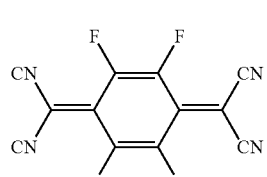

The hole transport region may further include at least one of a buffer layer and an EBL, in addition to the HIL and HTL described above. The buffer layer may help compensate for an optical resonance distance of light according to a wavelength of the light emitted from the EML, and thus may improve light-emission efficiency. A material in the buffer layer may be a suitable material used in the hole transport region. The EBL may block migration of electrons from the electron transport region into the EML.

The EML may be formed on the first electrode 110 or the hole transport region by using any of a variety of methods, e.g., by using vacuum deposition, spin coating, casting, Langmuir-Blodgett (LB) deposition, inkjet printing, laser printing, laser induced thermal imaging (LITI), or the like. When the EML is formed using vacuum deposition or spin coating, the deposition and coating conditions for forming the EML may be similar to the above-described deposition and coating conditions for forming the HIL, and accordingly will not be described in detail.

When the organic light-emitting device 10 is a full color organic light-emitting device, the EML may be patterned into a red emission layer, a green emission layer, and a blue emission layer to correspond to individual subpixels, respectively. In an implementation, the EML may have a structure in which a red emission layer, a green emission layer and a blue emission layer are stacked upon one another, or a structure including a mixture of a red light-emitting material, a green light-emitting material, and a blue light-emitting material, and thus may emit white light.

The EML may include a host and a dopant.

For example, the host may include at least one of TPBi, TBADN, ADN (also referred to as "DNA"), CBP, CDBP, and TCP.

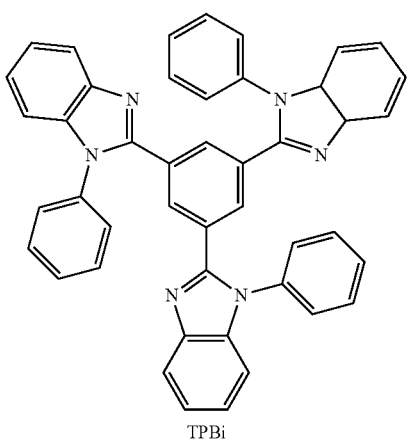

TPBi

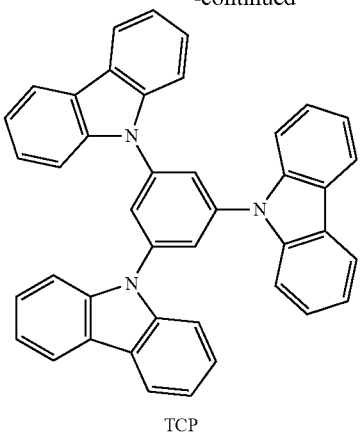

TCP

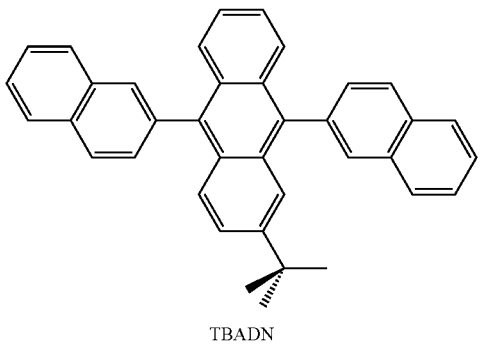

TBADN

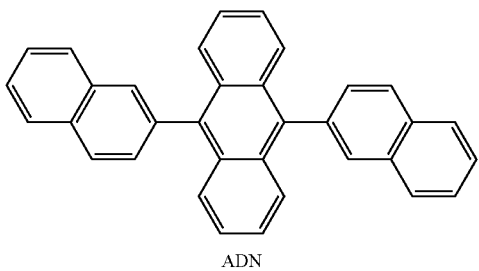

ADN

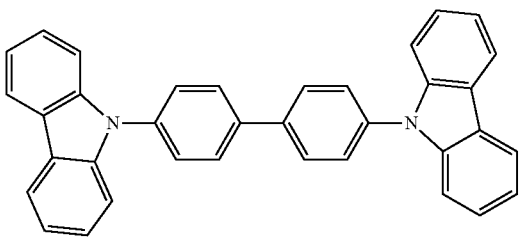

CBP

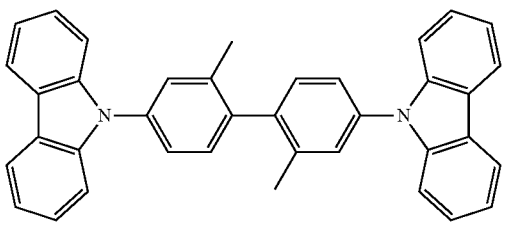

CDBP

In an implementation, the host may include a compound represented by Formula 301.

$$AR_{301}-[(L_{301})_{xb1}-R_{301}]_{xb2}$$  <Formula 301>

In Formula 301, $AR_{301}$ may be:

a naphthalene, a heptalene, a fluorene, a spiro-fluorene, a benzofluorene, a dibenzofluorene, a phenalene, a phenanthrene, an anthrazene, a fluoranthene, a triphenylene, a pyrene, a chrysene, a naphthacene, a picene, a perylene, a pentaphene, or an indenoanthrazene; and a naphthalene, a heptalene, a fluorene, a spiro-fluorene, a benzofluorene, a dibenzofluorene, a phenalene, a phenanthrene, an anthrazene, a fluoranthene, a triphenylene, a pyrene, a chrysene, a naphthacene, a picene, a perylene, a pentaphene, or an indenoanthrazene, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cyclo alkyl group, a $C_2$-$C_{10}$ heterocyclo alkyl group, a $C_3$-$C_{10}$ cyclo alkenyl group, a $C_2$-$C_{10}$ heterocyclo alkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, and —Si($Q_{301}$)($Q_{302}$)($Q_{303}$) (where $Q_{301}$ to $Q_{303}$ may be each independently, a hydrogen, a $C_1$-$C_{60}$ alkyl group, a $C_2$-$C_{60}$ alkenyl group, a $C_6$-$C_{60}$ aryl group, or a $C_2$-$C_{60}$ heteroaryl group), $L_{301}$ may be defined as described above in conjunction with $L_{201}$ in Formula 201, $R_{301}$ may be:

a $C_1$-$C_{20}$ alkyl group, or a $C_1$-$C_{20}$ alkoxy group;

a $C_1$-$C_{20}$ alkyl group, or a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xb1 may be selected from 0, 1, 2, and 3;
xb2 may be selected from 1, 2, 3, and 4.
For example, in Formula 301,
$L_{301}$ may be:
a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, or a chrysenylene group; or a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, or a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and $R_{301}$ may be:
a $C_1$-$C_{20}$ alkyl group, or a $C_1$-$C_{20}$ alkoxy group;
a $C_1$-$C_{20}$ alkyl group or a $C_1$-$C_{20}$ alkoxy group, each substituted at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, or a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, or a chrysenyl group; each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group.

For example, the host may include a compound represented by formula 301A.

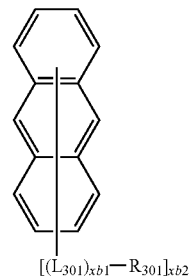

<Formula 301A>

$[(L_{301})_{xb1}-R_{301}]_{xb2}$

Substituents in Formula 301A may be defined as described above in conjunction with other formulae herein.

The compound of Formula 301 may include at least one of Compounds H1 to 42.

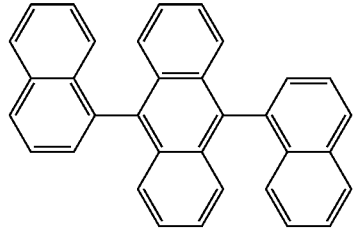

H1

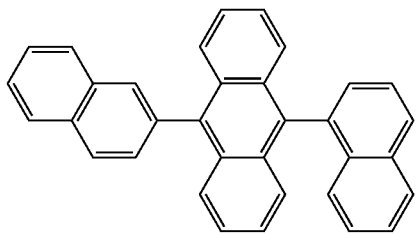

H2

-continued
H3
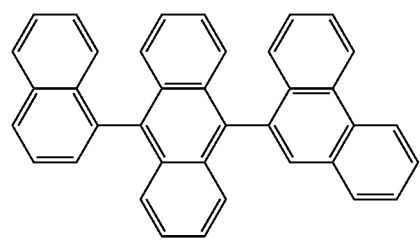
H4
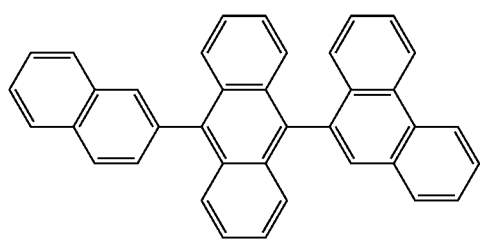
H5
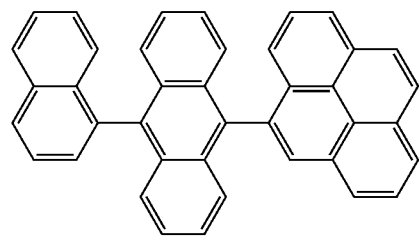
H6
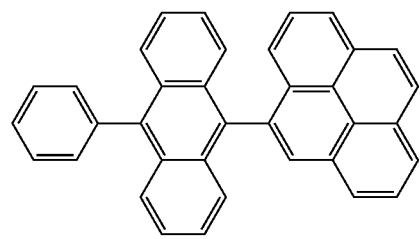
H7
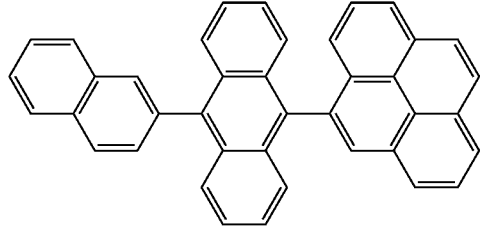
H8
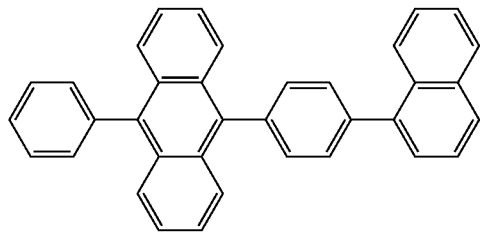
-continued
H9
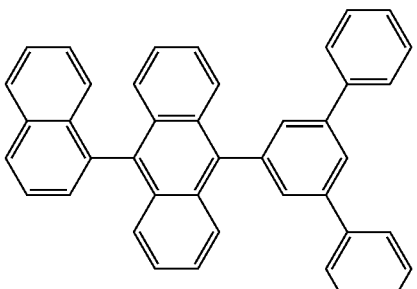
H10
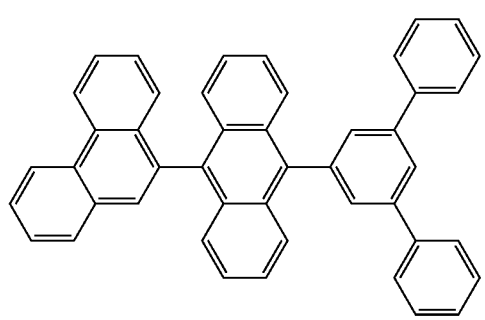
H11
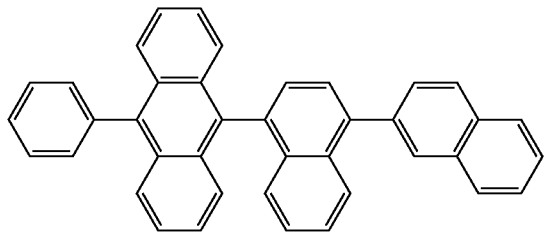
H12
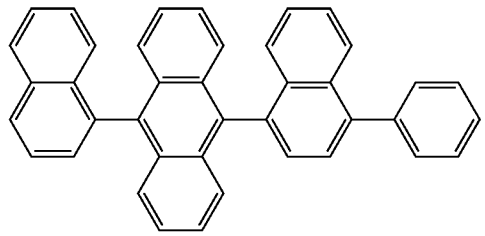
H13
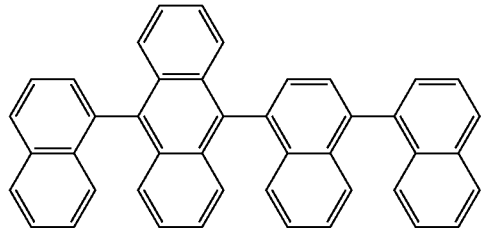
H14
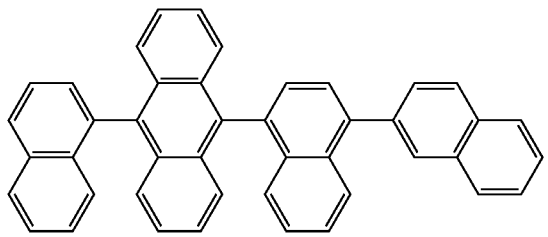

75
-continued

H15 H16 H17 H18 H19

76
-continued

H20 H21 H22 H23 H24

H25 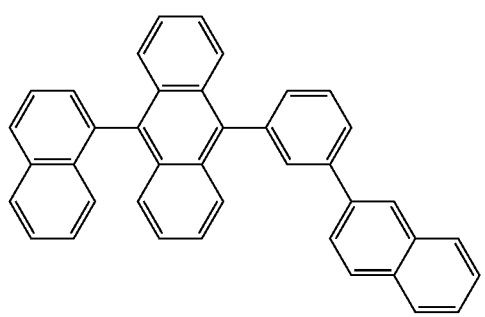
H26 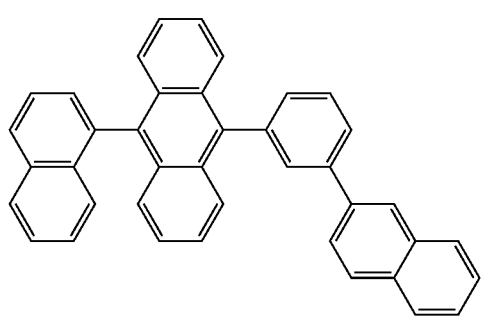
H27 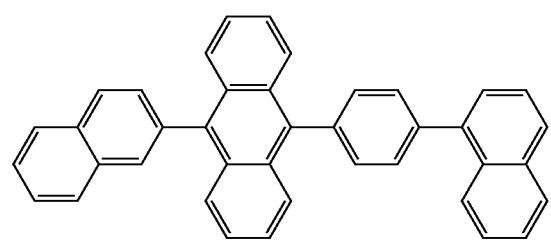
H28 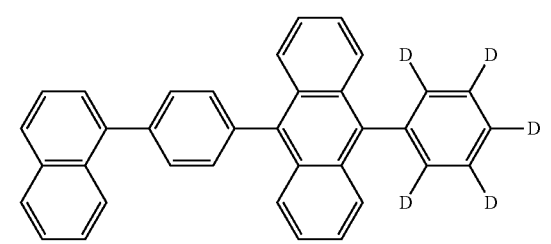
H29 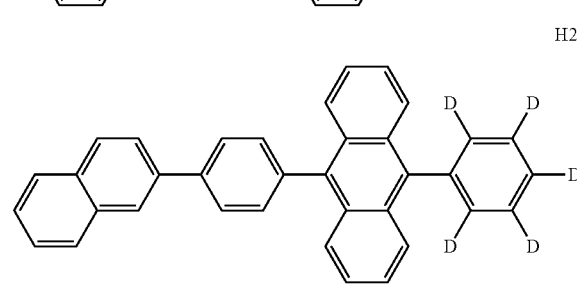
H30 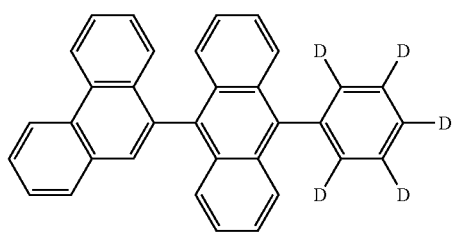
H31 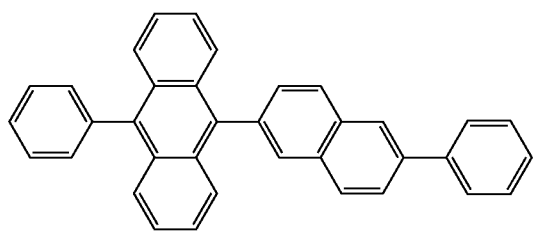
H32 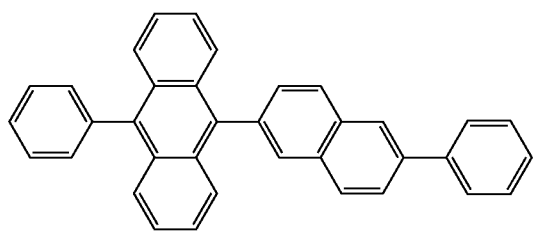
H33 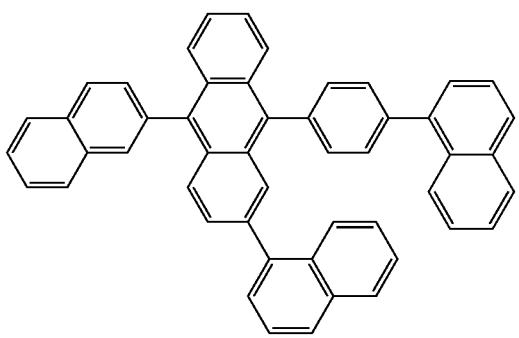
H34 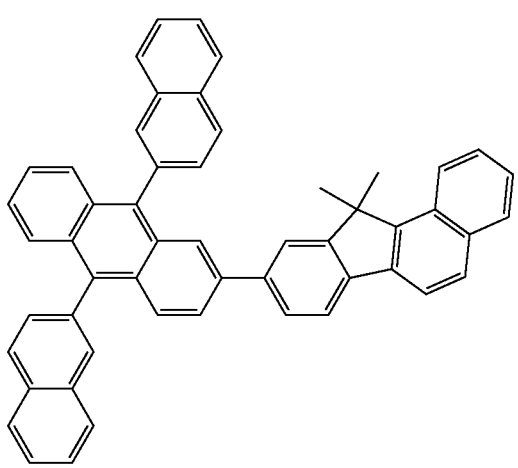

H35
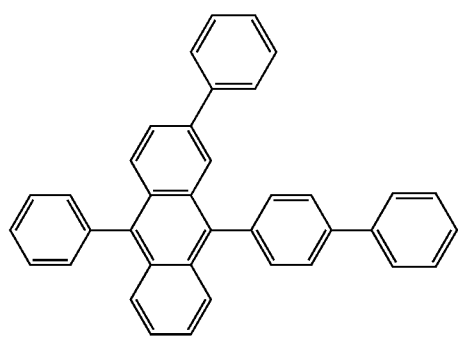
H36
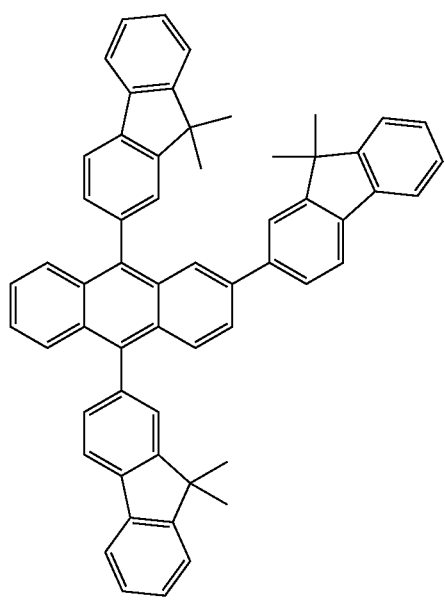
H37
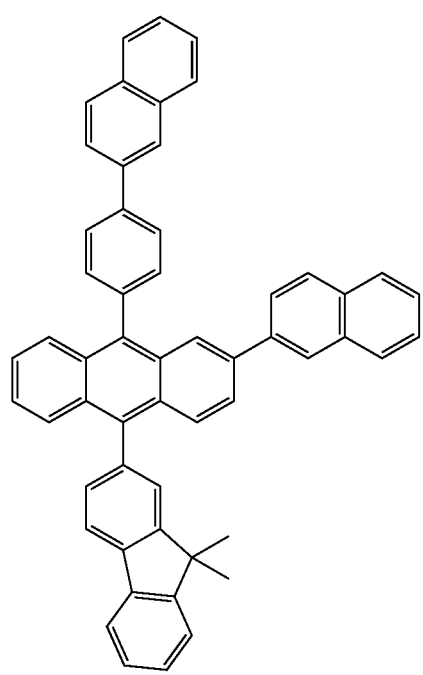
H38
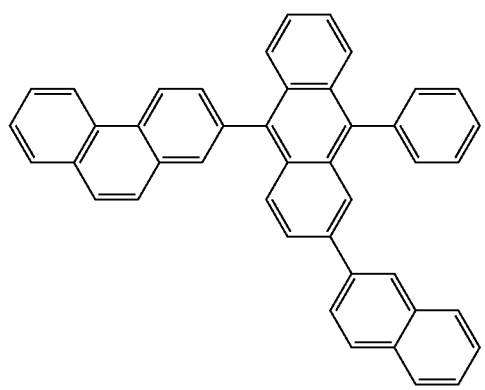
H39
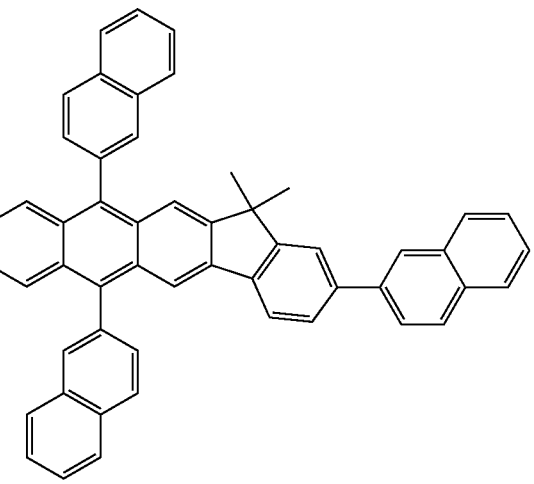
H40
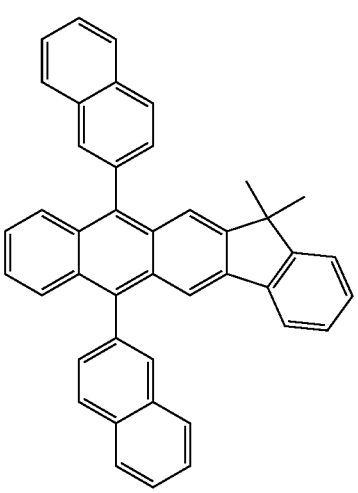

H41
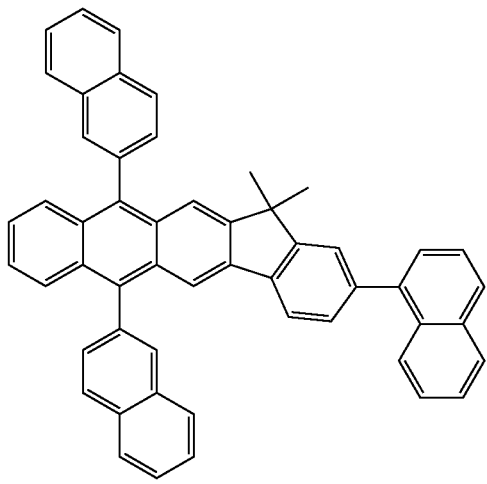
H42
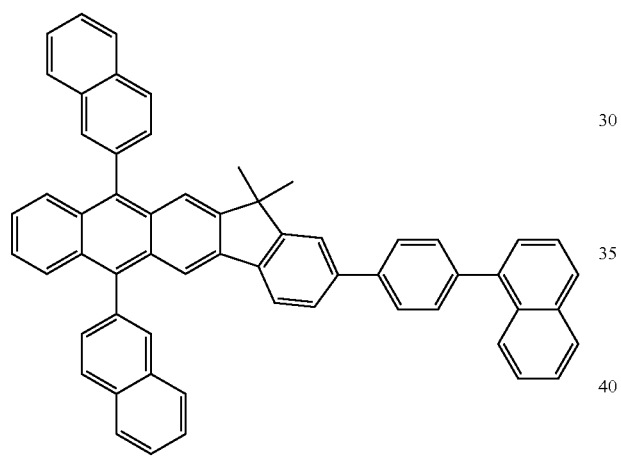
In an implementation, the host may include at least one of Compounds H43 to H49.
H43
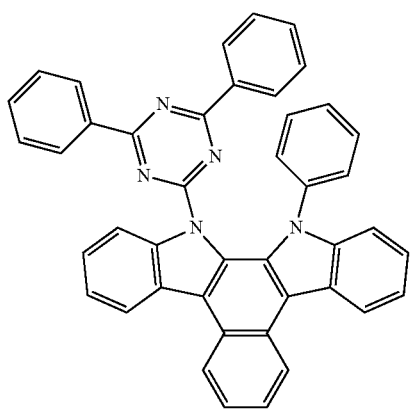
H44
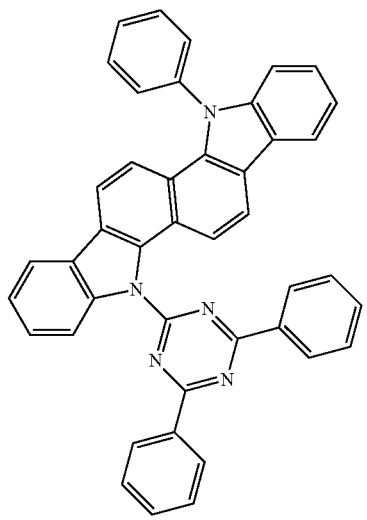
H45
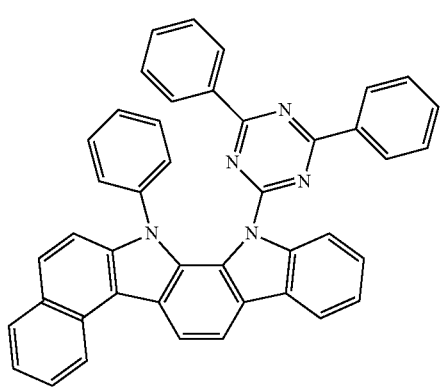
H46
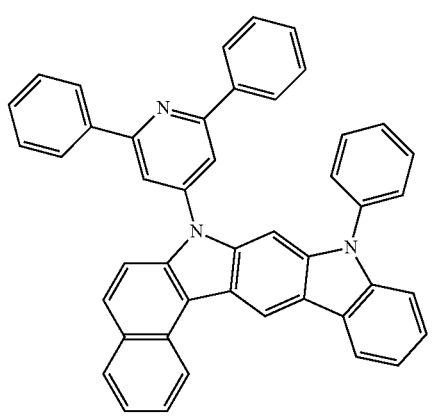

H47

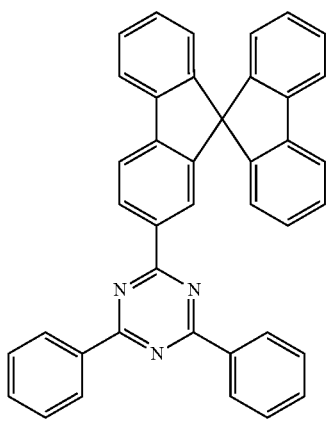

H48

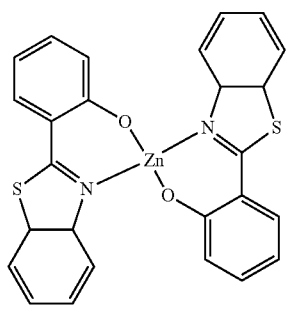

H49

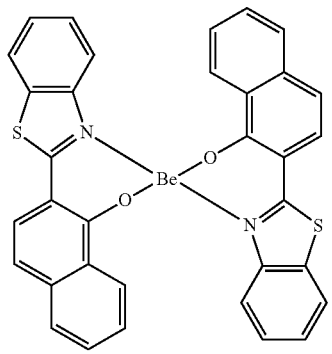

The dopant may include a condensed cyclic compound of Formula 1.

In an implementation, an amount of the dopant in the EML may be from about 0.01 parts to about 15 parts by weight, based on 100 parts by weight of the host.

The thickness of the EML may be about 100 Å to about 1,000 Å, e.g., about 200 Å to about 600 Å. When the thickness of the EML is within these ranges, the EML may have good light emitting ability without a substantial increase in driving voltage.

Next, the electron transport region may be disposed on the EML.

The electron transport region may include at least one of a HBL, an ETL, and an EIL.

In an implementation, the electron transport region may have a structure including an ETL, an ETL/EIL, or a HBL/ETL/EIL, wherein the layers forming a structure of the electron transport region may be sequentially stacked on the EML in the order stated above.

In an implementation, the organic layer 150 of the organic light-emitting device 10 may include the electron transport region between the EML and the second electrode 190.

The electron transport region may include a HBL. When the EML includes a phosphorescent dopant, the HBL may prevent diffusion of triplet exitons or holes into the ETL from the EML.

When the electron transport region includes a HBL, the HBL may be formed on the EML by using any of a variety of methods, for example, by using vacuum deposition, spin coating, casting, Langmuir-Blodgett (LB) deposition, inkjet printing, laser printing, laser induced thermal imaging (LITI), or the like. When the HBL is formed using vacuum deposition or spin coating, the deposition and coating conditions for forming the HBL may be similar to the above-described deposition and coating conditions for forming the HIL, and accordingly will not be described in detail.

For example, the HBL may include at least one of BCP below and Bphen, below.

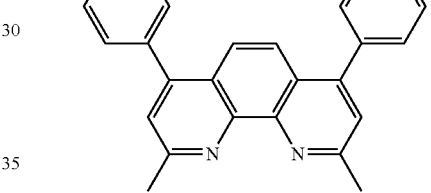

BCP

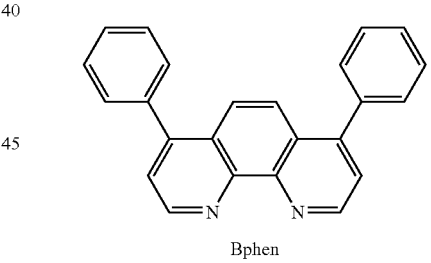

Bphen

A thickness of the HBL may be from about 20 Å to about 1,000 Å, e.g., about 30 Å to about 300 Å. When the thickness of the HBL is within these ranges, the HBL may have improved hole blocking ability without a substantial increase in driving voltage.

The electron transport region may include an ETL. The ETL may be formed on the EML or the HBL by using any of a variety of methods, for example, by using vacuum deposition, spin coating, casting, Langmuir-Blodgett (LB) deposition, inkjet printing, laser printing, laser induced thermal imaging (LITI), or the like. When the ETL is formed using vacuum deposition or spin coating, the deposition and coating conditions for forming the ETL may be similar to the above-described deposition and coating conditions for forming the HIL, and accordingly will not be described in detail.

The ETL may further include at least one of Alq₃, Balq, TAZ, and NTAZ below, in addition to BCP and Bphen described above.

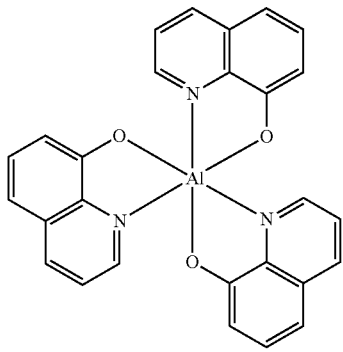

Alq3

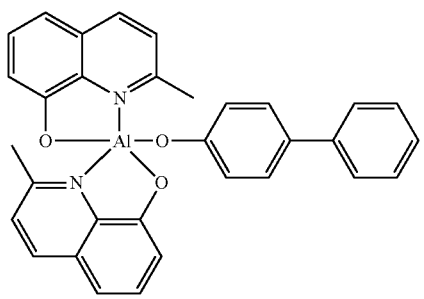

BAlq

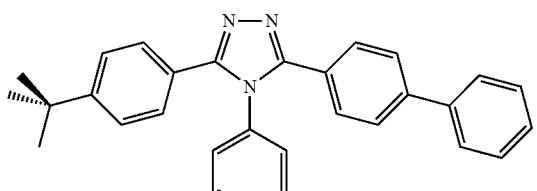

TAZ

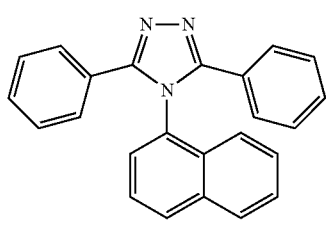

NTAZ

In an implementation, the ETL may further include, at least one of compounds represented by Formula 601 below, in addition to the condensed cyclic compound represented by Formula 1.

$$AR_{601}-[(L_{601})_{xe1}-E_{601}]_{xe2} \quad \text{<Formula 601>}$$

In Formula 601, $AR_{601}$ may be defined as described in conjunction with $AR_{301}$ in Formula 301, $L_{601}$ may be defined as described above in conjunction with $L_{201}$ in Formula 301, $E_{601}$ may be selected from:

a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, or a dibenzocarbazolyl group; or a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, or a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a slat thereof, a phosphoric acid group or a salt thereof, a $C_1$-$C_{20}$ alkyl group, a $C_1$-$C_{20}$ alkoxy group, a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, and a dibenzothiophenyl group, xe1 may be selected from 0, 1, 2, and 3, and xe2 may be selected from 1, 2, 3, and 4.

In an implementation, the electron transport layer may include at least one of compounds represented by Formula 602:

<Formula 602>

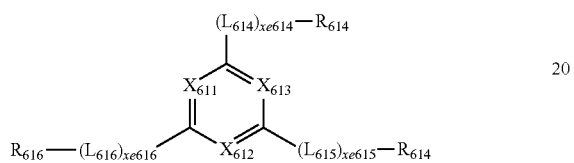

In Formula 602, $X_{611}$ may be N or C-$(L_{611})_{xe611}$-$R_{611}$, $X_{612}$ may be N or C-$(L_{612})_{xe612}$-$R_{612}$, $X_{613}$ may be N or C-$(L_{613})_{xe613}$-$R_{613}$, at least one of $X_{611}$ to $X_{613}$ may be N, $L_{611}$ to $L_{616}$ may be each independently defined as described above in conjunction $L_{201}$ in other formulae herein, $R_{611}$ to $R_{616}$ may be each independently:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, and xe611 to xe616 may be each independently selected from, 0, 1, 2, and 3.

The compound represented by Formula 601 and the compound represented by Formula 602 may include at least one of Compounds ET1 to ET15 illustrated below.

ET1

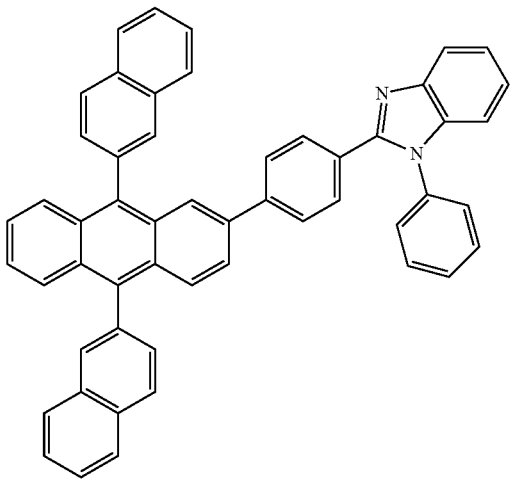

ET2

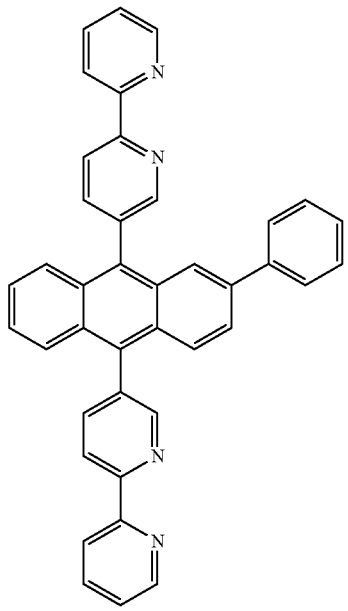

ET3

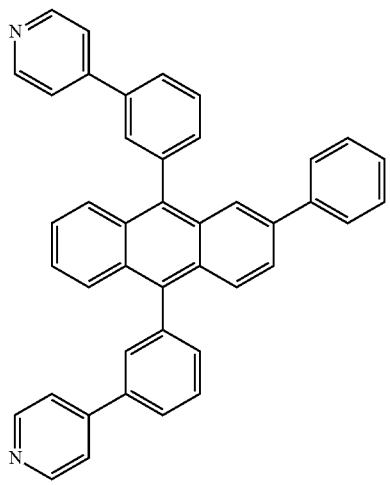

ET4
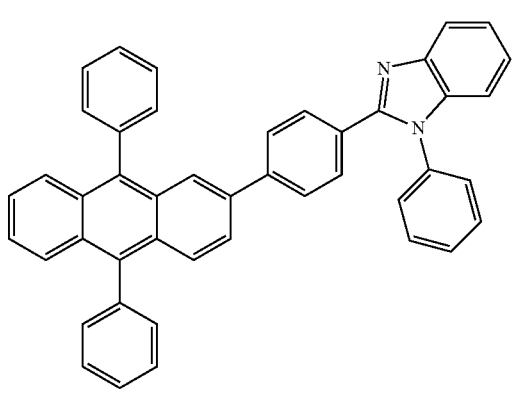
ET7
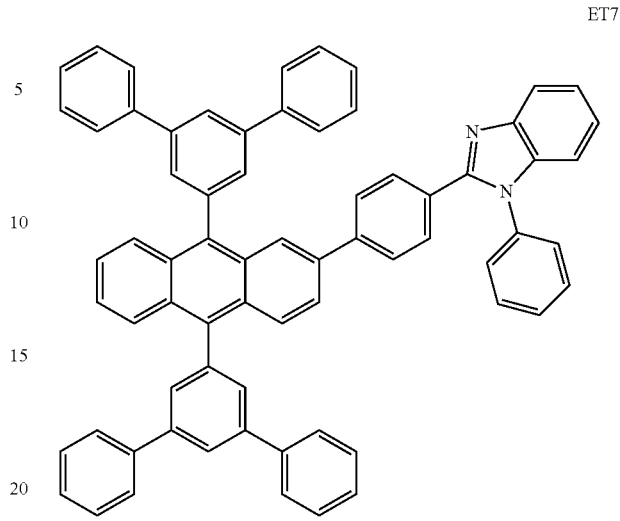
ET5
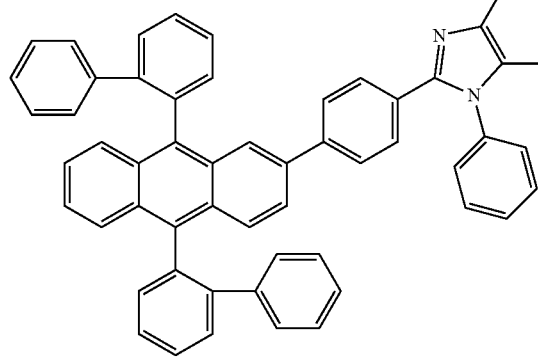
ET8
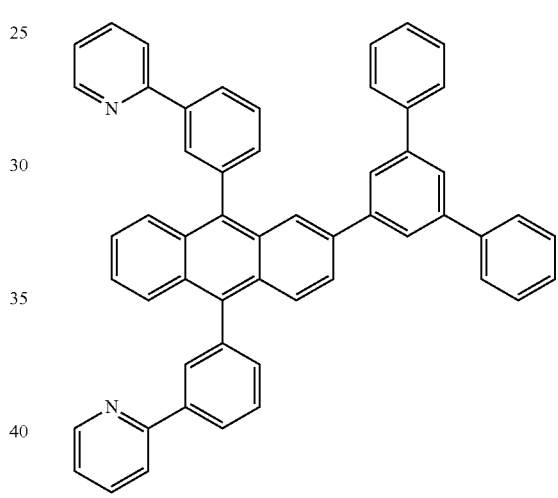
ET6
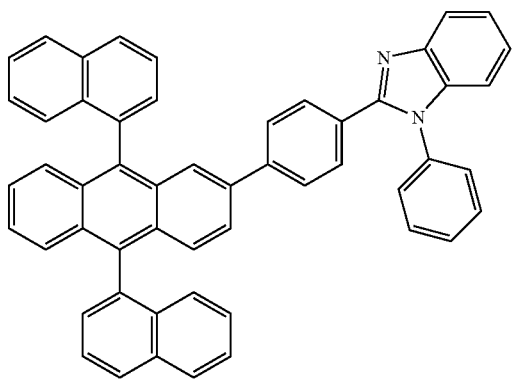
ET9
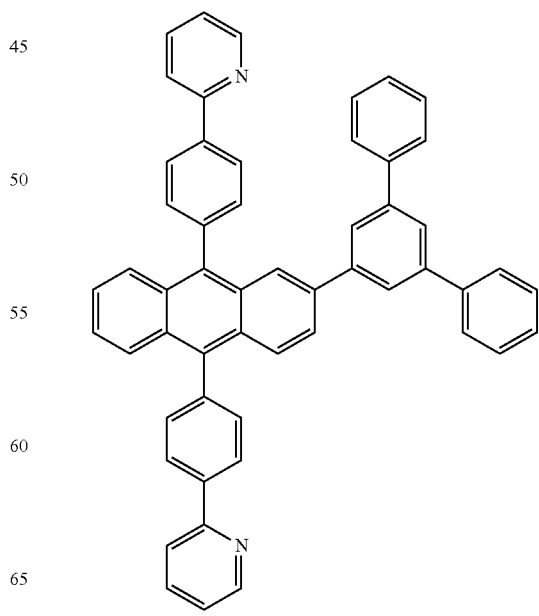

ET10

ET11

ET12

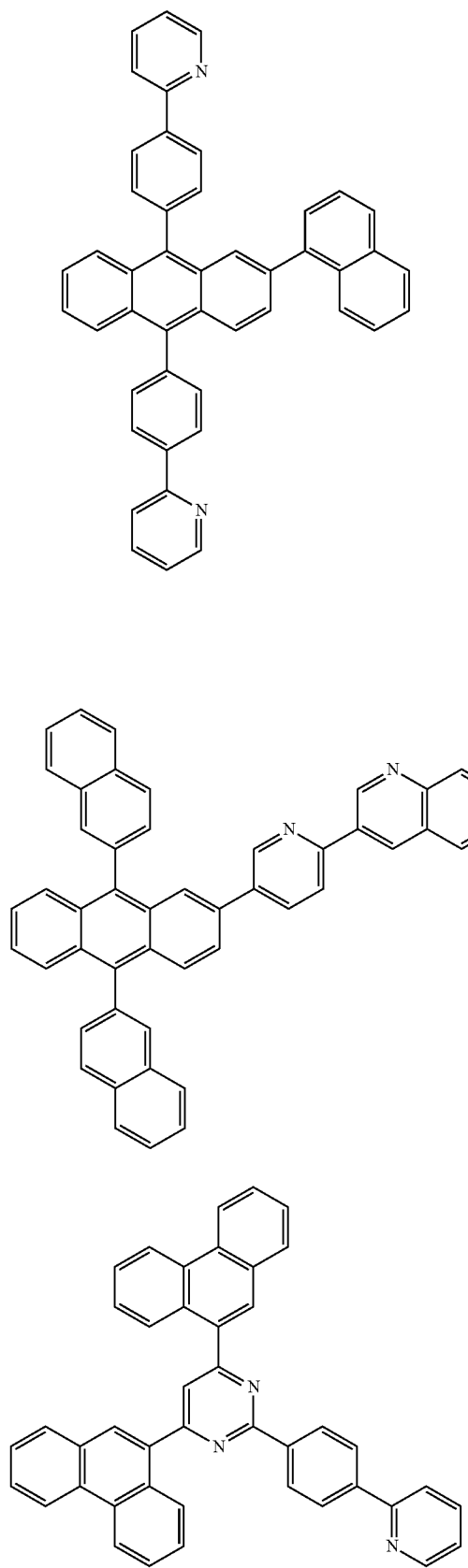

ET13

ET14

ET15

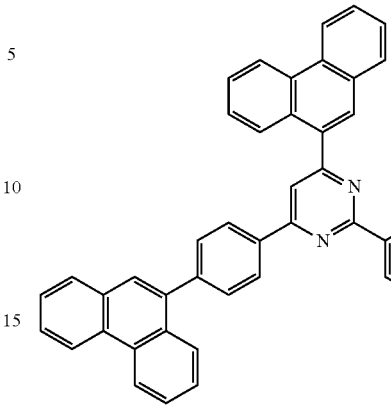

A thickness of the ETL may be from about 100 Å to about 1,000 Å, e.g., about 150 Å to about 500 Å. When the thickness of the ETL is within these ranges, the ETL may have satisfactory electron transporting ability without a substantial increase in driving voltage.

In an implementation, the ETL may further include a metal-containing material, in addition to the above-described materials.

The metal-containing material may include a lithium (Li) complex. Non-limiting examples of the Li complex may include compound ET-D1 below (lithium quinolate (LiQ)), or compound ET-D2 below.

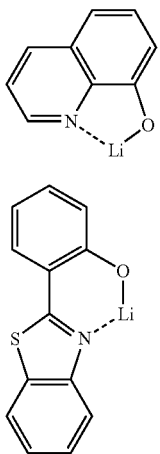

ET-D1

ET-D2

The electron transport region may include an EIL that may facilitate injection of electrons from the second electrode 190.

The EIL may be formed on the ETL by using any of a variety of methods, e.g., by using vacuum deposition, spin coating, casting, Langmuir-Blodgett (LB) deposition, inkjet printing, laser printing, laser induced thermal imaging (LITI), or the like. When the EIL is formed using vacuum deposition or spin coating, the deposition and coating conditions for forming the EIL may be similar to the above-described deposition and coating conditions for forming the HIL, and accordingly will not be described in detail.

The EIL may include at least one selected from LiF, NaCl, CsF, $Li_2O$, BaO, and LiQ.

A thickness of the EIL may be from about 1 Å to about 100 Å, e.g., about 3 Å to about 90 Å. When the thickness of the EIL is within these ranges, the EIL may have satisfactory electron injection ability without a substantial increase in driving voltage.

The second electrode 190 may be disposed on the organic layer 150, as described above. The second electrode 190 may be a cathode as an electron injecting electrode. A material for forming the second electrode 190 may be a metal, an alloy, an electrically conductive compound, which have a low-work function, or a mixture thereof. Non-limiting examples of materials for forming the second electrode 190 may include lithium (Li), magnesium (Mg), aluminum (Al), aluminum-lithium (Al—Li), calcium (Ca), magnesium-indium (Mg—In), and magnesium-silver (Mg—Ag). In some embodiments, a material for forming the second electrode 190 may be ITO or IZO. The second electrode 190 may be a reflective electrode, a semi-transmissive electrode, or a transmissive electrode.

As used herein, a $C_1$-$C_{60}$ alkyl group refers to a linear or branched aliphatic hydrocarbon monovalent group having 1 to 60 carbon atoms. Non-limiting examples of the $C_1$-$C_{60}$ alkyl group a methyl group, a ethyl group, a propyl group, an isobutyl group, a sec-butyl group, a tert-butyl group, a pentyl group, an iso-amyl group, and a hexyl group. A $C_1$-$C_{60}$ alkylene group refers to a divalent group having the same structure as the $C_1$-$C_{60}$ alkyl.

As used herein, a $C_1$-$C_{60}$ alkoxy group refers to a monovalent group represented by —$OA_{101}$ (where $A_{101}$ is a $C_1$-$C_{60}$ alkyl group as described above. Non-limiting examples of the $C_1$-$C_{60}$ alkoxy group as described above.

Non-limiting examples of the $C_1$-$C_{60}$ alkoxy group are a methoxy group, an ethoxy group, and an isopropyloxy 3.

As used herein, a $C_2$-$C_{60}$ alkenyl group refers to a structure including at least one carbon double bond in the middle or terminal of the $C_2$-$C_{60}$ alkyl group. Non-limiting examples of the $C_2$-$C_{60}$ alkenyl group are an ethenyl group, a propenyl group, and a butenyl group. A $C_2$-$C_{60}$ alkylene group refers to a divalent group having the same structure as the $C_2$-$C_{60}$ alkenyl group.

As used herein, a $C_2$-$C_{60}$ alkynyl group refers to a structure including at least one carbon triple bond in the middle or terminal of the $C_2$-$C_{60}$ alkyl group. Non-limiting examples of the $C_2$-$C_{60}$ alkynyl group are an ethynyl group and a propynyl group. A $C_2$-$C_{60}$ alkynylene group used herein refers to a divalent group having the same structure as the $C_2$-$C_{60}$ alkynyl group.

As used herein, a $C_3$-$C_{10}$ cycloalkyl group refers to a monovalent, monocyclic hydrocarbon group having 3 to 10 carbon atoms. Non-limiting examples of the $C_3$-$C_{10}$ cycloalkyl group are a cyclopropyl group, a cyclobutyl group, a cyclopentyl group, a cyclohexyl group, and a cycloheptyl group. A $C_3$-$C_{10}$ cycloalkylene group refers to a divalent group having the same structure as the $C_3$-$C_{10}$ cycloalkyl group.

As used herein, a $C_2$-$C_{10}$ heterocycloalkyl group refers to a monovalent monocyclic group having 2 to 10 carbon atoms in which at least one hetero atom selected from N, O, P, and S is included as a ring-forming atom. Non-limiting examples of the $C_2$-$C_{10}$ heterocycloalkyl group are a tetrahydrofuranyl group and a tetrahydrothiophenyl group. A $C_2$-$C_{10}$ heterocycloalkylene group refers to a divalent group having the same structure as the $C_2$-$C_{10}$ heterocycloalkyl group.

As used herein, a $C_3$-$C_{10}$ cycloalkenyl group refers to a monovalent monocyclic group having 3 to 10 carbon atoms that includes at least one double bond in the ring but does not have aromacity. Non-limiting examples of the $C_3$-$C_{10}$ cycloalkenyl group are a cyclopentenyl group, a cyclohexenyl group, and a cycloheptenyl group. A $C_3$-$C_{10}$ cycloalkenylene group refers to a divalent group having the same structure as the $C_3$-$C_{10}$ cycloalkenyl group.

As used herein, a $C_2$-$C_{10}$ heterocycloalkenyl group used herein refers to a monovalent monocyclic group having 2 to 10 carbon atoms that includes at least one double bond in the ring and in which at leas tone hetero atom selected from, N, O, P, and S is included as a ring-forming atom. Non-limiting examples of the $C_2$-$C_{10}$ heterocycloalkenyl group are a 2,3-hydrofuranyl group and a 2,3-hydrothiophenyl group. A $C_2$-$C_{10}$ heterocycloalkenylene group used herein refers to a divalent group having the same structure as the $C_3$-$C_{10}$ heterocycloalkenyl group.

As used herein, a $C_6$-$C_{60}$ aryl group refers to a monovalent, aromatic carbocyclic aromatic group having 6 to 6 carbon atoms, and a $C_6$-$C_{60}$ arylene group refers to a divalent, aromatic carbocyclic group having 6 to 60 carbon atoms. Non-limiting examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group include at least two rings, the rings may be fused to each other.

As used herein, a $C_2$-$C_{60}$ heteroaryl group refers to a monovalent, aromatic carbocyclic aromatic group having 2 to 60 carbon atoms in which at least one hetero atom selected from N, O, P, and S is included as a ring-forming atom, and 2 to 60 carbon atoms. A $C_2$-$C_{60}$ heteroarylene group refers to a divalent, aromatic carbocyclic group having 2 to 60 carbon atoms in which at least one hetero atom selected from N, O, P, and S is included as a ring-forming atom. Non-limiting examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl and the $C_2$-$C_{60}$ heteroarylene include at least two rings, the rings may be fused to each other.

As used herein, a $C_6$-$C_{60}$ aryloxy group indicates —$OA_{102}$ (where $A_{102}$ is a $C_6$-$C_{60}$ aryl group as described above), and a $C_6$-$C_{60}$ arylthio group indicates —$SA_{103}$ (wherein $A_{103}$ is a $C_6$-$C_{60}$ aryl group as described above).

As used herein, a monovalent non-aromatic condensed polycyclic group refers to a monovalent group having at least two rings condensed to each other, in which only carbon atoms (for example, 8 to 60 carbon atoms) are exclusively included as ring-forming atoms and the entire molecule has non-aromaticity. A non-limiting example of the monovalent non-aromatic condensed polycyclic group is a fluorenyl group. A divalent non-aromatic condensed polycyclic group refers to a divalent group having the same structure as the monovalent non-aromatic condensed polycyclic group.

As used herein, a monovalent non-aromatic condensed heteropolycyclic group refers to a monovalent group having at least two rings condensed to each other, in which carbon atoms (for example, 2 to 60 carbon atoms) and a hetero atom selected from N, O, P, and S are as ring-forming atoms and the entire molecule has non-aromaticity. A non-limiting example of the monovalent non-aromatic condensed heteropolycyclic group is a carbazolyl group. A divalent non-aromatic condensed heteropolycyclic group refers to a divalent group having the same structure as the monovalent non-aromatic condensed heteropolycyclic group.

As used herein, at least one of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed cyclic group, the substituted divalent non-aromatic hetero-condensed cyclic group, the substituted $C_3$-$C_{10}$ cyclo alkyl group, the substituted $C_2$-$C_{10}$ heterocyclo alkyl group, the substituted $C_3$-$C_{10}$ cyclo alkenyl group, the substituted $C_2$-$C_{10}$ heterocyclo alkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, the substituted monovalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, and the substituted $C_1$-$C_{60}$ alkoxy group may be selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a cyclopentenyl group, a cyclohexyl group, a cyclopeptyl, a cyclopentenyl, a cyclohelptenyl, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an obarenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, —$N(Q_{11})(Q_{12})$, —$Si(Q_{13})(Q_{14})(Q_{15})$, and —$B(Q_{16})(Q_{17})$;

a cyclopentenyl group, a cyclohexyl group, a cyclopeptyl, a cyclopentenyl, a cycloheptenyl, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an obarenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group;

a cyclopentenyl group, a cyclohexyl group, a cyclopeptyl, a cyclopentenyl, a cycloheptenyl, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an obarenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentenyl group, a cyclohexyl group, a cyclopeptyl, a cyclopentenyl, a cycloheptenyl, phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an obarenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group.

The acronym "Ph" used herein refers to phenyl, the acronym "Me" used herein refers to methyl, the acronym "Et" used herein refers to ethyl, and the acronym "ter-Bu" or "Bu$^t$" used herein refers to tert-butyl.

One or more embodiments, which may include condensed cyclic compounds, and organic light-emitting devices including the same, will now be described in detail with reference to the following examples. In the following synthesis example, the expression that "'B' instead of 'A' was used" means that the amounts of 'B' and 'A' were the same in equivalent amounts.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Example 1: Synthesis of Compound 5

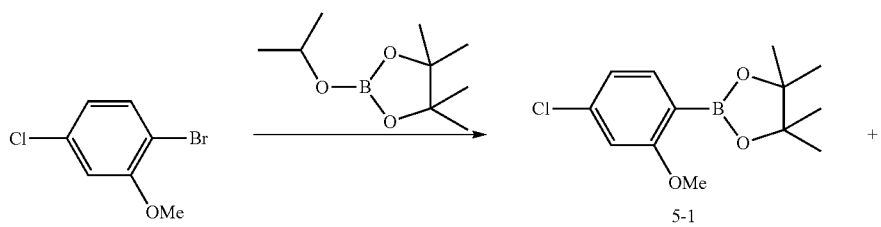

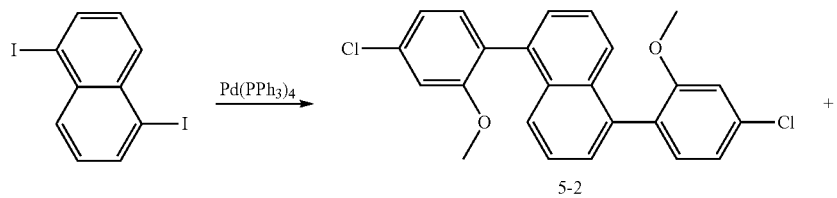

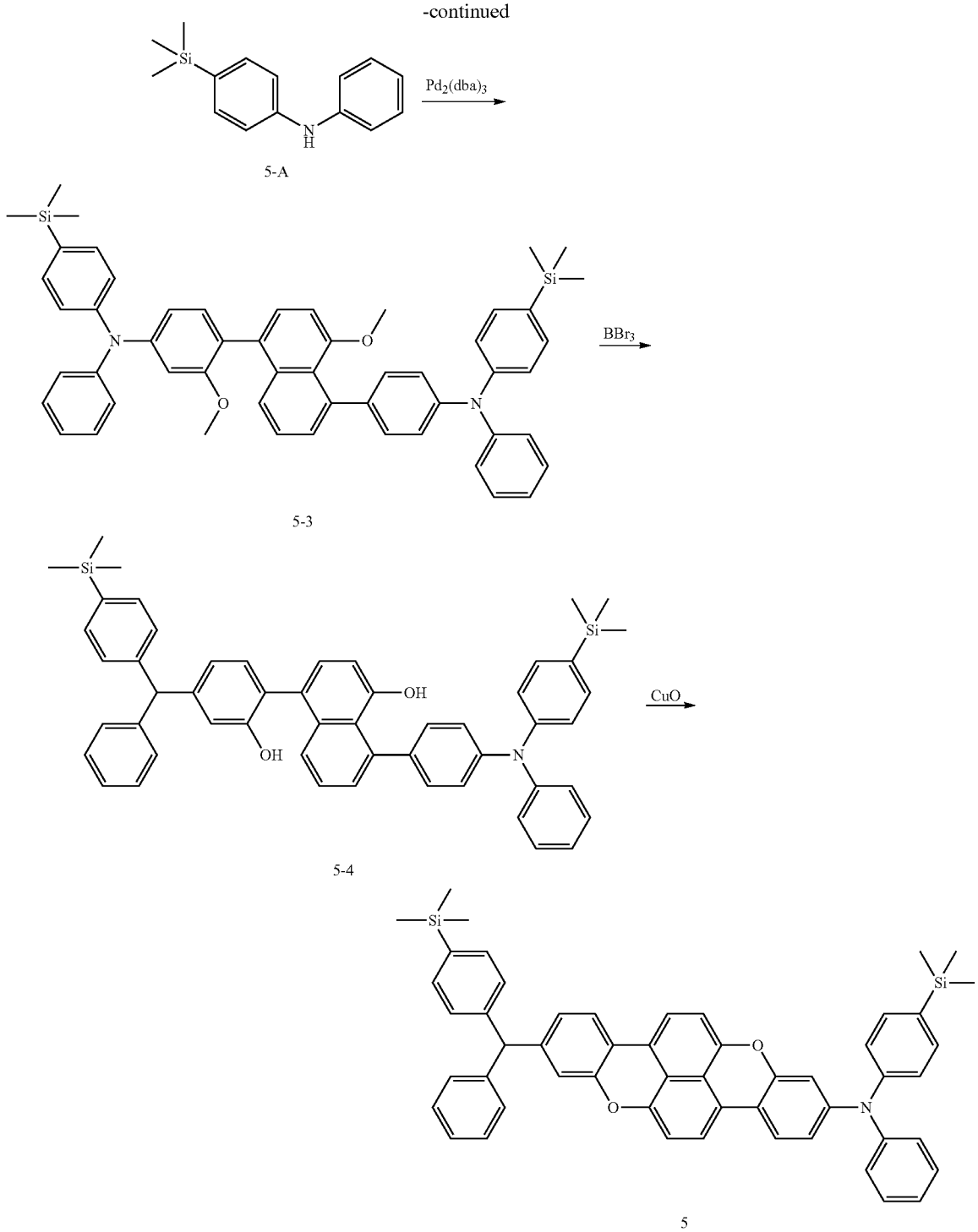

Synthesis of Intermediate 5-1

5.2 g of 2-bromo-5-chlorodimethylfluorene (23.6 mmol) was dissolved in 100 mL of tetrahydrofurane (THF), and 10 mL of normal butyl lithium (25.0 mmol, 2.5 M in hexane) was slowly dropwise added thereto at added thereto −78° C. After the reaction solution was stirred at the same temperature for about 1 hour, 9.3 mL (50.0 mmol) of 2-isoproxy-4,4,5,5,-tetramethyl-1,3,2-dioxaborolane was slowly dropwise added to the reaction solution, which was then stirred at about −78° C. for about 1 hour, and further at room or ambient temperature for about 24 hours. After the reaction was completed, 50 mL of a 10% HCl aqueous solution and 50 mL of H$_2$O were added thereto, followed by extracting three times with 80 mL of diethyl ether. An organic layer was collected, and was dried using magnesium sulfate to evaporate the solvent. The residue was separated and purified using silica get column chromatography to obtain 5.83 g of Intermediate 5-1 (Yield: 92%). This compound was identified using liquid chromatography-mass spectroscopy (LC-MS).

$C_{13}H_{18}BClO_3$: M+ 268.1

Synthesis of Intermediate 5-2

5.90 g (22.0 mmol) of Intermediate 1-6, 4.18 g (11.0 mmol) of 1,4-(4-bromophenyl)-1-phenyl-1-benzoimidazole, 2.54 g (2.2 mmol) of tetrakis(triphenylphosphine)palladium (Pd(PPh$_3$)$_4$), and 9.00 g (66 mmol) of K$_2$CO$_3$ were dissolved in 40 mL of a mixed tetrahydrofuran (THF) and H$_2$O (2:1 by volume) solution to obtain a solution, which was then stirred at about 70° C. for about 5 hours. The reaction solution was cooled down to ambient temperature, and 60 mL of water was added thereto, followed by extracting three times with 60 mL of ethyl ether. The organic phase was collected, and was dried using magnesium sulfate to evaporate the solvent. The residue was separated and purified using silica gel column chromatography to obtain 3.42 g of Intermediate 5-2 (Yield: 76%). This compound was identified using liquid chromatography-mass spectroscopy (LC-MS).

$C_{24}H_{18}Cl_2O_2$: M+ 408.1

Synthesis of Intermediate 5-3

8.18 g (20.0 mmol) of Intermediate 5-2, 9.66 g (40.0 mmol) of Intermediate 5-A, 0.37 g (0.4 mmol) of Pd$_2$(dba)$_3$, 0.08 g (0.4 mmol) of PtBu$_3$, and 5.76 g (60.0 mmol) of KOtBu were dissolved in 90 mL of toluene to obtain a mixture, which was then stirred at about 85° C. for 4 hours. The reaction solution was cooled down to ambient temperature, followed by extracting three times with 50 mL of water and 50 mL of diethyl ether. The organic phase was collected, and was dried using magnesium sulfate to evaporate the solvent. The residue was separated and purified using silica gel column chromatography to obtain 13.6 g of Intermediate 5-3 (Yield: 83%). This compound was identified using LC-MS.

$C_{54}H_{54}N_2O_2Si_2$ M+ 818.4

Synthesis of Intermediate 5-4

1.64 g (2.00 mmol) of Intermediate 5-3 was dissolved in 10 mL of methyl chloroform (MC) to obtain a reaction solution, and 0.33 mL (3.5 mmol) of BBR$_3$ was slowly dropwise added thereto at about −78° C. After raising the temperature of the reaction solution to ambient temperature, the reaction solution was stirred at ambient temperature for about 24 hours. After the reaction was completed, 5 mL of MeOH and 10 mL of H$_2$O were added thereto, followed by extracting three times with 10 mL of MC. The organic phase was collected, and was dried using magnesium sulfate to evaporate the solvent. The residue was separated and purified using silica gel column chromatography to obtain 1.19 g of Intermediate 5-4 (Yield: 75%). This compound was identified using LC-MS.

$C_{52}H_{50}N_2O_2Si_2$: M+ 790.3

Synthesis of Compound 5

1.58 g (2.00 mmol) of Intermediate 5-4 was dissolved in 10 mL of dimethylformamide (DMF), and 0.48 g (6.0 mmol) of CuO was dropwise added thereto at ambient temperature. The reaction mixture was stirred at about 140° C. for about 48 hours. After the reaction was completed, the reaction product was filtered using Celite to obtain an organic layer. 10 mL of H$_2$O was added to the organic layer, followed by extracting three times with 10 mL of ethyl acetate. The resulting organic layer was collected and was dried using magnesium sulfate to evaporate the solvent. The residue was separated and purified using silica gel column chromatography to obtain 1.04 g of Compound 5 (Yield: 66%). This compound was identified using liquid chromatography-mass spectroscopy (LC-MS) and nuclear magnetic resonance (NMR).

C52H46N2O2Si2: M+ found 786.32, calc. 786.31.

Synthesis Example 2: Synthesis of Compound 23

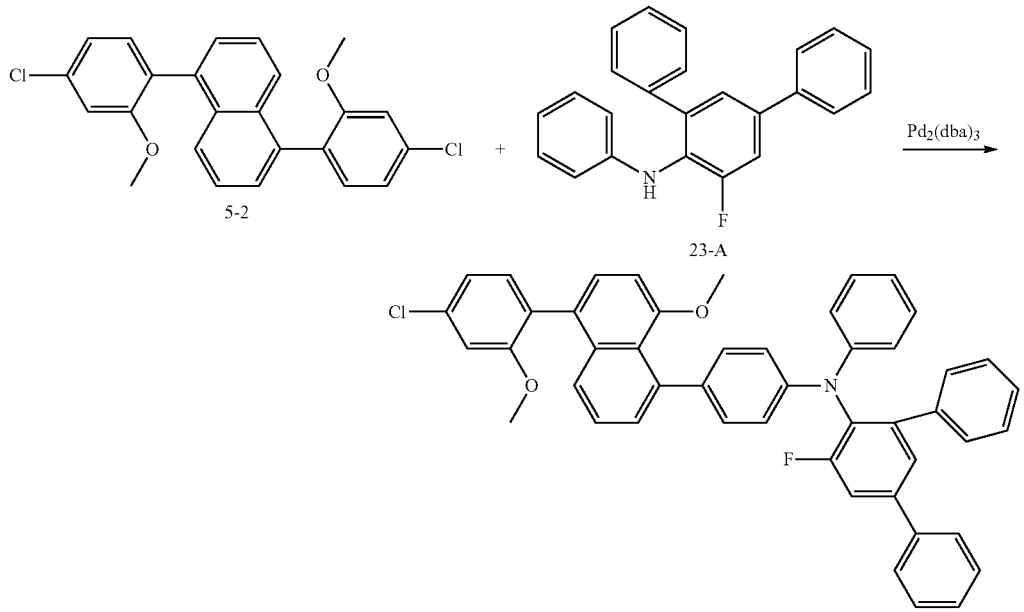

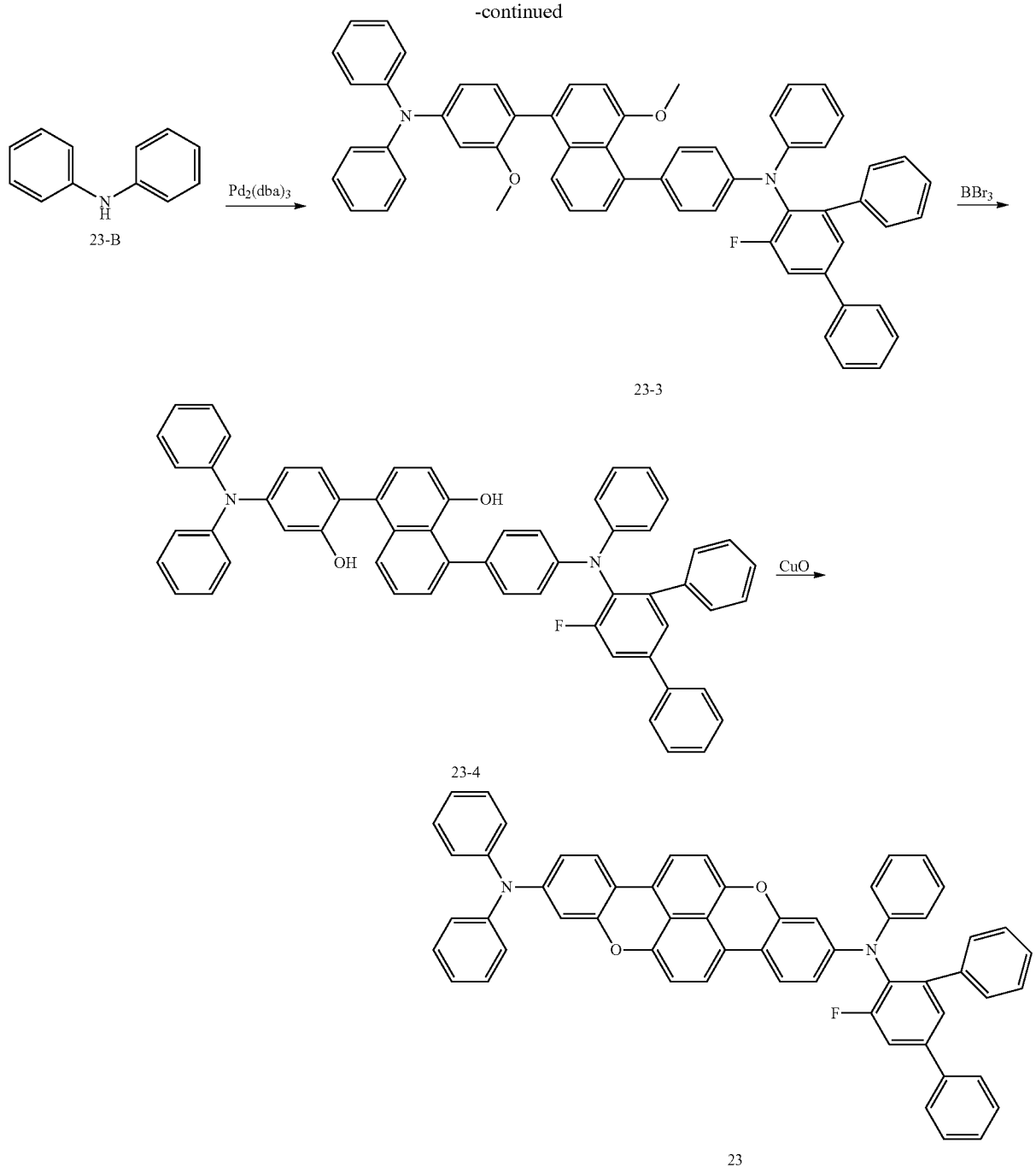

Synthesis of Intermediate 23-3

Intermediate 23-3(1) was obtained in the same manner as in the synthesis of Intermediate 5-3 in Synthesis Example 1, except that Intermediate 23-A (20.0 mmol) instead of Intermediate 5-A (40.0 mmol) was used.

Synthesis of Intermediate 23-3

Intermediate 23-3 was obtained in the same manner as in the synthesis of Intermediate 5-3 in Synthesis Example 1, except that Intermediate 23-3(1) (20.0 mmol) and Intermediate 23-B (20.0 mmol) instead of Intermediate 5-2 (20.0 mmol) and Intermediate 5-A (40.0 mmol) was used.

Synthesis of Intermediate 23-4

Intermediate 23-4 was obtained in the same manner as in the same manner as in the synthesis of Intermediate 5-4 in Synthesis Example 1, except that Intermediate 23-3 instead of Intermediate 5-3 was used.

Synthesis of Compound 23

2.30 g of Compound 23 (Yield 71%) was synthesized in the same manner as in the synthesis of Compound 5 in Synthesis Example 1, except that Intermediate 23-4 instead of Intermediate 5-4 was used. This compound was identified using LC-MS and NMR.

$C_{58}H_{37}FN_2O_2$: $M^+$ found 848.39, Calc. 848.36

Synthesis Example 3: Synthesis of Compound 25

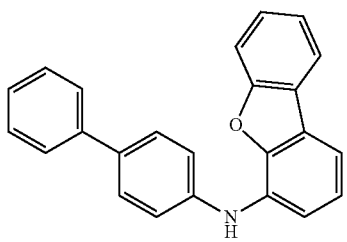

25-A 3.5 g of Compound 25 (Yield 68%) was synthesized in the same manner as in Synthesis Example 2, except that Intermediate 25-A instead of Intermediate 23-A was used. This compound was identified using LC-MS and NMR.
C58H36N2O3: M+ found 808.27, Calc. 808.27

Synthesis Example 4: Synthesis of Compound 31

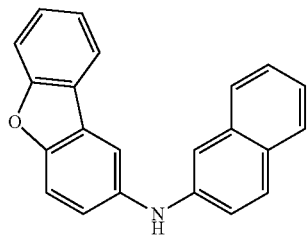

31-A 2.2 g of Compound 31 (Yield 65%) was synthesized in the same manner as in Synthesis Example 2, except that Intermediate 31-A instead of Intermediate 23-A was used. This compound was identified using LC-MS and NMR.

$C_{56}H_{34}N_2O_3$: M$^+$ found 782.27, Calc. 782.26

Synthesis Example 5: Synthesis of Compound 50

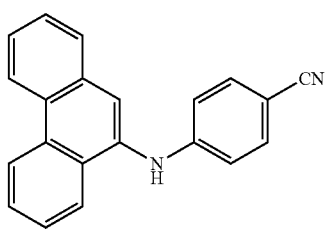

50-A 3.2 g of Compound 50 (Yield 70%) was synthesized in the same manner as in Synthesis Example 2, except that Intermediate 50-An instead of Intermediate 23-A was used. This compound was identified using LC-MS and NMR.

C55H33N3O2: M+ found 767.26, Calc. 767.26

Synthesis Example 6: Synthesis of Compound 63

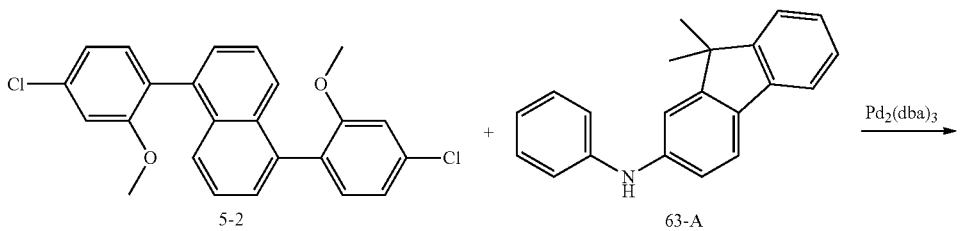

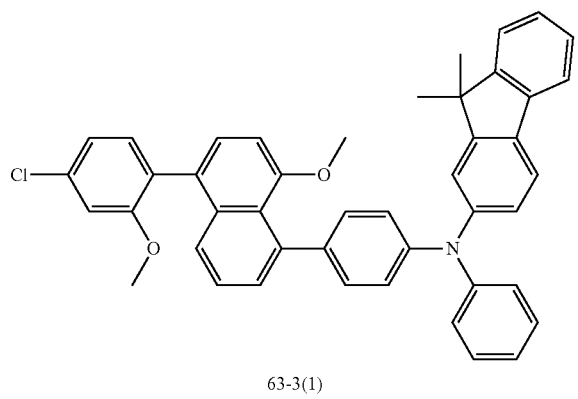

63-3(1)

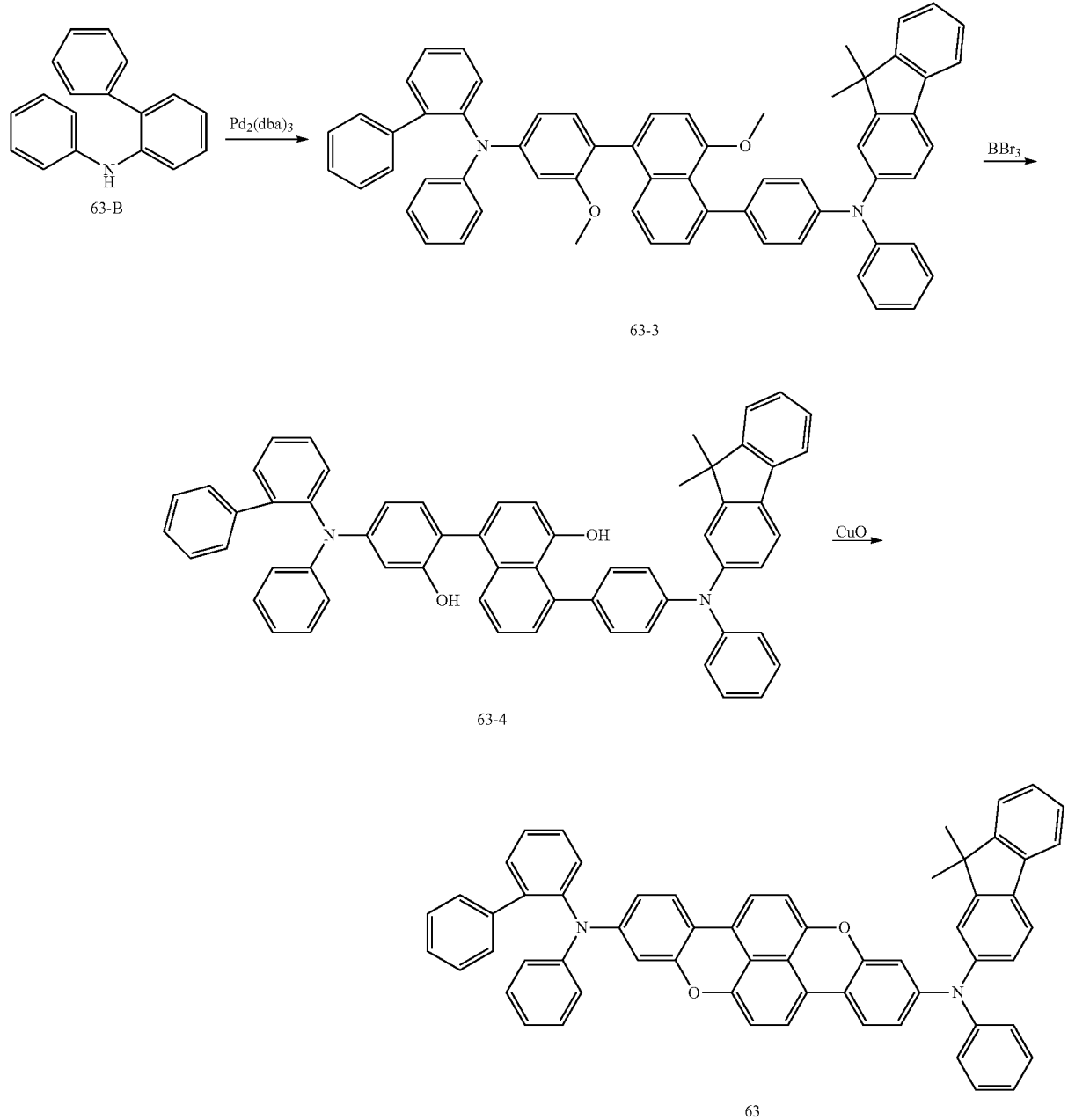

Synthesis of Intermediate 63-3(1)

Intermediate 63-3(1) was obtained in the same manner as in the synthesis of Intermediate 5-3 in Synthesis Example 1, except that Intermediate 63-A (20.0 mmol) instead of Intermediate 5-A (40.0 mmol) was used.

Synthesis of Intermediate 63-3

Intermediate 63-3 was obtained in the same manner as in the synthesis of Intermediate 5-3 in Synthesis Example 1, except that Intermediate 63-3(1) (20.0 mmol) and Intermediate 63-B (20.0 mmol) instead of Intermediate 5-2 (20.0 mmol) and Intermediate 5-A (40.0 mmol) were used.

Synthesis of Intermediate 63-4

Intermediate 63-4 was obtained in the same manner as in the same manner as in the synthesis of Intermediate 5-4 in Synthesis Example 1, except that Intermediate 63-3 instead of Intermediate 5-3 was used.

Synthesis of Intermediate 63

2.6 g of Compound 63 (Yield 75%) was synthesized in the same manner as in the synthesis of Compound 5 in Synthesis Example 1, except that Intermediate 63-4 instead of Intermediate 5-4 was used. This compound was identified using LC-MS and nuclear magnetic resonance (NMR).

$C_{61}H_{42}N_2O_2$: M⁺ found 834.33, Calc. 834.32

Synthesis Example 7: Synthesis of Compound 70

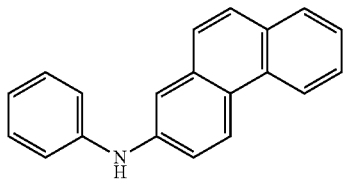

70-A 1.9 g of Compound 70 (Yield 61%) was synthesized in the same manner as in Synthesis Example 6, except that Intermediate 70-A instead of Intermediate 63-A was used. This compound was identified using LC-MS and nuclear magnetic resonance (NMR).

$C_{60}H_{38}N_2O_2$: $M^+$ found 818.30, Calc. 818.29

Synthesis Example 8: Synthesis of Compound 73

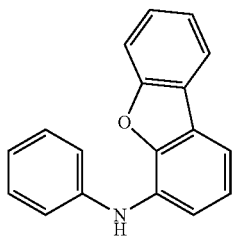

73-B 2.3 g of Compound 73 (Yield 73%) was synthesized in the same manner as in Synthesis Example 6, except that Intermediate 73-B instead of Intermediate 63-B was used.

C61H40N2O3: M+ found 848.31, Calc. 848.30

Synthesis Example 9: Synthesis of Compound 91

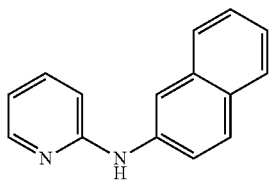

91-A 1.8 g of Compound 91 (Yield 60%) was synthesized in the same manner as in Synthesis Example 6, except that Intermediate 91-A instead of Intermediate 63-A was used. This compound was identified using LC-MS and nuclear magnetic resonance (NMR).

$C_{55}H_{35}N_3O_2$: $M^+$ found 769.28, Calc. 769.27

Synthesis Example 10: Synthesis of Compound 1

2.6 g of Compound 1 (Yield 65%) was synthesized in the same manner as in Synthesis Example 1, except that Intermediate 23-B of Synthesis Example 2 instead of Intermediate 5-A was used to synthesize Intermediate 5-3. This compound was identified using LC-MS and nuclear magnetic resonance (NMR).

Synthesis Example 11: Synthesis of Compound 7

2.8 g of Compound 7 (Yield 66%) was synthesized in the same manner as in Synthesis Example 1, except that Intermediate 63-B of Synthesis Example 6 instead of Intermediate 5-A was used to synthesize Intermediate 5-3. This compound was identified using LC-MS and nuclear magnetic resonance (NMR).

Synthesis Example 12: Synthesis of Compound 11

2.5 g of Compound 11 (Yield 71%) was synthesized in the same manner as in Synthesis Example 1, except that Intermediate 73-B of Synthesis Example 6 instead of Intermediate 5-A was used to synthesize Intermediate 5-3. This compound was identified using LC-MS and nuclear magnetic resonance (NMR).

Synthesis Example 13: Synthesis of Compound 14

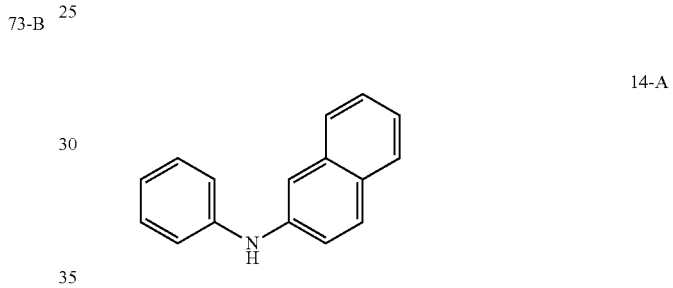

14-A 3.0 g of Compound 14 (Yield 70%) was synthesized in the same manner as in Synthesis Example 1, except that Intermediate 14-A instead of Intermediate 5-A was used to synthesize Intermediate 5-3. This compound was identified using LC-MS and nuclear magnetic resonance (NMR).

Synthesis Example 14: Synthesis of Compound 24

3.2 g of Compound 24 (Yield 72%) was synthesized in the same manner as in Synthesis Example 3, except that Intermediate 73-B of Synthesis Example 8 instead of Intermediate 23-A was used to synthesize Intermediate 23-3(1). This compound was identified using LC-MS and nuclear magnetic resonance (NMR).

Synthesis Example 15: Synthesis of Compound 29

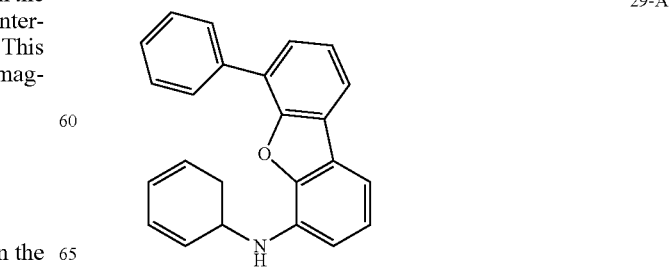

29-A 2.8 g of Compound 29 (Yield 65%) was synthesized in the same manner as in Synthesis Example 2, except that Intermediate 29-A instead of Intermediate 23-A was used to synthesize Intermediate 23-3(1). This compound was identified using LC-MS and nuclear magnetic resonance (NMR).

Synthesis Example 16: Synthesis of Compound 35

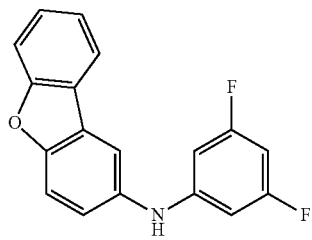

35-A 2.2 g of Compound 35 (Yield 63%) was synthesized in the same manner as in Synthesis Example 2, except that Intermediate 35-A instead of Intermediate 23-A was used to synthesize Intermediate 23-3(1). This compound was identified using LC-MS and nuclear magnetic resonance (NMR).

Synthesis Example 17: Synthesis of Compound 40

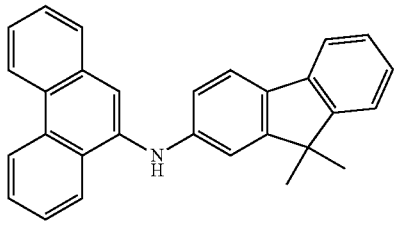

40-A 3.2 g of Compound 40 (Yield 71%) was synthesized in the same manner as in Synthesis Example 2, except that Intermediate 40-A instead of Intermediate 23-A was used to synthesize Intermediate 23-3(1). This compound was identified using LC-MS and nuclear magnetic resonance (NMR).

Synthesis Example 18: Synthesis of Compound 53

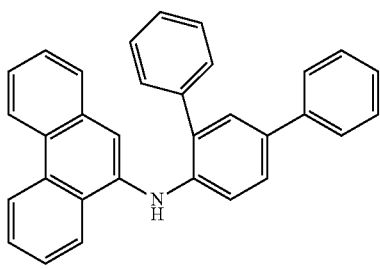

53-A 2.2 g of Compound 53 (Yield 62%) was synthesized in the same manner as in Synthesis Example 2, except that Intermediate 53-A instead of Intermediate 23-A was used to synthesize Intermediate 23-3(1). This compound was identified using LC-MS and nuclear magnetic resonance (NMR).

Synthesis Example 19: Synthesis of Compound 57

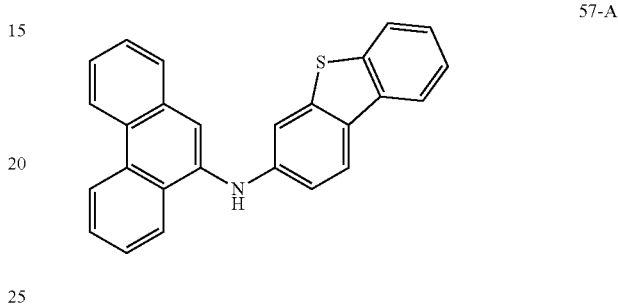

57-A 2.0 g of Compound 57 (Yield 64%) was synthesized in the same manner as in Synthesis Example 2, except that Intermediate 57-A instead of Intermediate 23-A was used to synthesize Intermediate 23-3(1). This compound was identified using LC-MS and nuclear magnetic resonance (NMR).

Synthesis Example 20: Synthesis of Compound 64

2.9 g of Compound 64 (Yield 69%) was synthesized in the same manner as in Synthesis Example 6, except that Intermediate 23-A of Synthesis Example 2 instead of Intermediate 63-A was used. This compound was identified using LC-MS and nuclear magnetic resonance (NMR).

Synthesis Example 21: Synthesis of Compound 65

2.7 g of Compound 65 (Yield 73%) was synthesized in the same manner as in Synthesis Example 6, except that Intermediate 73-B of Synthesis Example 8 instead of Intermediate 63-A was used to synthesize Intermediate 63-3(1). This compound was identified using LC-MS and nuclear magnetic resonance (NMR).

Synthesis Example 22: Synthesis of Compound 69

3.0 g of Compound 69 (Yield 66%) was synthesized in the same manner as in Synthesis Example 6, except that Intermediate 70-A of Synthesis Example 7 instead of Intermediate 63-A was used to synthesize Intermediate 63-3(1). This compound was identified using LC-MS and nuclear magnetic resonance (NMR).

Synthesis Example 23: Synthesis of Compound 78
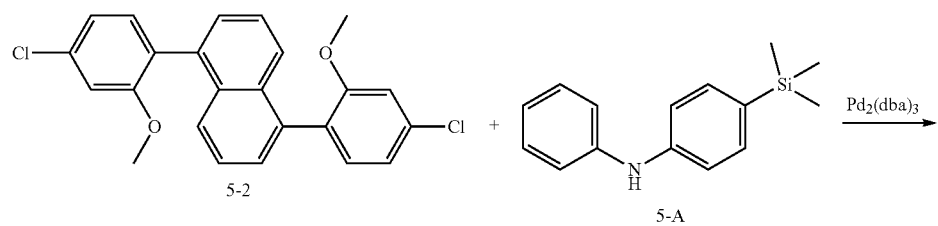
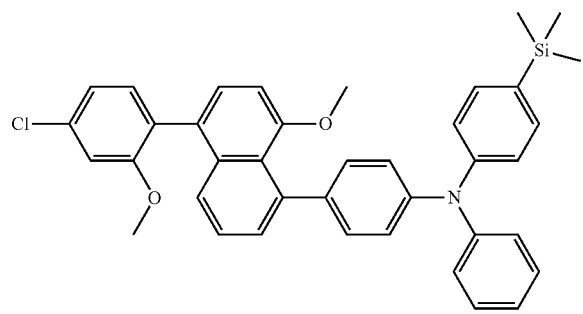
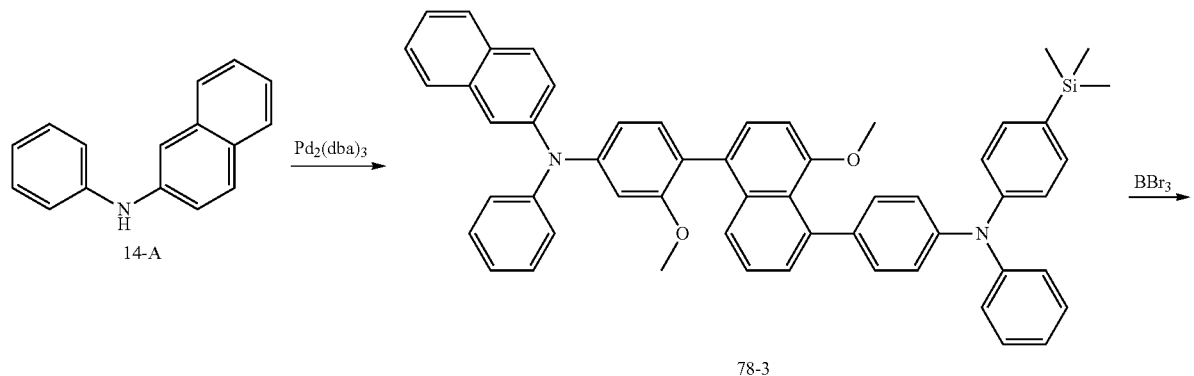
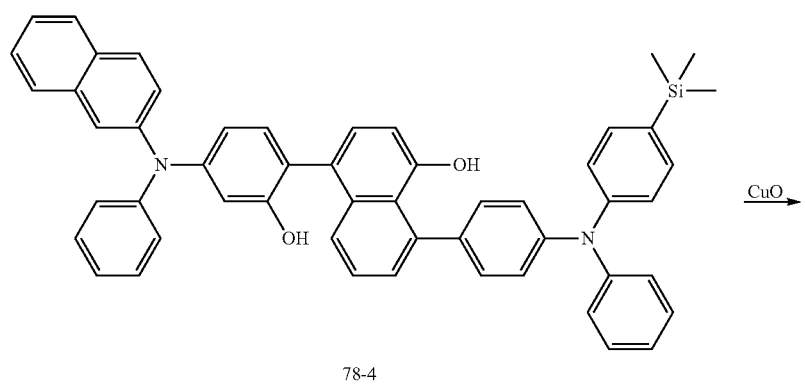

-continued

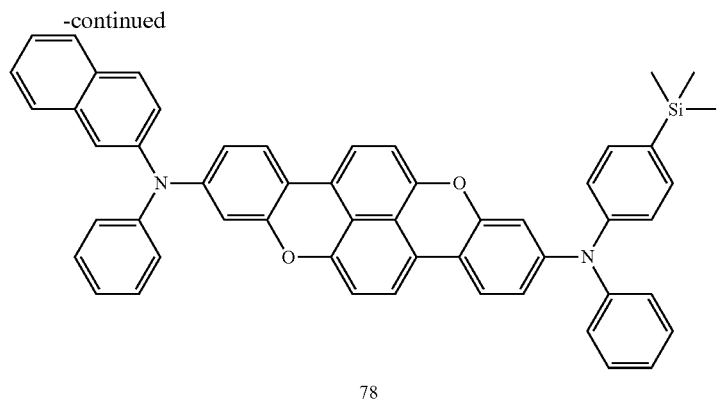

78

Synthesis of Intermediate 78-3(1)

Intermediate 78-3(1) was obtained in the same manner as in the synthesis of Intermediate 5-3 in Synthesis Example 1, except that the amount of Intermediate 5-A was changed from 40.0 to 20.0 mmol.

Synthesis of Intermediate 78-3

Intermediate 78-3 was obtained in the same manner as in the synthesis of Intermediate 5-3 in Synthesis Example 1, except that Intermediate 78-3(1) (20.0 mmol) and Intermediate 14-A (20.0 mmol) instead of Intermediate 5-2 (20.0 mmol) and Intermediate 5-A (40.0 mmol) were used.

Synthesis of Intermediate 78-4

Intermediate 78-4 was obtained in the same manner as in the same manner as in the synthesis of Intermediate 5-4 in Synthesis Example 1, except that Intermediate 78-3 instead of Intermediate 5-3 was used.

Synthesis of Intermediate 78

3.2 g of Compound 78 (Yield 65%) was synthesized in the same manner as in the synthesis of Compound 5 in Synthesis Example 1, except that Intermediate 78-4 instead of Intermediate 5-4 was used. This compound was identified using LC-MS and nuclear magnetic resonance (NMR).

Synthesis Example 24: Synthesis of Compound 82

3.0 g of Compound 82 (Yield 68%) was synthesized in the same manner as in Synthesis Example 23, except that Intermediate 23-A of Synthesis Example 2 instead of Intermediate 5-A was used to synthesize Intermediate 78-3(1). This compound was identified using LC-MS and nuclear magnetic resonance (NMR).

Synthesis Example 25: Synthesis of Compound 85

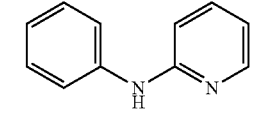

85-A 2.5 g of Compound 85 (Yield 62%) was synthesized in the same manner as in Synthesis Example 1, except that Intermediate 85-A instead of Intermediate 5-A was used to synthesize Intermediate 5-3. This compound was identified using LC-MS and nuclear magnetic resonance (NMR).

Synthesis Example 26: Synthesis of Compound 95

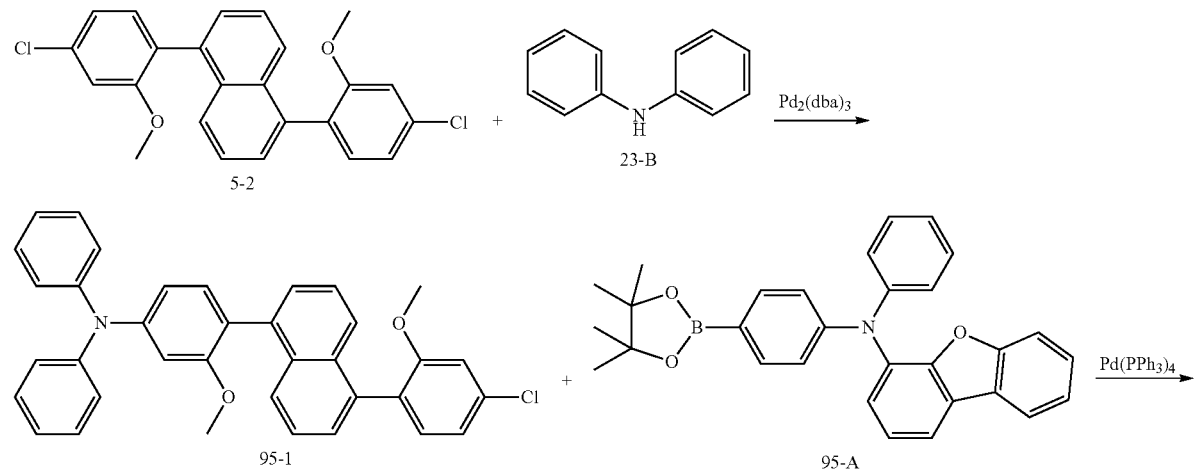

-continued

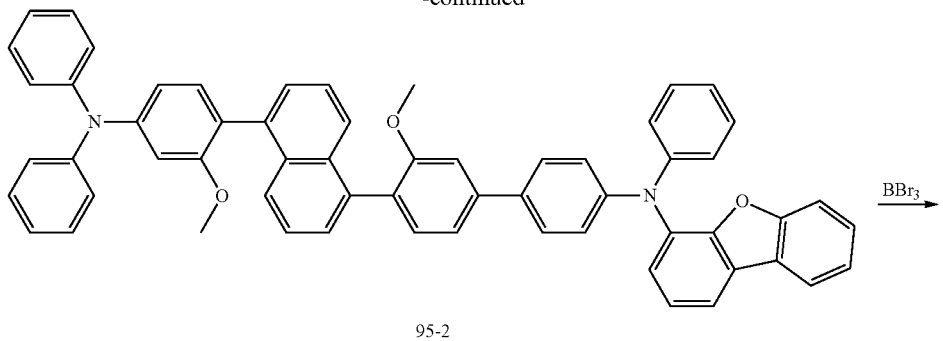
95-2

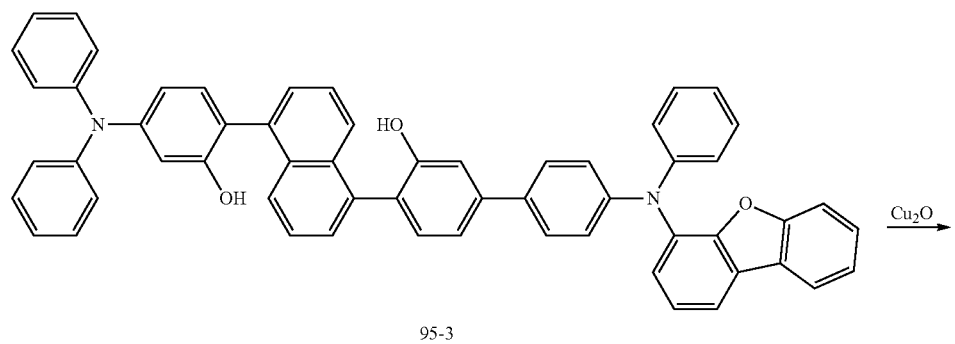
95-3

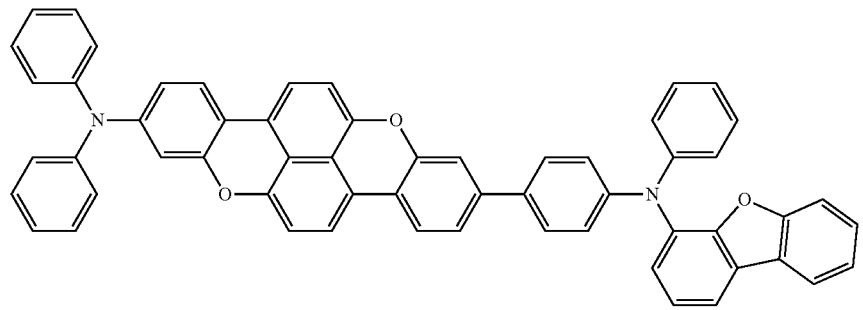
95

Synthesis of Intermediate 95-1

Intermediate 95-1 was obtained in the same manner as in the synthesis of Intermediate 5-3 in Synthesis Example 1, except that the amount of Intermediate 5-A was changed from 40.0 to 20.0 mmol.

Synthesis of Intermediate 95-2

11.9 g (22.0 mmol) of Intermediate 95-1, 10.1 g (22.0 mmol) of Intermediate 95-A, 1.27 g (1.1 mmol) of tetrakis(triphenylphosphine)palladium ($Pd(PPh_3)_4$), and 4.50 g (33 mmol) of $K_2CO_3$ were dissolved in 60 mL of a mixed THF and $H_2O$ (2:1 by volume) solution to obtain a solution, which was then stirred at about 70° C. for about 5 hours. The reaction mixture was cooled down to ambient temperature, and 60 mL of water was then added thereto, followed by extracting three times with 60 mL of ethyl ether. The organic phase was collected, and was dried using magnesium sulfate to evaporate the solvent. The residue was separated and purified using silica gel column chromatography to obtain 11.8 g of Intermediate 95-2 (Yield: 64%). This compound was identified using LC-MS.

Synthesis of Intermediate 95-3

Intermediate 95-3 was obtained in the same manner as in the same manner as in the synthesis of Intermediate 5-4 in Synthesis Example 1, except that Intermediate 95-2 instead of Intermediate 5-3 was used.

Synthesis of Compound 95

2.8 g of Compound 95 (Yield 69%) was synthesized in the same manner as in the synthesis of Compound 5 in Synthesis Example 1, except that Intermediate 95-3 instead of Intermediate 5-4 was used. This compound was identified using LC-MS and nuclear magnetic resonance (NMR).

The compounds obtained in the above-described synthesis examples were identified using $^1$H NMR and mass spectroscopy/fast atom bombardment (MS/FAB). The results are shown in Table 1, below. The compounds represented by Formula 1 above may be synthesized with reference to Synthesis Examples 1 to 26.

TABLE 1

| Compound | $^1$H NMR (CDCL$_3$, 400 MHz) | MS/FAB found | MS/FAB calc. |
|---|---|---|---|
| 1 | δ = 7.90-7.85 (m, 2H), 7.65-7.62 (m, 2H), 7.31-7.29 (m, 2H), 7.09-7.04 (m, 8H), 6.76-6.74 (m, 2H), 6.66-6.62 (m, 4H), 6.50-6.48 (m, 2H), 6.32-6.27 (m, 8H), | 642.24 | 642.23 |
| 5 | δ = 7.92-7.87 (m, 2H), 7.65-7.62 (m, 2H), 7.40-7.36 (m, 4H), 7.31-7.29 (m, 2H), 7.09-7.04 (m, 4H), 6.76-6.52 (m, 8H), 6.52-6.50 (m, 2H), 6.37-6.34 (m, 4H), 0.24 (s, 18H), | 786.31 | 786.31 |
| 7 | δ = 7.90-7.87 (m, 2H), 7.60-7.54 (m, 6H), 7.49-7.44 (m, 6H), 7.31-7.29 (m, 2H), 7.21-7.15 (m, 4H), 7.07-6.96 (m, 6H), 6.82-6.80 (m, 2H), 6.65-6.61 (m, 4h), 6.43-6.40 (m, 2H), 6.19-6.16 (m, 4H) | 794.30 | 794.29 |
| 11 | δ = 7.90-7.87 (m, 2H), 7.84-07.82 (m, 2H), 7.73-7.66 (m, 4H), 7.56-7.53 (m, 2H), 7.48-7.40 (m, 4H), 7.31-7.29 (m, 2H), 7.08-6.94 (m, 8H), 6.72-6.70 (m, 2H), 6.65-6.61 (m, 2H), 6.49-6.47 (m, 2H), 6.36-6.33 (m, 4H), | 822.26 | 822.25 |
| 14 | δ = 7.95-7.93 (m, 2H), 7.78-7.76 (m, 2H), 7.70-7.67 (m, 4H), 7.60-7.53 (m, 6H), 7.41-7.38 (m, 2H), 7.31-7.29 (m, 2H), 7.10-7.07 (m, 4H), 6.69-6.66 (m, 2H), 6.76-6.74 (m, 2H), 6.66-6.62 (m, 2H), 6.54-6.51 (m, 2H), 6.36-6.32 (m, 4H), | 742.27 | 742.26 |
| 23 | δ = 8.10-8.06 (m, 2H), 7.74-7.69 (m, 2H), 7.65-7.60 (m, 4H), 7.57-7.48 (m, 6H), 7.44-7.40 (m, 1H), 7.31-7.29 (m, 2H),7.14-7.03 (m, 7H), 6.75-6.73 (m, 1H), 6.67-6.59 (m, 3H), 6.53-6.48 (m, 2H), 6.39-6.37 (m, 1H), 6.30-6.22 (m, 6H), | 812.29 | 812.28 |
| 24 | δ = 8.10-8.06 (m, 2H), 7.84-7.82 (m, 1H), 7.73-7.69 (m, 2H), 7.64 (d, 1H), 7.54 (d, 1H), 7.48-7.40 (m, 2H), 7.31-7.29 (m, 2H), 7.09-7.04 (m, 7H), 7.00 (d, 1H), 6.96-6.94 (m, 1H), 6.74-6.61 (m, 5H), 6.50-6.48 (m, 2H), 6.36-6.27 (m, 5H), | 732.24 | 732.24 |
| 25 | δ = 8.10-8.06 (m, 2H), 7.84-7.82 (m, 1H), 7.72-7.69 (m, 2H), 7.65-7.61 (m, 3H), 7.56-7.38 (m, 8H), 7.31-7.29 (m, 2H), 7.09-6.94 (m, 6H), 6.74-6.62 (m, 6H), 6.50-6.48 (m, 2H), 6.30-6.27 (m, 4H) | 808.28 | 808.27 |
| 29 | δ = 8.10-8.06 (m, 2H), 7.89 (dd, 1H), 7.76 (dd, 1H), 7.72-7.69 (m, 3H), 7.65-7.63 (m, 2H), 7.42-7.35 (m, 3H), 7.31-7.29 (m, 2H), 7.22 (t, 1H), 7.09-7.03 (m, 6H), 6.97 (d, 1H), 6.91 (t, 1H), 6.74-6.71 (m, 2H), 6.65-6.61 (m, 3H), 6.50-6.47 (m, 2H), 6.36-6.33 (m, 2H), 6.30-6.27 (m, 4H) | 808.27 | 808.27 |
| 31 | δ = 8.06-8.04 (m, 2H), 7.83 (d, 1H), 7.78-7.71 (m, 4H), 7.67-7.62 (m, 2H),7.58-7.50 (m, 5H), 7.44-7.38 (m, 2H), 7.31-7.29 (m, 2H), 7.09-7.04 (m, 5H), 7.00 (dd, 1H), 6.66-6.62 (m, 2H), 6.79-6.74 (m, 2H), 6.55 (dd, 1H), 6.49 (dd, 1H), 6.31-6.27 (m, 4H) | 782.27 | 782.26 |
| 35 | δ = 8.10-8.06 (m, 2H), 7.83 (d, 1H), 7.74-7.62 ( m, 3H), 7.59-7.51 (m, 3H), 7.44-7.40 (m, 1H), 7.31-7.29 (m, 2H), 7.09-7.05 (m, 5H), 6.87-6.81 (m, 2H), 6.75-6.73 (m, 1H), 6.68-6.62 (m, 4H), 6.52-6.48 (m, 2H), 6.30-6.27 (m, 4H) | 768.83 | 768.82 |
| 40 | δ = 8.58-8.57 (m, 1H), 8.43-8.41 (m, 2H), 8.20-8.16 (m, 1H), 8.00-7.95 (m, 1H), 7.78-7.76 (m, 1H), 7.71-7.63 (m, 4H), 7.58-7.54 (m, 3H), 7.43-7.30 (m, 1H), 7.35-7.29 (m, 4H), 7.14-7.04 (m, 6H), 6.77-6.74 (m, 2H), 6.66-6.60 (m, 6H), 6.30-6.27 (m, 4H), 1.36 (s, 6H) | 858.33 | 858.32 |
| 50 | δ = 8.59-8.57 (m, 1H), 8.43-8.41 (m, 2H), 7.96-7.92 (m, 1H), 7.72-7.68 (m, 2H), 7.65 -7.63 (m, 2H), 7.58-7.53 (m, 2H), 7.43-7.36 (m, 4H), 7.31-7.29 (m, 2H), 7.09-7.04 (m, 4H), 6.74-6.71 (m, 3H), 6.67-6.62 (m, 3H) 6.50-6.45 (m, 3H), 6.30-6.27 (m, 4H) | 767.27 | 767.26 |
| 53 | δ = 8.60-8.57 (m, 1H), 8.43-8.41 (m, 2H), 8.19-8.15 (m, 1H), 7.84-7.80 (m, 1H), 7.74-7.54 (m, 12H), 7.50-7.40 (m, 6H), 7.35-7.29 (m, 3H), 7.09-7.04 (m, 4H), 6.97 (d, 1H) 6.92-6.90 (m, 1H), 6.76-6.74 (m, 1H), 6.65-6.63 (m, 2H), 6.49 (dd, 1H), 6.39-6.37 (m, 1H), 6.31-6.27 (m, 5H) | 894.32 | 894.32 |
| 57 | δ = 8.59-8.57 (m, 1H), 8.43-8.41 (m, 2H), 8.20-8.17 (m, 1H), 8.13-8.11 (m, 1H), 8.00-7.96 (m, 1H), 7.82 (d ,1H), 7.76 (d, 1H), 7.72-7.62 (m, 4H), 7.56-7.53 (m, 2H), 7.46-7.35 (m, 4H), 7.31- 7.29 (m, 2H), 7.09-7.04 (m, 5H), 6.90 (dd, 1H), 6.76-6.74 (m, 1H), 6.66-6.60 (m, 3H), 6.50-6.47 (m, 2H), 6.30-6.27 (m, 4H) | 848.26 | 848.25 |

TABLE 1-continued

| Compound | $^1$H NMR (CDCL$_3$, 400 MHz) | MS/FAB found | MS/FAB calc. |
|---|---|---|---|
| 63 | δ = 7.85-7.82 (m, 2H), 7.77 (dd, 1H), 7.68 (dd, 1H), 7.59-7.54 (m, 4H), 7.50-7.44 (m, 3H), 7.37-7.29 (m, 3H), 7.21-6.97 (m, 9H), 6.86 (dd, 1H), 6.81 (d, 1H), 6.69-6.60 (m, 4H), (6.50-6.46 (m, 2H), 6.41 (m, 1H), 6.34-6.31 (m, 2H), 6.19-6.16 (m, 6H), 1.61 (s, 6H) | 834.33 | 834.32 |
| 64 | δ = 8.10-8.07 (m, 2H), 8.73-8.69 (m, 2H), 7.65-7.40 (m, 16H), 7.31-7.29 (m, 2H), 7.21-6.96 (m, 8H), 6.81 (d, 1H), 6.65-6.59 (m, 3H), 6.53-6.51 (m, 1H), 6.43-6.37 (m, 2H), 6.26-6.23 (m, 2H), 6.19-6.16 (m, 2H) | 888.33 | 888.32 |
| 65 | δ = 8.10-8.07 (m, 2H), 7.84-7.82 (m, 1H), 7.73-7.68 (m, 2H), 7.59-7.54 (m, 4H), 7.50-7.40 (m, 5H), 7.31-7.29 (m, 2H), 7.21-7.15 (m, 2H), 7.05-6.94 (m, 7H), 6.82-6.80 (m, 1H), 6.72-6.70 (m, 1H), 6.65-6.61 (m, 3H), 6.48 (dd, 1H), 6.41 (dd, 1H), 6.37-6.35 (m, 2H), 6.19-6.15 (m, 2H) | 808.27 | 808.27 |
| 69 | δ = 8.59-8.57 (m, 1H), 8.43-8.41 (m, 2H), 8.20-8.18 (m, 1H), 7.97-7.94 (m, 1H), 7.71-7.54 (m, 8H), 7.94-7.39 (m, 4H), 7.31-7.29 (m, 2H), 7.21-7.15 (m, 3H), 7.08-6.96 (m, 5H), 6.81 (d, 1H), 6.65-6.61 (m, 4H), 6.45-6.40 (m, 2H), 6.27-6.16 (m, 4H) | 818.30 | 818.29 |
| 70 | δ = 8.35-8.30 (m, 1H), 8.22-8.20 (m, 2H), 8.11 (d, 1H), 7.93-7.90 (m, 1H), 7.76-7.54 (m, 8H), 7.50-7.44 (m, 4H), 7.31-7.29 (m, 2H), 7.21-7.15 (m, 2H) 7.11-6.96 (m, 6H), 6.82-6.80 (m, 1H), 6.76-6.75 (m, 1H), 6.65-6.60 (m, 3H) 6.53 (dd, 1H), 6.42 (dd, 1H), 6.36-6.33 (m, 2H), 6.19-6.16 (m, 2H) | 818.30 | 818.29 |
| 73 | δ = 8.12-8.10 (m, 2H), 7.84-7.82 (m, 1H), 7.78-7.76 (m, 1H) 7.72-7.68 (m, 3H), 7.58-7.54 (m, 2H), 7.48-7.40 (m, 2H) 7.38-7.29 (m, 3H), 7.14-6.99 (m, 7H), 6.96-6.94 (m, 1H), 6.86 (dd, 1H), 6.71-6.61 (m, 4H), 6.50-6.46 (m, 3H), 6.36-6.31 (m, 4H), 1.61 (s, 6H) | 848.31 | 848.30 |
| 78 | δ = 8.10-8.08 (m, 2H), 7.78-7.77 (m, 1H), 7.70-7.54 (m, 6H), 7.41-7.36 (m, 3H), 7.31-7.29 (m, 2H), 7.10-7.04 (m, 4H), 6.89-6.86 (m, 1H), 6.77-6.75 (m, 2H), 6.71-6.62 (m, 4H), 6.54-6.50 (m, 2H), 6.37-6.33 (m, 4H), 0.24 (s, 9H) | 764.30 | 764.29 |
| 82 | δ = 8.03-8.00 (m, 2H), 7.78-7.76 (m, 1H), 7.73-7.49 (m, 16H), 7.44-7.38 (m, 2H), 7.31-7.29 (m, 2H), 7.14-7.03 (m, 5H), 6.89-6.86 (m, 1H), 6.76-6.74 (m, 1H), 6.67-6.59 (m, 2H), 6.54-6.51 (m, 2H), 6.39-6.33 (m, 3H), 6.26-6.22 (m, 2H) | 862.30 | 862.30 |
| 85 | δ = 8.43-8.40 (m, 2H), 8.19-8.16 (m, 2H), 7.66-7.63 (m, 2H), 7.45-7.41 (m, 2H), 7.31-7.21 (m, 8H), 6.95-6.88 (m, 4H), 6.79-6.71 (m, 6H), 6.64-6.62 (m, 2H) | 644.23 | 644.22 |
| 91 | δ = 8.33-8.31 (m, 2H), 8.10-8.06 (m, 1H), 7.78-7.73 (m, 2H), 7.70-7.66 (m, 1H), 7.61-7.54 (m, 6H), 7.50-7.38 (m, 5H), 7.31-7.29 (m, 2H), 7.21-7.15 (m, 3H), 7.07-6.96 (m, 4H), 6.92-6.90 (m, 1H), 6.82-6.76 (m, 2H), 6.67-6.60 (m, 3H), 6.41 (dd, 1H), 6.19-6.16 (m, 2H) | 769.28 | 769.27 |
| 95 | δ = 8.30 (dd, 1H), 8.26 (dd, 1H), 7.94-7.92 (m, 1H), 7.84-7.79 (m, 2H), 7.73-7.71 (m, 1H), 7.83 (dd, 1H), 7.57-7.52 (m, 1H), 7.48-7.39 (m, 5H), 7.30 (d, 1H), 7.18 (d, 1H), 7.09-6.96 (m, 8H), 6.76-6.74 (m, 1H), 6.66-6.61 (m, 3H), 6.51-6.47 (m, 3H), 6.30-6.22 (m, 6H) | 808.27 | 808.27 |

Example 1

A corning 15 Ω/cm$^2$ (1,200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting ITO glass substrate was mounted into a vacuum deposition device.

After 2-TNATA was vacuum-deposited on the ITO anode of the ITO glass substrate to form an HIL having a thickness of 600 Å, NPB was deposited on the HIL to form a HTL having a thickness of about 300 Å, and then ADN (host) and Compound 5 (dopant) were co-deposited in a weight ratio of 98:2 on the HTL to form an EML having a thickness of about 300 Å.

Then, Alq$_3$ was deposited on the EML to form an ETL having a thickness of about 300 Å, and then LiF was deposited on the ETL to form an EIL having a thickness of about 10 Å. Then, Al was deposited on the EIL to form a cathode having a thickness of about 3,000 Å, thereby completing the manufacture of an organic light-emitting device.

Example 2

An organic light-emitting device was manufactured in the same manner as in Example 1, except that Compound 23 instead of Compound 5 was used to form the EML.

Example 3

An organic light-emitting device was manufactured in the same manner as in Example 1, except that Compound 25 instead of Compound 5 was used to form the EML.

Example 4

An organic light-emitting device was manufactured in the same manner as in Example 1, except that Compound 31 instead of Compound 5 was used to form the EML.

Example 5

An organic light-emitting device was manufactured in the same manner as in Example 1, except that Compound 50 instead of Compound 5 was used to form the EML.

Example 6

An organic light-emitting device was manufactured in the same manner as in Example 1, except that Compound 63 instead of Compound 5 was used to form the EML.

Example 7

An organic light-emitting device was manufactured in the same manner as in Example 1, except that Compound 170 instead of Compound 5 was used to form the EML.

Example 8

An organic light-emitting device was manufactured in the same manner as in Example 1, except that Compound 73 instead of Compound 5 was used to form the EML.

Example 9

An organic light-emitting device was manufactured in the same manner as in Example 1, except that Compound 91 instead of Compound 5 was used to form the EML.

Comparative Example 1

An organic light-emitting device was manufactured in the same manner as in Example 1, except that Compound An instead of Compound 5 was used to form the EML.

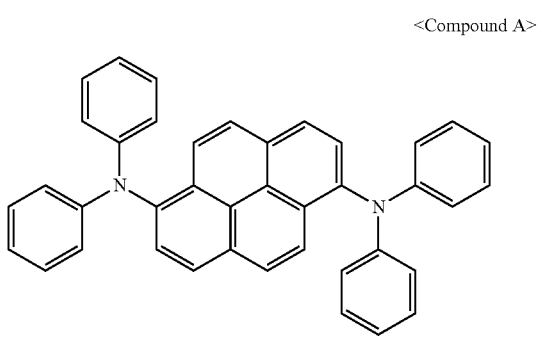 [SMILES: c1ccc(N(c2ccccc2)c2ccc3ccc4c(N(c5ccccc5)c5ccccc5)ccc5ccc2c3c54)cc1]

<Compound A>

Comparative Example 2

An organic light-emitting device was manufactured in the same manner as in Example 1, except that Compound B instead of Compound 5 was used to form the EML.

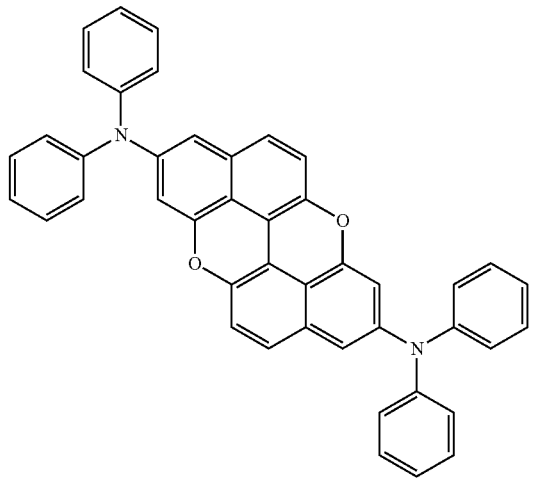

<Compound B>

Comparative Example 3

An organic light-emitting device was manufactured in the same manner as in Example 1, except that Compound C instead of Compound 5 was used to form the EML.

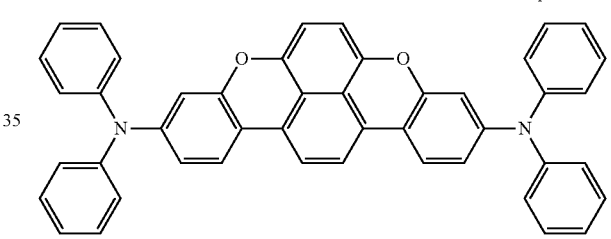

<Compound C>

Evaluation Example 1

Driving voltages, current densities, luminances, efficiencies, and half-lifetimes of the organic light-emitting devices of Examples 1 to 9 and Comparative Examples 1 to 3 were evaluated using a Kethley Source-Measure Unit (SMU 236) and a PR650 (Spectroscan) Source Measurement Unit. (available from Photo Research, Inc.). The results are shown in Table 2, below. A half-lifetime was measured as the time taken until a measured initial luminocity (assumed as 100%) is reduced to 50%.)

TABLE 2

| Example | Dopant in EML | Driving voltage (V) | Current density (mA/cm$^2$) | Luminance (cd/m$^2$) | Efffficiency (cd/A) | Emission color | Half-lifetime (hr @100 mA/cm$^2$) |
|---|---|---|---|---|---|---|---|
| Example 1 | Compound 5 | 6.22 | 50 | 3230 | 6.46 | Blue | 362 |
| Example 2 | Compound 23 | 6.20 | 50 | 3560 | 7.12 | Blue | 345 |
| Example 3 | Compound 25 | 6.15 | 50 | 3611 | 7.22 | Blue | 351 |
| Example 4 | Compound 31 | 6.30 | 50 | 3575 | 7.15 | Blue | 359 |
| Example 5 | Compound 50 | 6.20 | 50 | 3150 | 6.30 | Blue | 370 |

TABLE 2-continued

| Example | Dopant in EML | Driving voltage (V) | Current density (mA/cm$^2$) | Luminance (cd/m$^2$) | Effficiency (cd/A) | Emission color | Half-lifetime (hr @100 mA/cm$^2$) |
|---|---|---|---|---|---|---|---|
| Example 6 | Compound 63 | 6.20 | 50 | 3550 | 7.10 | Blue | 346 |
| Example 7 | Compound 70 | 6.18 | 50 | 3520 | 7.04 | Blue | 350 |
| Example 8 | Compound 73 | 6.22 | 50 | 3605 | 7.21 | Blue | 360 |
| Example 9 | Compound 91 | 6.20 | 50 | 3220 | 6.44 | Blue | 315 |
| Comparative Example 1 | Compound A | 7.01 | 50 | 2645 | 5.29 | Blue | 258 |
| Comparative Example 2 | Compound B | 6.75 | 50 | 2420 | 4.84 | Blue | 260 |
| Cpmparative Example 3 | Compound C | 6.89 | 50 | 2608 | 5.21 | Blue | 245 |

Referring to Table 1, the organic light-emitting devices of Examples 1 to 9 exhibited improved driving voltages, improved current densities, improved luminances, improved efficiencies, and improved half-lifetimes, compared to those of the organic light-emitting devices of Comparative Examples 1 to 3.

As described above, according to the one or more of the above embodiments, an organic light-emitting device including a condensed cyclic compound of Formula 1 above may have a low driving voltage, a high efficiency, a high luminance, and a long lifetime.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. A condensed cyclic compound represented by Formula 1:

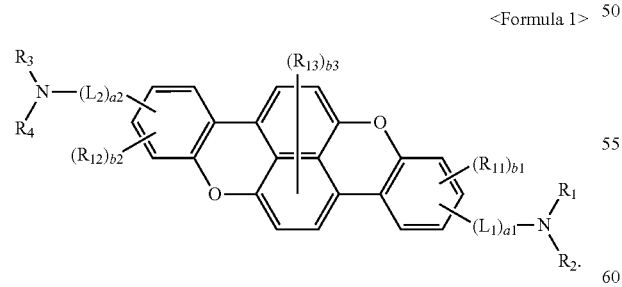

<Formula 1> wherein, in Formula 1, $L_1$ and $L_2$ are each independently a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, or a substituted or unsubstituted divalent non-aromatic hetero-condensed polycyclic group, a1 and a2 are each independently an integer of 0 to 5, $R_1$ to $R_4$ are each independently a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group, or a substituted or unsubstituted monovalent non-aromatic hetero-condensed polycyclic group, $R_{11}$ to $R_{13}$ are each independently a hydrogen, a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cyclo alkyl group, a substituted or unsubstituted $C_2$-$C_{10}$ heterocyclo alkyl group, a substituted or unsubstituted $C_3$-$C_{10}$ cyclo alkenyl group, a substituted or unsubstituted $C_2$-$C_{10}$ heterocyclo alkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic hetero-condensed polycyclic group, —Si($Q_1$)($Q_2$)($Q_3$), or —B($Q_4$)($Q_5$), b1 and b2 are each independently an integer of 1 to 3, and b3 is an integer of 1 to 4, wherein at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, the substituted monovalent non-aromatic hetero-condensed polycyclic group, the substituted $C_1$-$C_{60}$ alkyl group, the substituted $C_2$-$C_{60}$ alkenyl group, the substituted $C_2$-$C_{60}$ alkynyl group, and the substituted $C_1$-$C_{60}$ alkoxy group is:

a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —N($Q_{11}$)($Q_{12}$), —Si($Q_{13}$)($Q_{14}$)($Q_{15}$), or —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic hetero-condensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic hetero-condensed polycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —N($Q_{21}$)($Q_{22}$), —Si($Q_{23}$)($Q_{24}$)($Q_{25}$), or —B($Q_{26}$)($Q_{27}$); or —Si($Q_{31}$)($Q_{32}$)($Q_{33}$), or —B($Q_{34}$)($Q_{35}$), wherein $Q_1$ to $Q_5$, $Q_{11}$ to $Q_{17}$, $Q_{21}$ to $Q_{27}$, and $Q_{31}$ to $Q_{35}$ are each independently a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, or a monovalent non-aromatic hetero-condensed polycyclic group.

2. The condensed cyclic compound as claimed in claim 1, wherein $L_1$ and $L_2$ are each independently:

a phenylene group, a pentalenylene group, an indeylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, an imidazolylene group, a pyrazolylene group, a thiazolylene group, an isothiazolylene group, a oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, a oxadiazolylene group, a triazinylene group, a dibenzofuranylene group, a dibenzothiophenylene group, a benzocarbazolylene group, or a dibenzocarbazolylene group; or a phenylene group, a pentalenylene group, an indeylene group, a naphthylene group, an azulenylene group, a heptalenylene group, an indacenylene group, an acenaphthylene group, a fluorenylene group, a Spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, an imidazolylene group, a pyrazolylene group, a thiazolylene group, an isothiazolylene group, a oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, a oxadiazolylene group, a triazinylene group, a dibenzofuranylene group, a dibenzothiophenylene group, a benzocarbazolylene group, or a dibenzocarbazolylene, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, an a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and —Si($Q_{31}$)($Q_{32}$)($Q_{33}$), in which $Q_{31}$ to $Q_{33}$ are each independently a hydrogen, a $C_1$-$C_{10}$ alkyl group, a $C_1$-$C_{10}$ alkoxy group, a phenyl group, or a naphthyl group.

3. The condensed cyclic compound as claimed in claim 1, wherein $L_1$ and $L_2$ are each independently represented by one of Formulae 3-1 to 3-32:

Formula 3-1

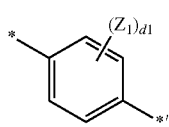

Formula 3-2

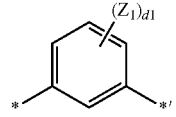

Formula 3-3

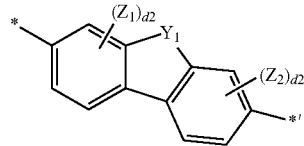

Formula 3-4

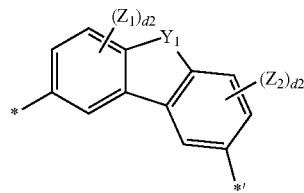

Formula 3-5

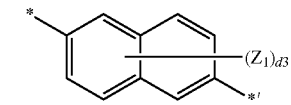

Formula 3-6

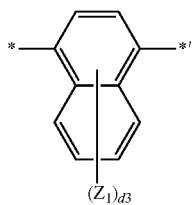

Formula 3-7

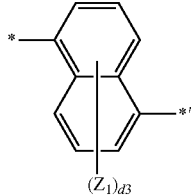

Formula 3-8

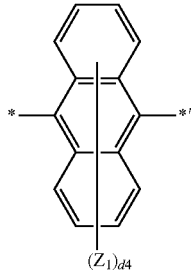

Formula 3-9

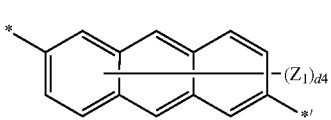

Formula 3-10

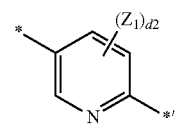

-continued

Formula 3-11

Formula 3-12

Formula 3-13

Formula 3-14

Formula 3-15

Formula 3-16

Formula 3-17

Formula 3-18

Formula 3-19

Formula 3-20

Formula 3-21

Formula 3-22

-continued

Formula 3-23

Formula 3-24

Formula 3-25

Formula 3-26

Formula 3-27

Formula 3-28

Formula 3-29

Formula 3-30

Formula 3-31

-continued

Formula 3-32

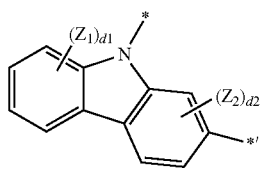

wherein, in Formulae 3-1 to 3-32,

Z$_1$ and Z$_2$ are each independently a hydrogen, a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, a fluorenyl group, a spirofluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, a dibenzocarbazolyl group, or —Si(Q$_{31}$)(Q$_{32}$)(Q$_{33}$), in which Q$_{31}$ to Q$_{33}$ are each independently a hydrogen, a C$_1$-C$_{10}$ alkyl group, a C$_1$-C$_{10}$ alkoxy group, a phenyl group, or a naphthyl group, d1 is an integer of 1 to 4,
d2 is an integer of 1 to 3,
d3 is an integer of 1 to 6,
d4 is an integer of 1 to 8,
d5 is 1 or 2,
d6 is an integer of 1 to 5, and
\* and \*' are binding sites to adjacent atoms.

4. The condensed cyclic compound as claimed in claim 1, wherein L$_1$ and L$_2$ are each independently represented by one of Formulae 4-1 to 4-23, in which \* and \*' are binding sites to adjacent atoms:

Formula 4-1

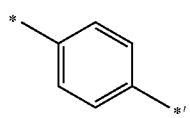

Formula 4-2

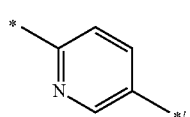

Formula 4-3

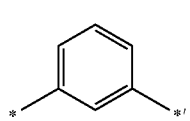

Formula 4-4

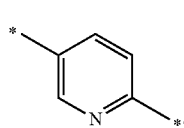

Formula 4-5

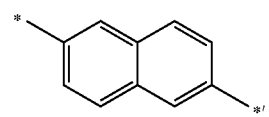

Formula 4-6

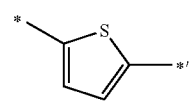

Formula 4-7

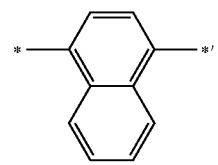

Formula 4-8

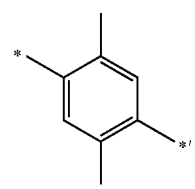

Formula 4-9

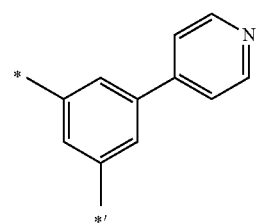

Formula 4-10

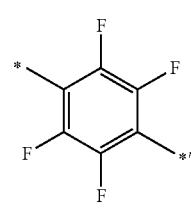

Formula 4-11

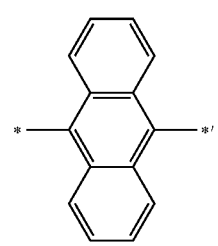

Formula 4-12

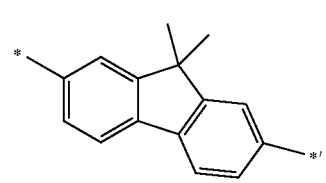

-continued

Formula 4-13
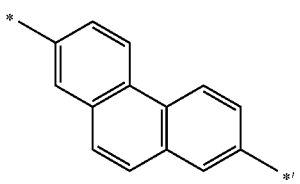

Formula 4-14
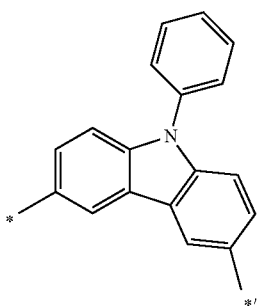

Formula 4-15
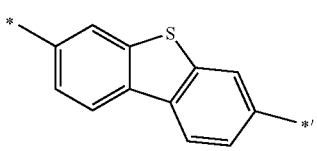

Formula 4-16
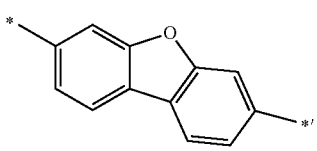

Formula 4-17
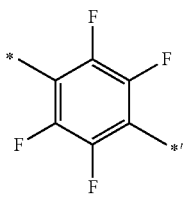

Formula 4-18

Formula 4-19
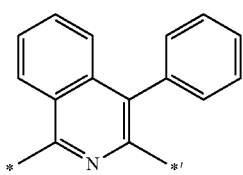

Formula 4-20
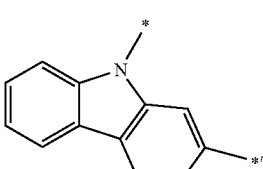

Formula 4-21
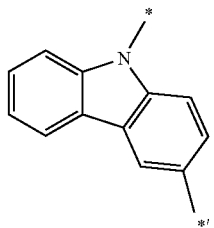

Formula 4-22
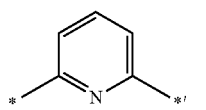

Formula 4-23
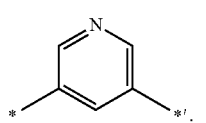

5. The condensed cyclic compound as claimed in claim 1, wherein a1 and a2 are each independently 0, 1, or 2.

6. The condensed cyclic compound as claimed in claim 1, wherein $R_1$ to $R_4$ are each independently:

a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, or a dibenzocarbazolyl group; or a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, or a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentenyl group, a cyclohexyl group, cyclopeptyl, a cyclopentenyl, a cyclohexenyl group, a phenyl group, a pentalenyl group, an indeyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluorantenyl group, a triphenylenyl group, a pyrenyl group, a chrysenyl group, a naphthacenyl group, a pycenyl group, a perylenyl group, a pentaphenyl group, a hexacenyl group, a pentacenyl group, a rubicenyl group, a coronenyl group, a ovalenyl group, a pyrrolyl group, a thiophenyl group, a furanyl group, an imidazolyl group, a pyrazolyl group, a thiazolyl group, an isothiazolyl group, a oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, a oxadiazolyl group, a triazinyl group, a dibenzofuranyl group, a dibenzothiophenyl group, a benzocarbazolyl group, a dibenzocarbazolyl group, and Si($Q_{31}$)($Q_{32}$)($Q_{33}$), in which $Q_{31}$ to $Q_{33}$ are each independently a hydrogen, a $C_1$-$C_{10}$ alkyl group, a $C_1$-$C_{10}$ alkoxy group, a phenyl group, or a naphthyl group.

7. The condensed cyclic compound as claimed in claim 1, wherein $R_1$ to $R_4$ are each independently:
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, or a dibenzocarbazolyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, or a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, a dibenzocarbazolyl group, and —Si($Q_{31}$)($Q_{32}$)($Q_{33}$), in which $Q_{31}$ to $Q_{33}$ are each independently a hydrogen, a $C_1$-$C_{10}$ alkyl group, a $C_1$-$C_{10}$ alkoxy group, a phenyl group, or a naphthyl group.

8. The condensed cyclic compound as claimed in claim 1, wherein $R_1$ to $R_4$ are each independently represented by one of Formulae 5-1 to 5-14:

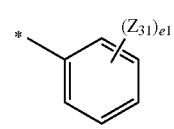

Formula 5-1

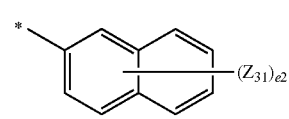

Formula 5-2

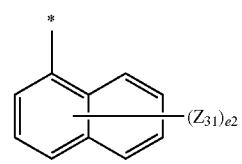

Formula 5-3

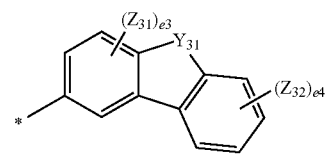

Formula 5-4

-continued

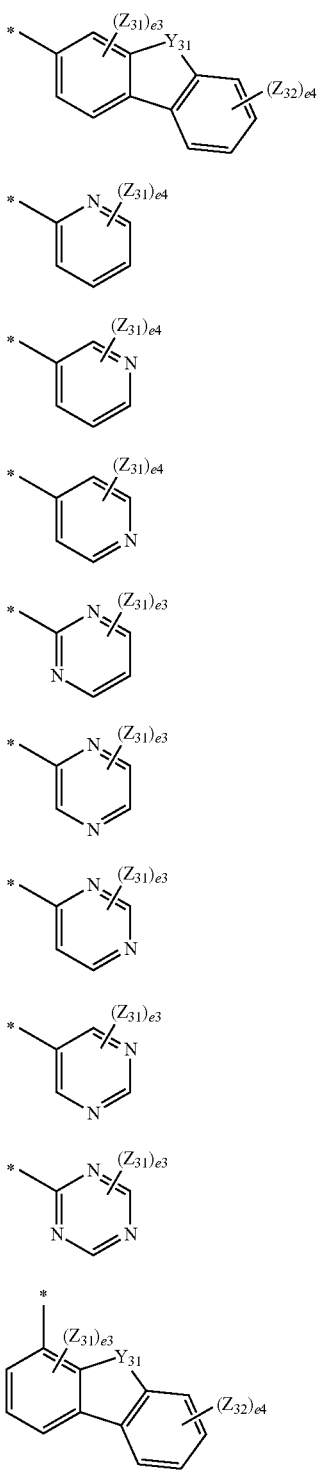

wherein, in Formulae 5-1 to 5-14,
Y$_{31}$ is O, S, C(Z$_{33}$)(Z$_{34}$), or N(Z$_{35}$),
Z$_{31}$ to Z$_{35}$ are each independently a hydrogen, a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, a fluorenyl group, a spirofluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, a dibenzocarbazolyl group, or —Si(Q$_{31}$)(Q$_{32}$)(Q$_{33}$), in which Q$_{31}$ to Q$_{33}$ are each independently a hydrogen, a C$_1$-C$_{10}$ alkyl group, a C$_1$-C$_{10}$ alkoxy group, a phenyl group, or a naphthyl group,
e1 is an integer of 1 to 5,
e2 is an integer of 1 to 7,
e3 is an integer of 1 to 3,
e4 is an integer of 1 to 4,
e5 is 1 or 2, and
* is a binding site to an adjacent atom.

9. The condensed cyclic compound as claimed in claim 1, wherein R$_1$ to R$_4$ are each independently represented by one of Formulae 6-1 to 6-45, in which * is a binding site to an adjacent atom:

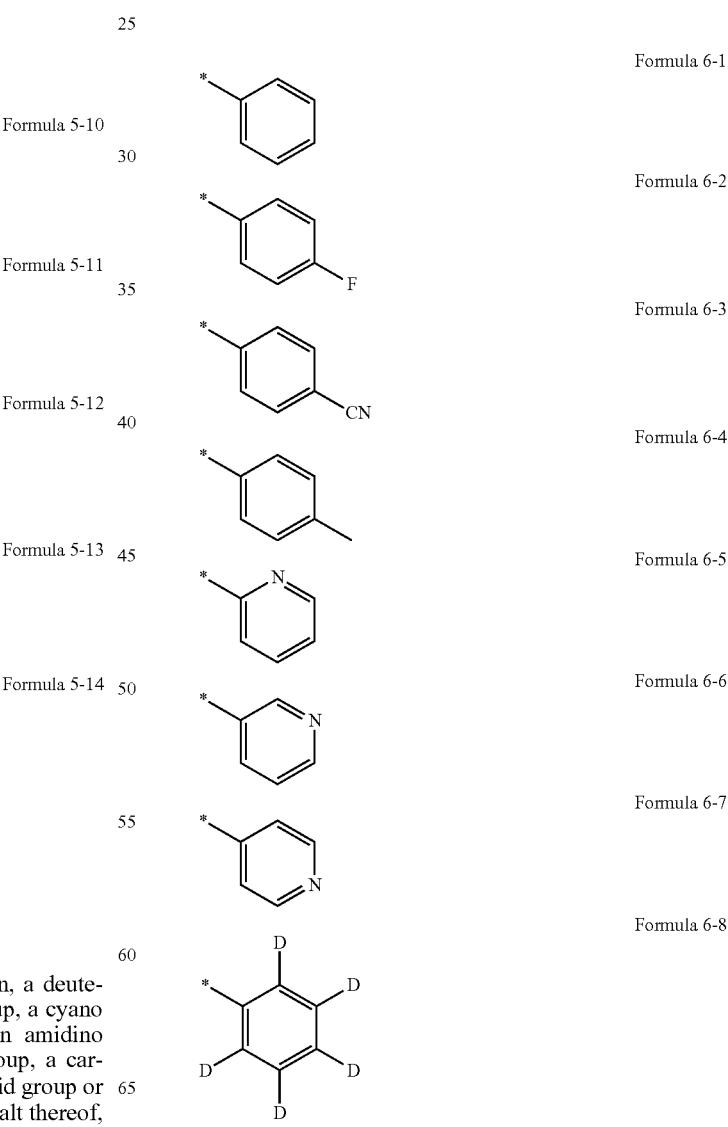

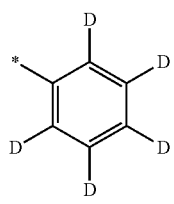

-continued
Formula 6-9
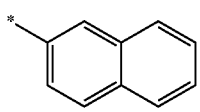
Formula 6-10
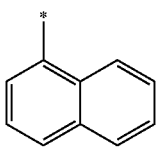
Formula 6-11
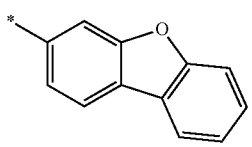
Formula 6-12
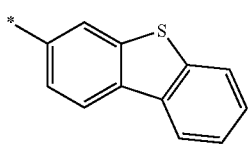
Formula 6-13
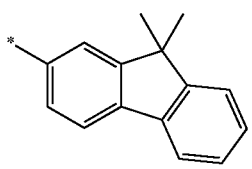
Formula 6-14
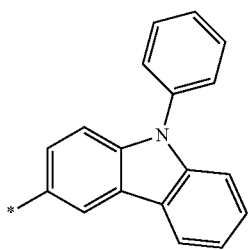
Formula 6-15
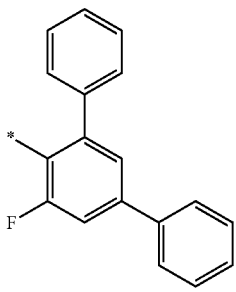
Formula 6-16
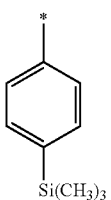
-continued
Formula 6-17
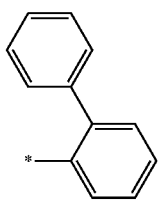
Formula 6-18
Formula 6-19
Formula 6-20
Formula 6-21
Formula 6-22
Formula 6-23
Formula 6-24
Formula 6-25

143
-continued
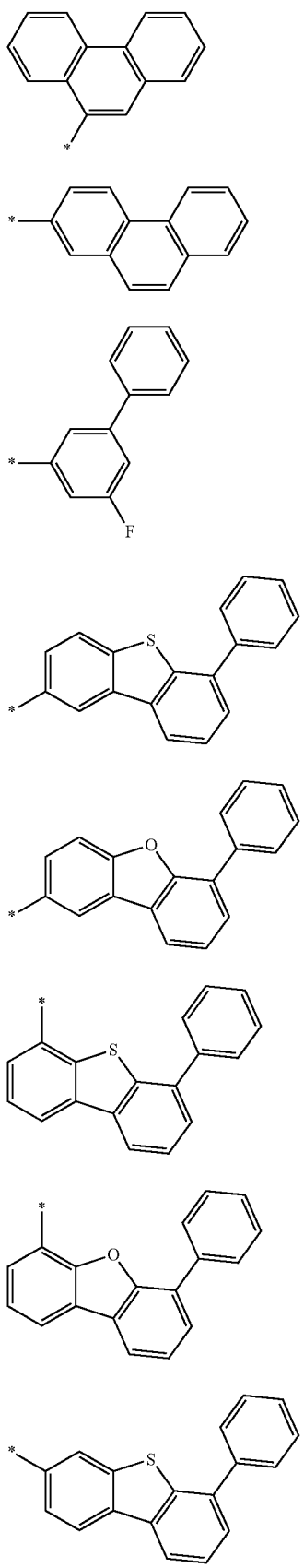
144
-continued
Formula 6-26
Formula 6-27
Formula 6-28
Formula 6-29
Formula 6-30
Formula 6-31
Formula 6-32
Formula 6-33
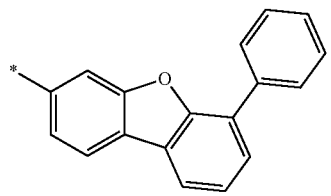
Formula 6-34
Formula 6-35
Formula 6-36
Formula 6-37
Formula 6-38
Formula 6-39
Formula 6-40
Formula 6-41

Formula 6-42

Formula 6-43

Formula 6-44

Formula 6-45

10. The condensed cyclic compound as claimed in claim 1, wherein:

$R_1=R_2=R_3=R_4$;

$R_1=R_3$, $R_1 \neq R_2$, and $R_2=R_4$;

$R_2=R_3$, $R_1 \neq R_2$, and $R_1=R_4$;

$R_1=R_2$, $R_1 \neq R_3$, and $R_3=R_4$;

$R_2=R_3=R_4$, and $R_1 \neq R_2$;

$R_3=R_4$, and $R_1 \neq R_2 \neq R_3$; or $R_1 \neq R_2 \neq R_3 \neq R_4$.

11. The condensed cyclic compound as claimed in claim 1, wherein $R_{11}$ to $R_{13}$ are each independently a hydrogen, a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, a dibenzocarbazolyl group, or —Si($Q_1$)($Q_2$)($Q_3$), in which $Q_1$ to $Q_3$ are each independently a hydrogen, a $C_1$-$C_{10}$ alkyl group, a $C_1$-$C_{10}$ alkoxy group, a phenyl group, or a naphthyl group.

12. The condensed cyclic compound as claimed in claim 1, wherein the condensed cyclic compound represented by Formula 1 is represented by one of Formulae 1A to 1D:

<Formula 1A>

<Formula 1B>

<Formula 1C>

<Formula 1D> wherein $R_1$ to $R_4$, $R_{11}$ to $R_{13}$, $L_1$, $L_2$, a1, a2, b1, and b2 in Formulae 1A to 1D are the same as those defined with respect to Formula 1.

13. The condensed cyclic compound as claimed in claim 12, wherein:

the condensed cyclic compound represented by Formula 1 is represented by Formula 1A, $L_1$ and $L_2$ are each independently represented by one of Formulae 4-1 to 4-23, below, in which * and *' are binding sites to adjacent atoms, a1 and a2 are each independently 0, 1, or 2, $R_1$ to $R_4$ are each independently represented by one of Formulae 6-1 to 6-45, below, in which * is a binding site to an adjacent atom, $R_{11}$ to $R_{13}$ are each independently a hydrogen, a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzocarbazolyl group, a dibenzocarbazolyl group, or —Si($Q_1$)($Q_2$)($Q_3$), in which $Q_1$ to $Q_3$ are each independently a hydrogen, a $C_1$-$C_{10}$ alkyl group, a $C_1$-$C_{10}$ alkoxy group, a phenyl group, or a naphthyl group, and b1 to b3 are each independently 1 or 2:

Formula 4-1
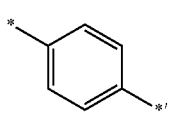

Formula 4-2
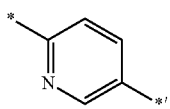

Formula 4-3
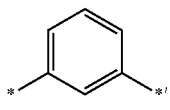

Formula 4-4
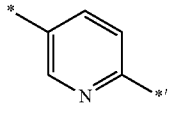

Formula 4-5
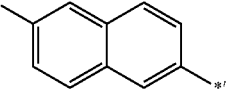

Formula 4-6
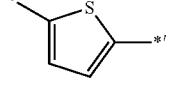

Formula 4-7
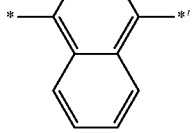

Formula 4-8
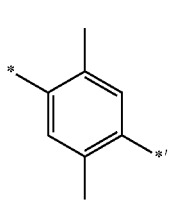

-continued

Formula 4-9
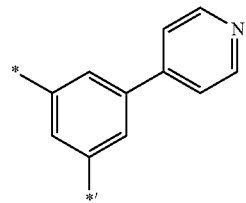

Formula 4-10
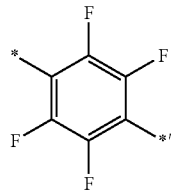

Formula 4-11
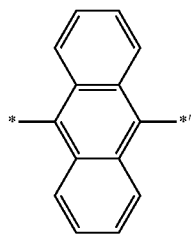

Formula 4-12
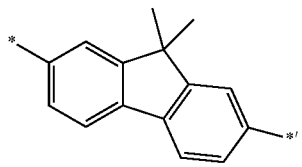

Formula 4-13
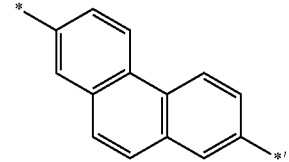

Formula 4-14
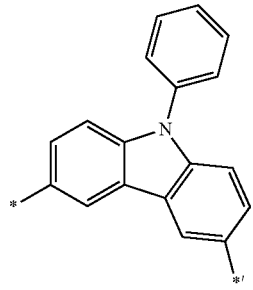

Formula 4-15
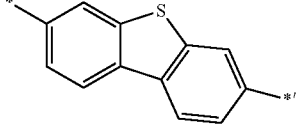

Formula 4-16
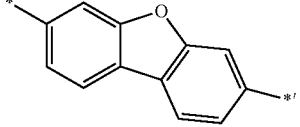

Formula 4-17
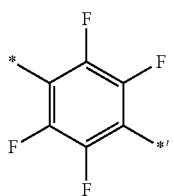
Formula 4-18
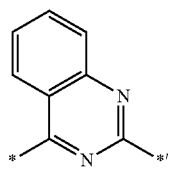
Formula 4-19
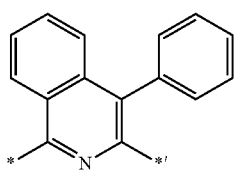
Formula 4-20
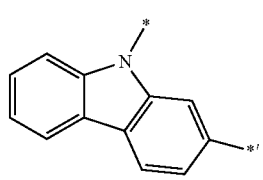
Formula 4-21
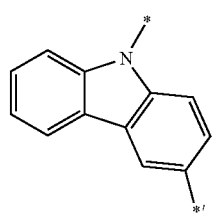
Formula 4-22
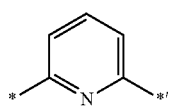
Formula 4-23
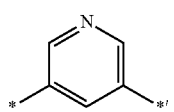
Formula 6-1
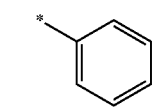
Formula 6-2
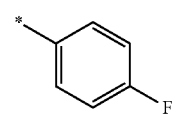
Formula 6-3
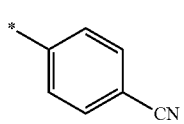
Formula 6-4
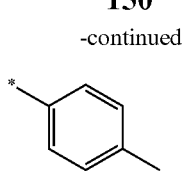
Formula 6-5
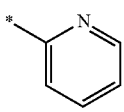
Formula 6-6
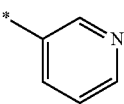
Formula 6-7
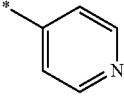
Formula 6-8
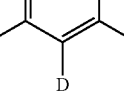
Formula 6-9
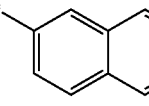
Formula 6-10
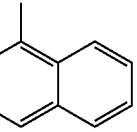
Formula 6-11
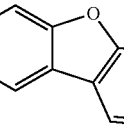
Formula 6-12
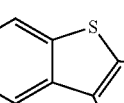
Formula 6-13
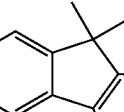

Formula 6-14
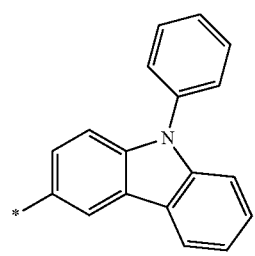
Formula 6-15
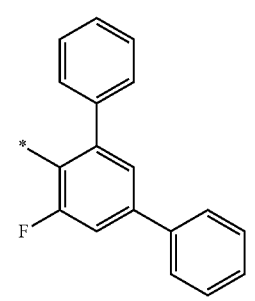
Formula 6-16
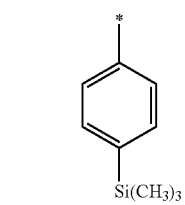
Formula 6-17
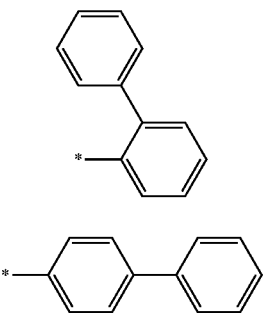
Formula 6-18
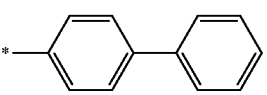
Formula 6-19
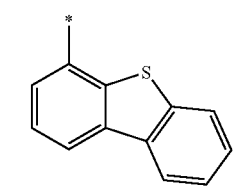
Formula 6-20
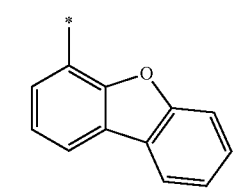
Formula 6-21
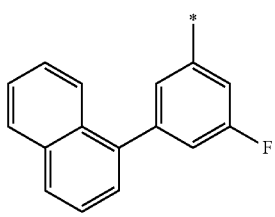
Formula 6-22
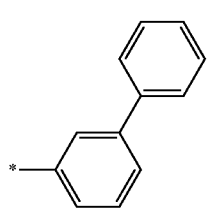
Formula 6-23
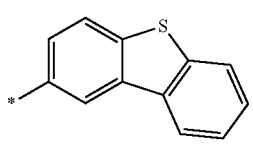
Formula 6-24
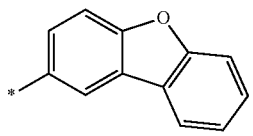
Formula 6-25
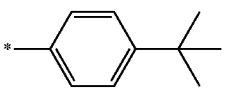
Formula 6-26
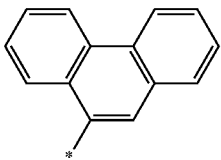
Formula 6-27
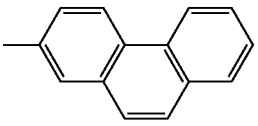
Formula 6-28
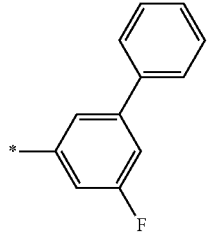
Formula 6-29
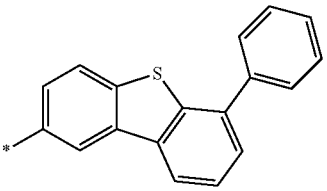

-continued
Formula 6-30
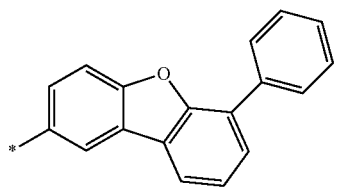
Formula 6-31
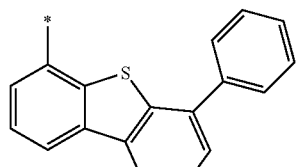
Formula 6-32
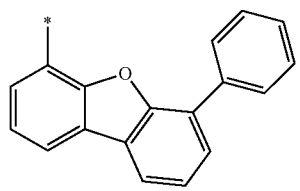
Formula 6-33
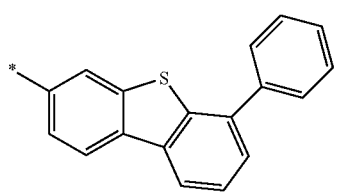
Formula 6-34
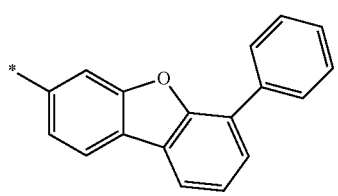
Formula 6-35
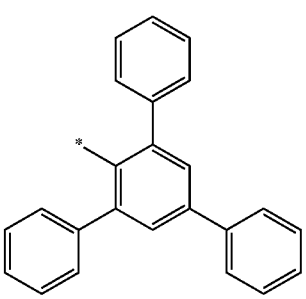
Formula 6-36
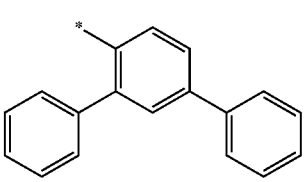
Formula 6-37
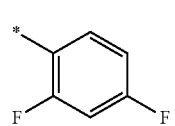
-continued
Formula 6-38
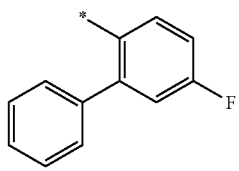
Formula 6-39
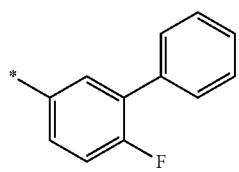
Formula 6-40
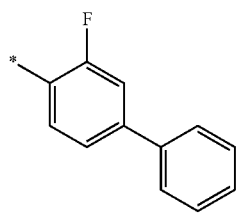
Formula 6-41
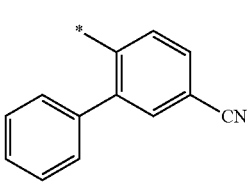
Formula 6-42
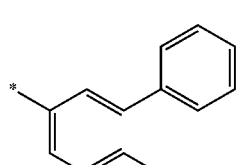
Formula 6-43
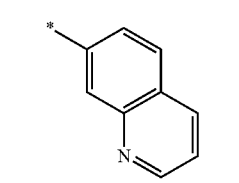
Formula 6-44
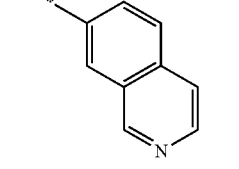
Formula 6-45
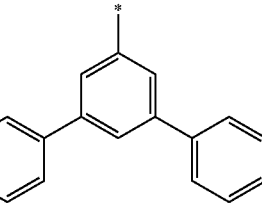
14. The condensed cyclic compound as claimed in claim 1, wherein the condensed cyclic compound represented by Formula 1 includes one of Compounds 1 to 96:

| 1 | 2 |
|---|---|
| 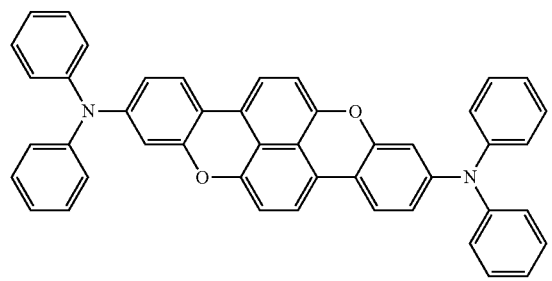 | 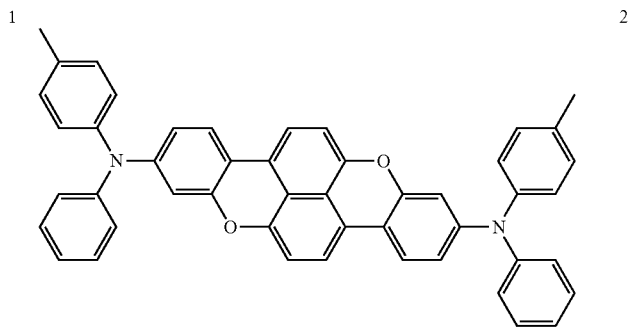 |
| 3 | 4 |
| 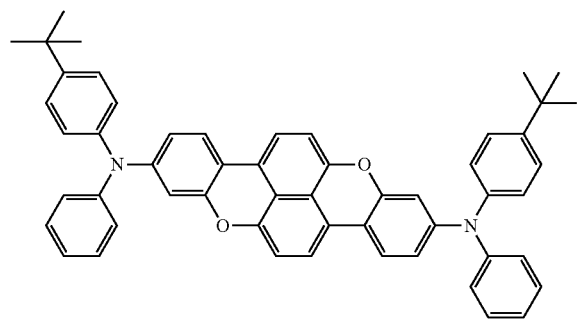 | 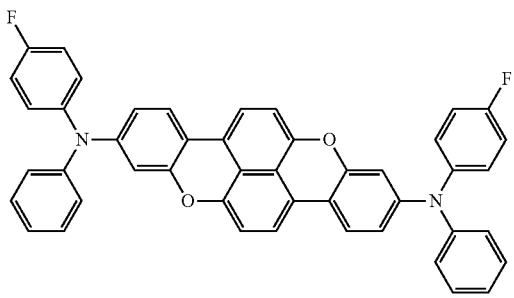 |
| 5 | 6 |
| 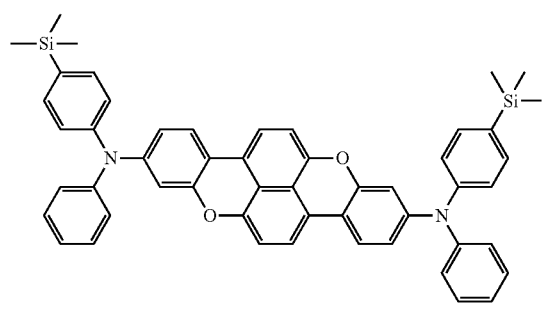 | 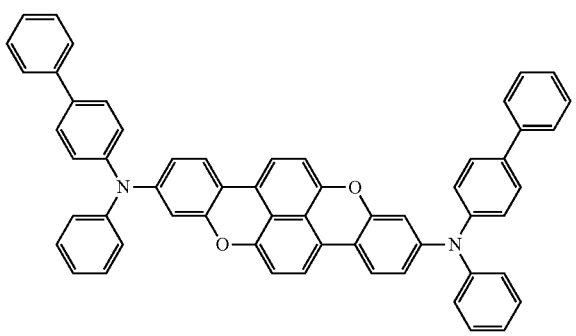 |
| 7 | 8 |
| 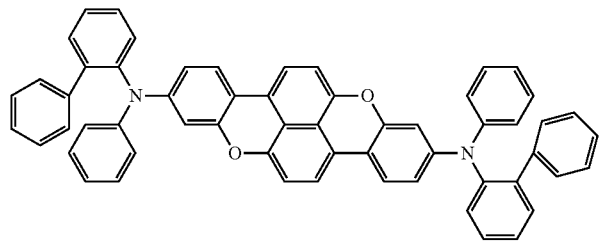 | 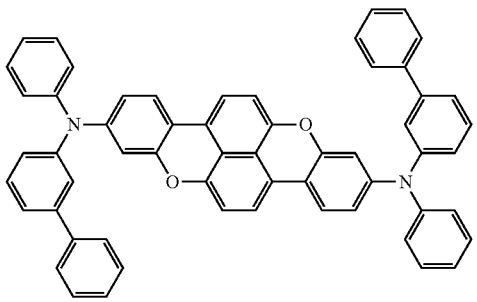 |
| 9 | 10 |
| 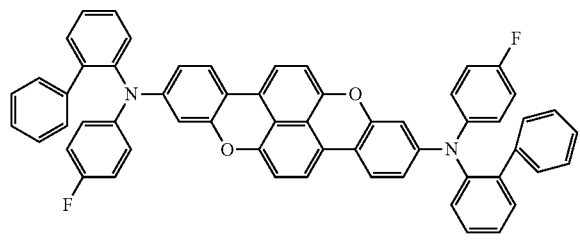 | 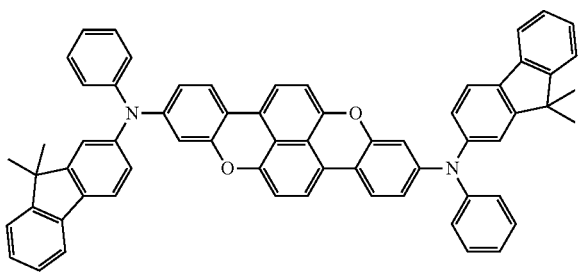 |

-continued
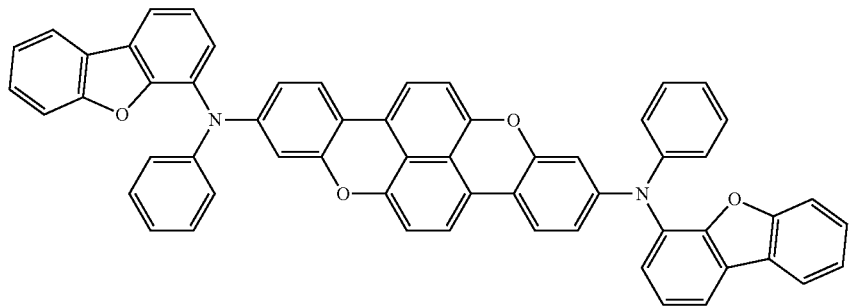
11
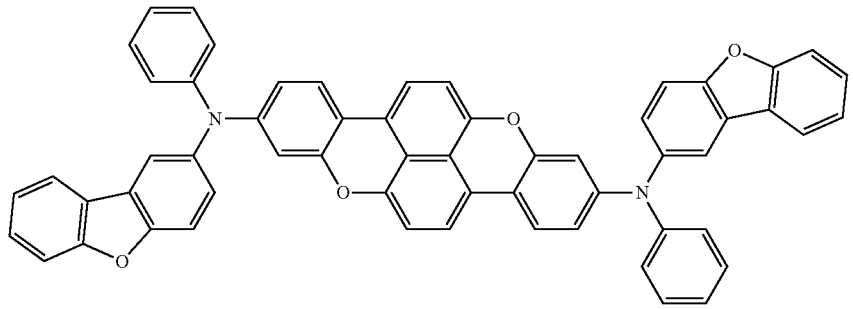
12
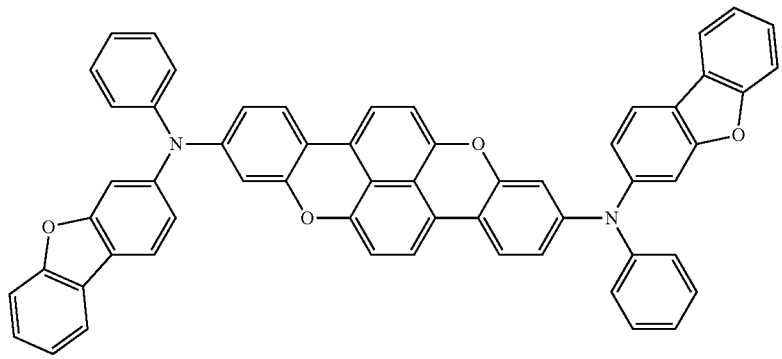
13
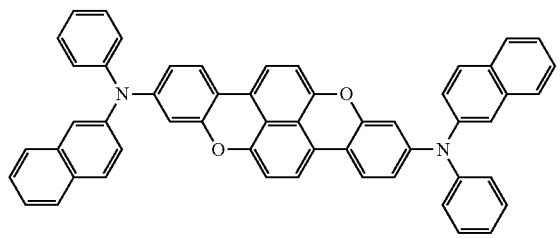
14
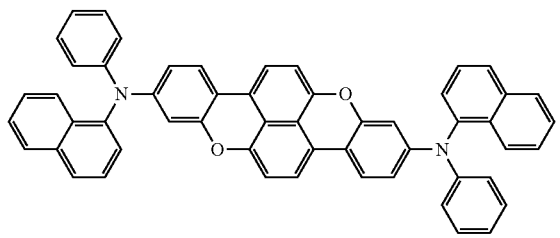
15
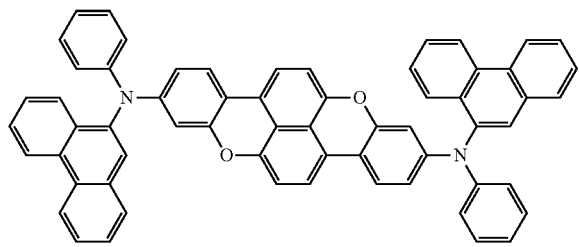
16
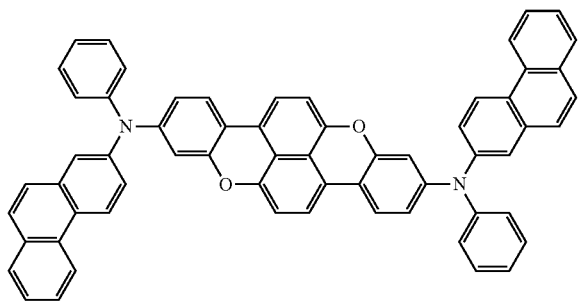
17

-continued
18
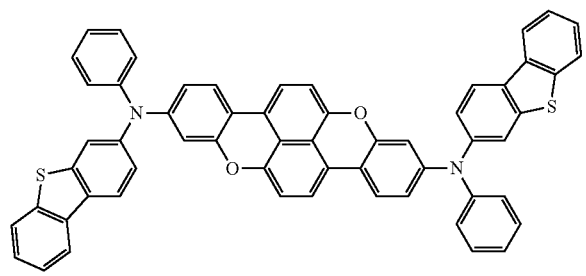
19
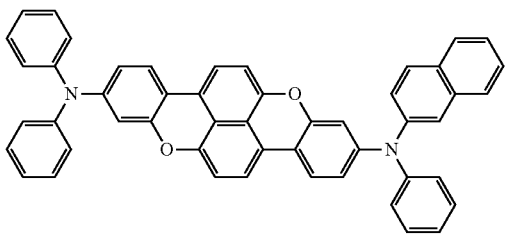
20
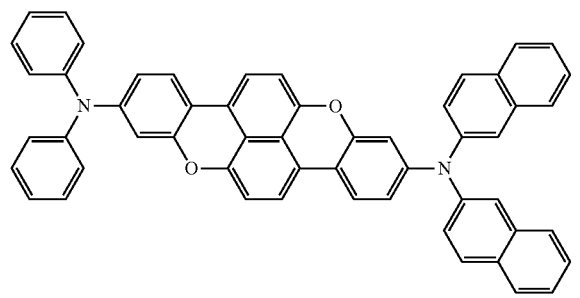
21
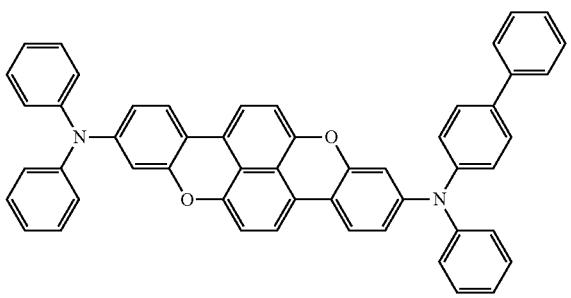
22
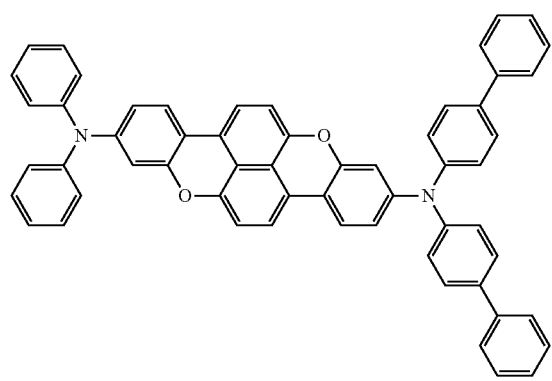
23
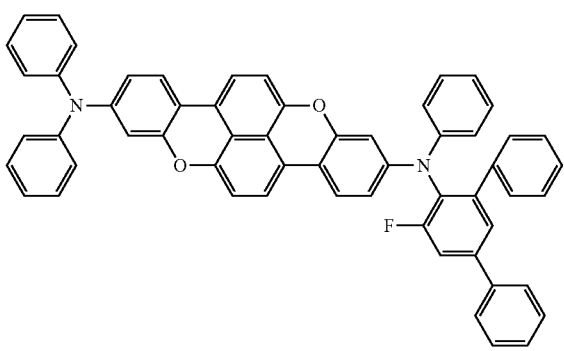
24
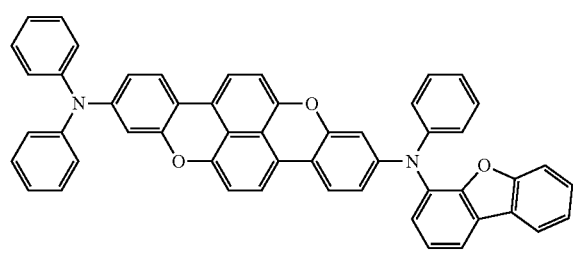
25
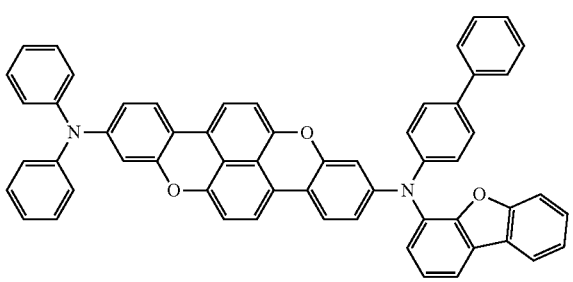
26
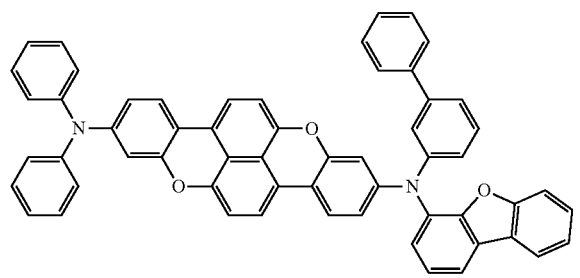
27
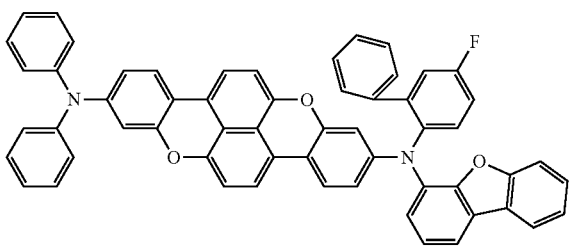

-continued
28
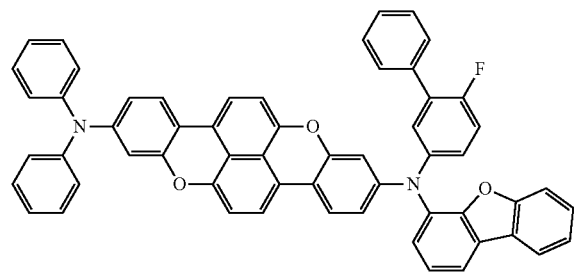
29
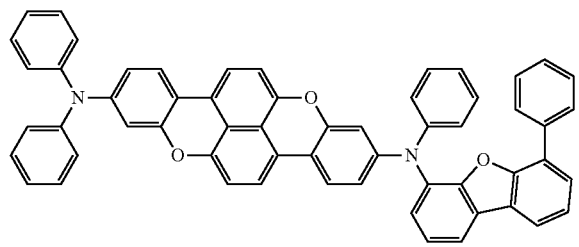
30
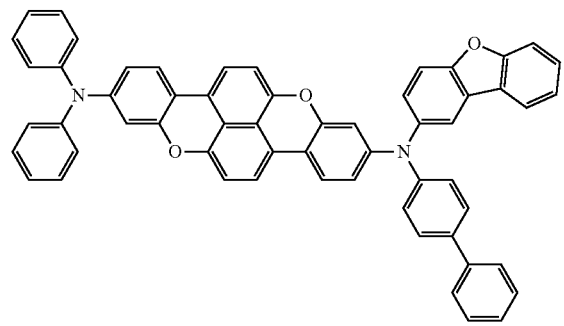
31
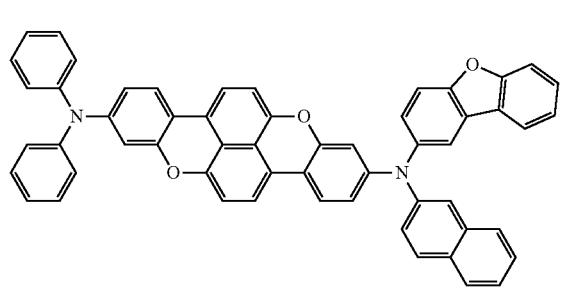
32
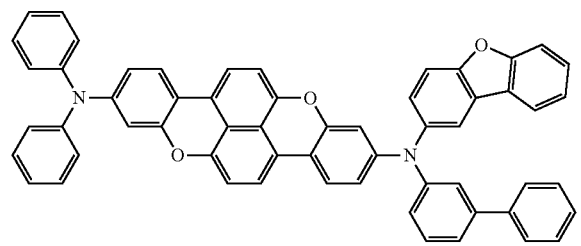
33
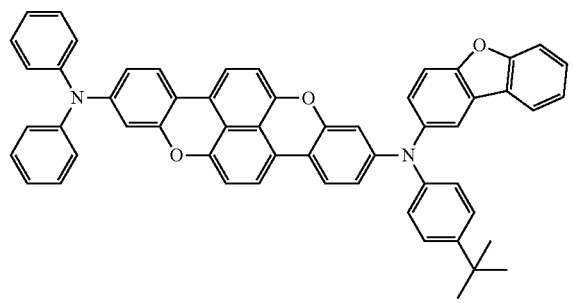
34
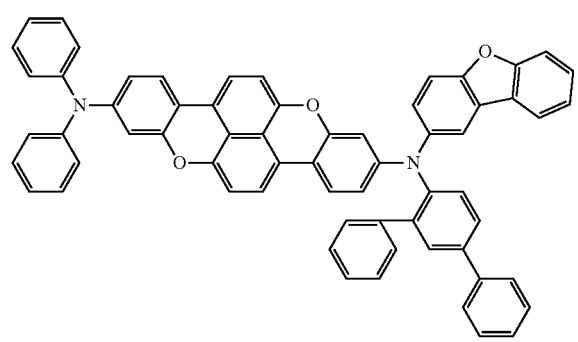
35
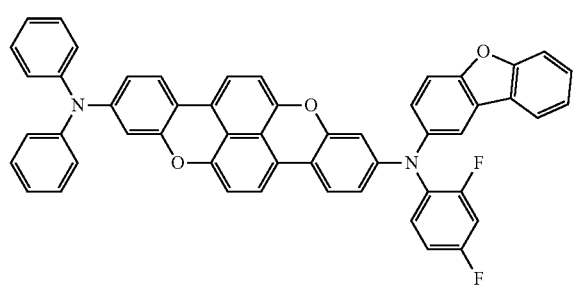
36
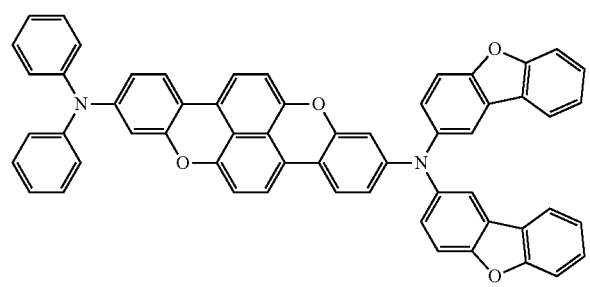
37
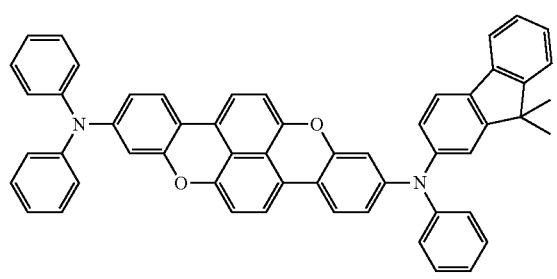

-continued
38
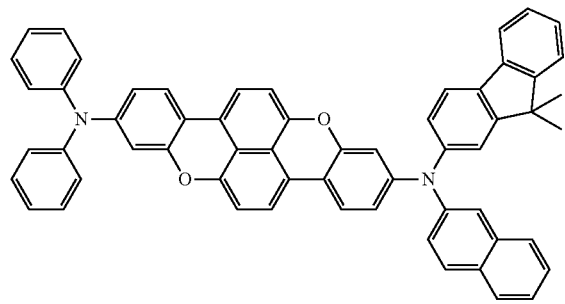
39
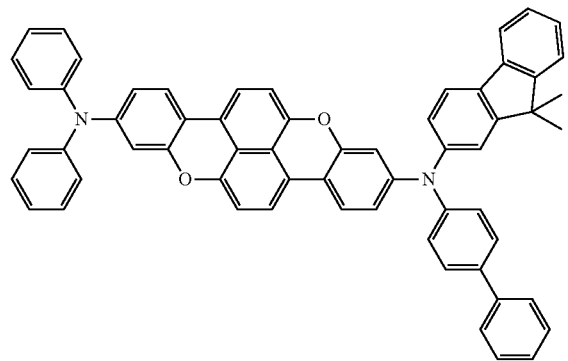
40
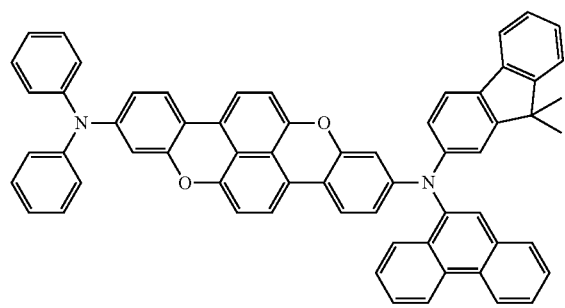
41
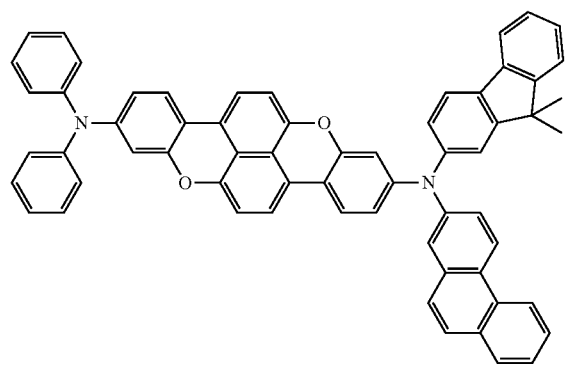
42
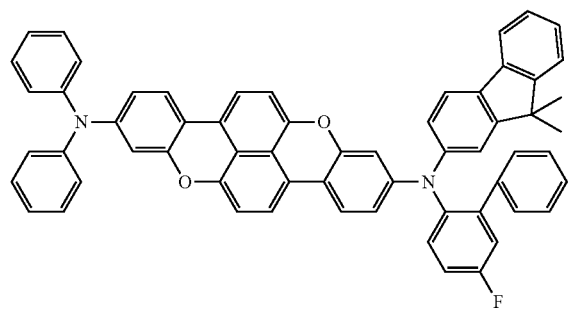
43
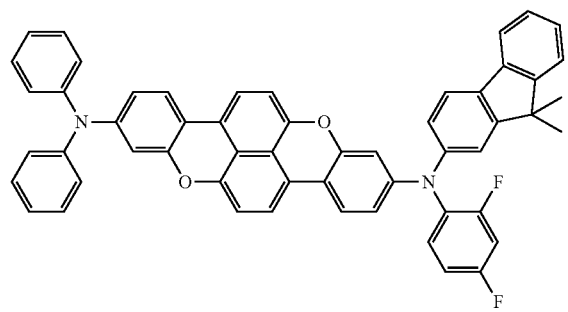
44
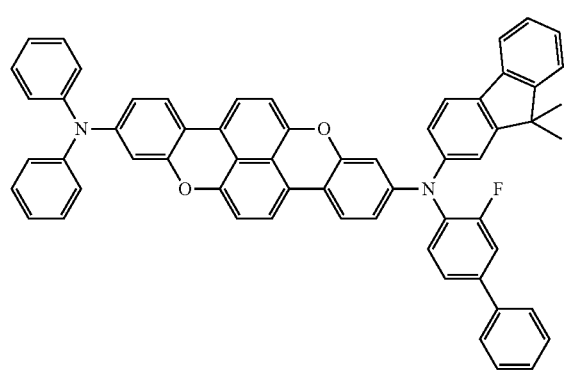
45
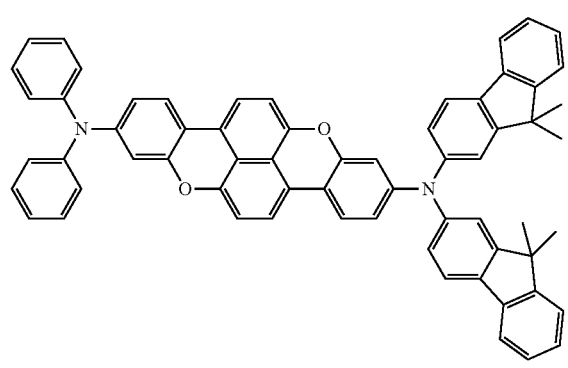

-continued
46
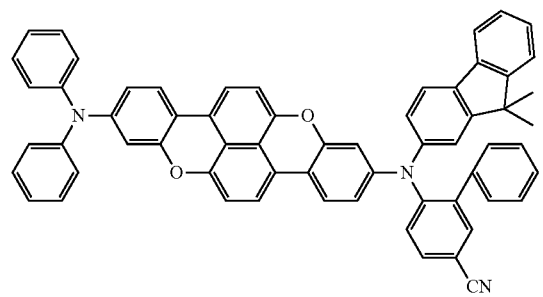
47
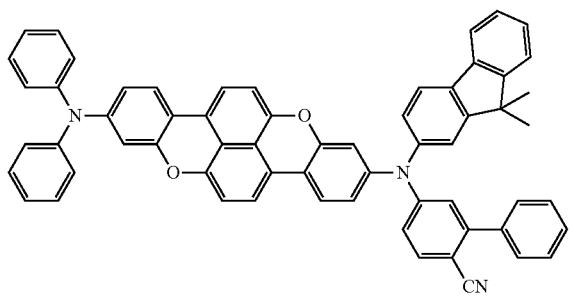
48
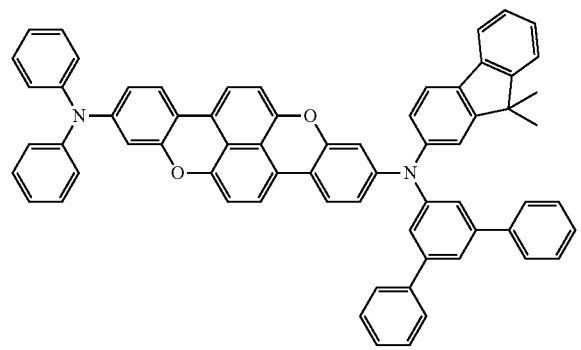
49
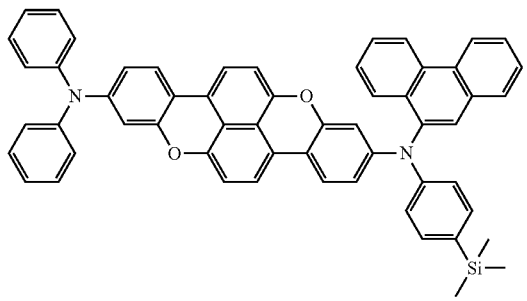
50
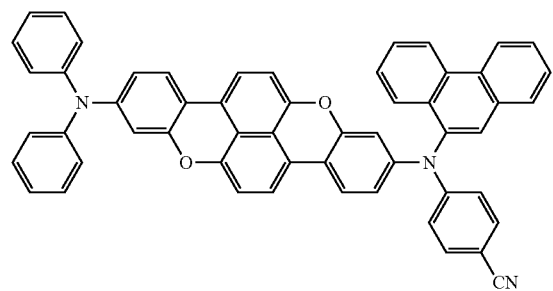
51
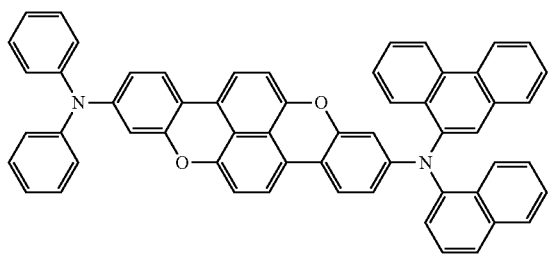
52
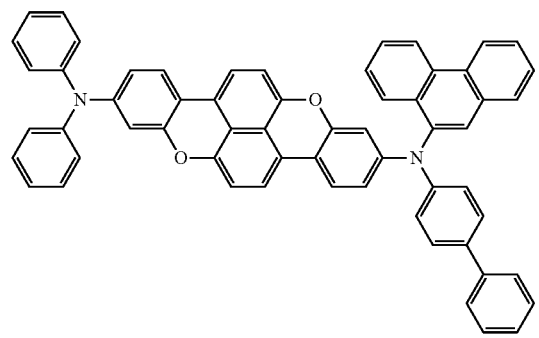
53
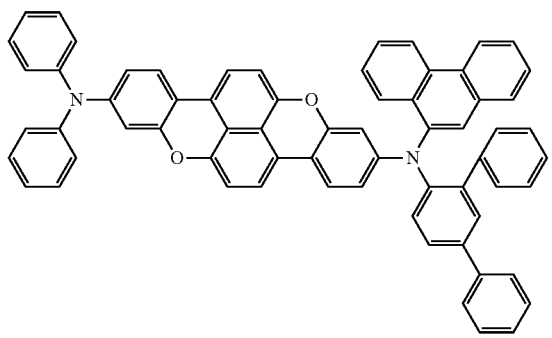

-continued
54
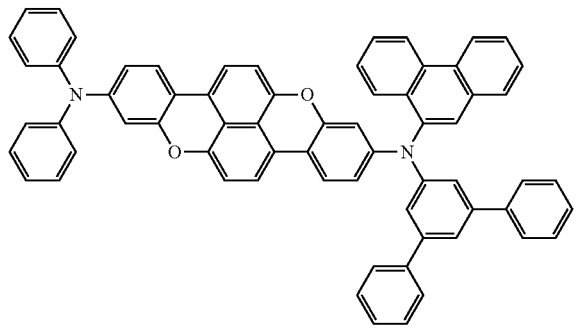
55
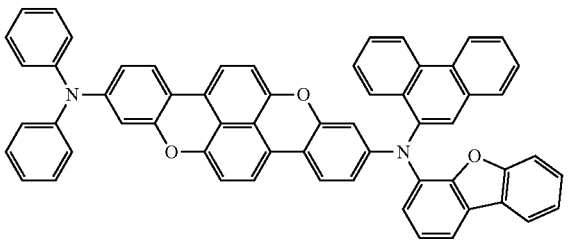
56
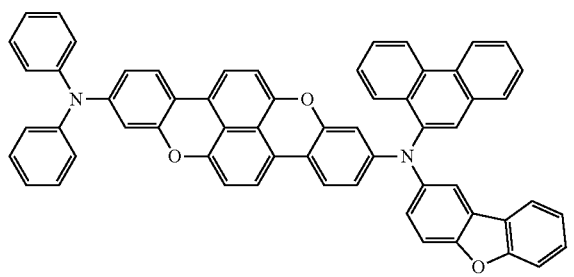
57
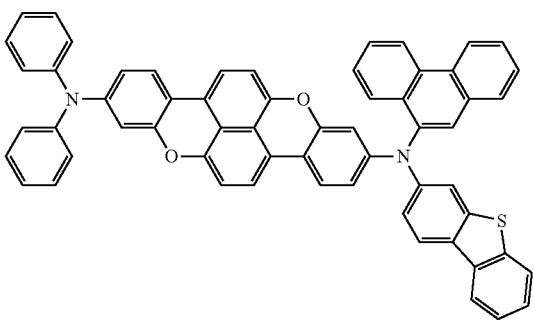
58
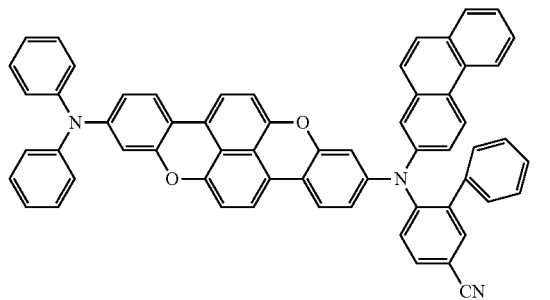
59
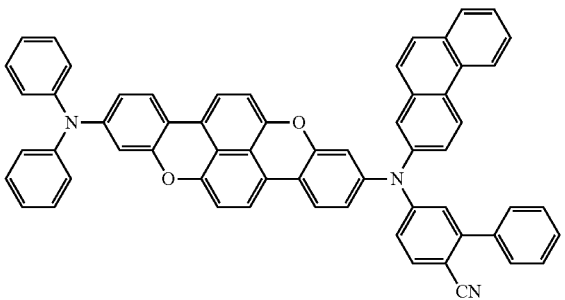
60
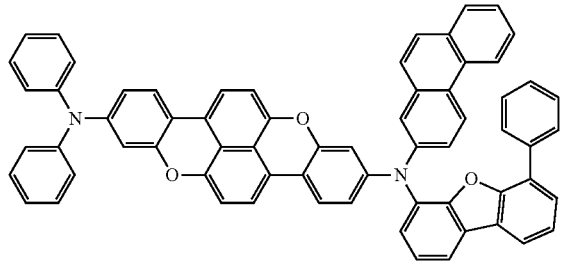
61
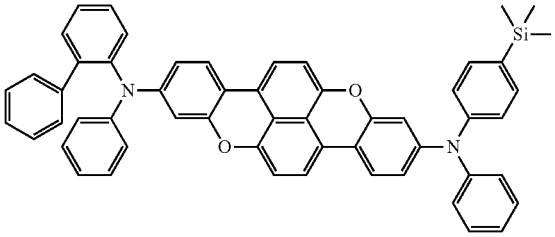
62
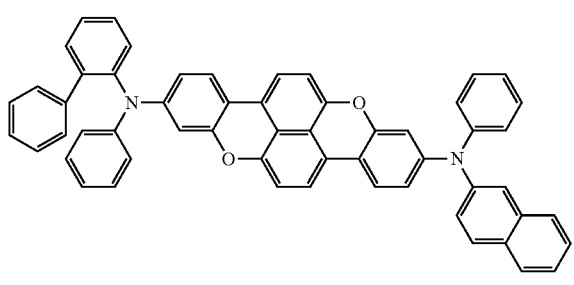
63
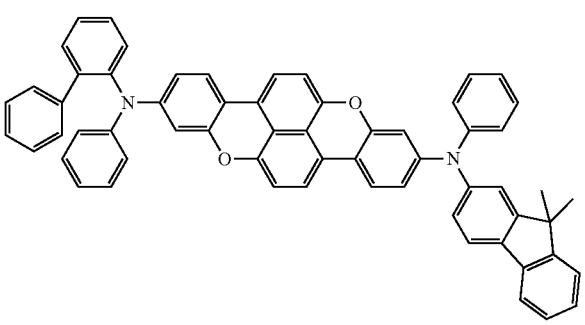

-continued
64
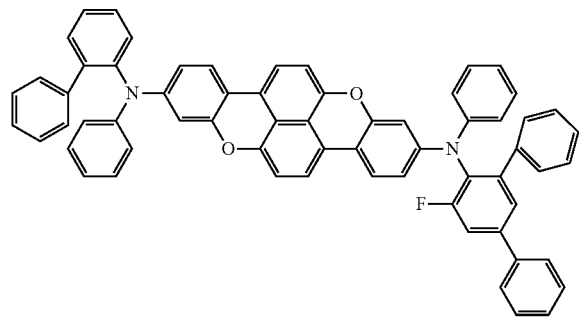
65
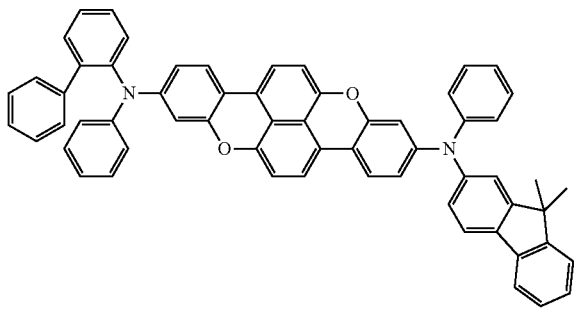
66
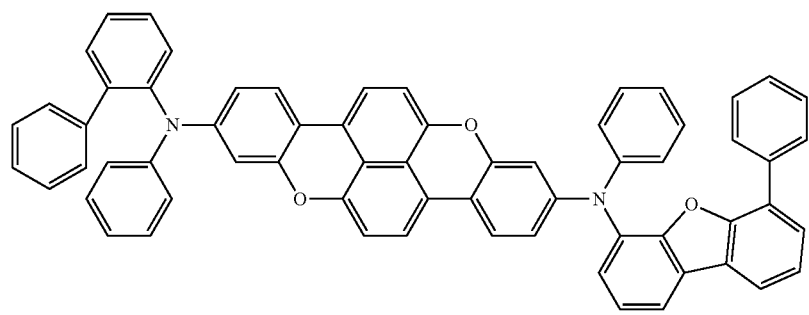
67
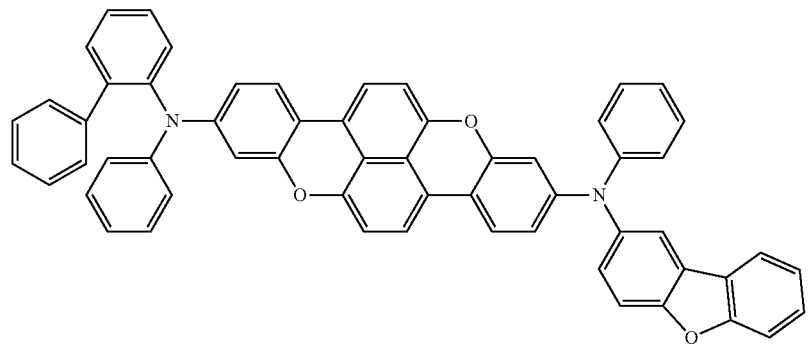
68
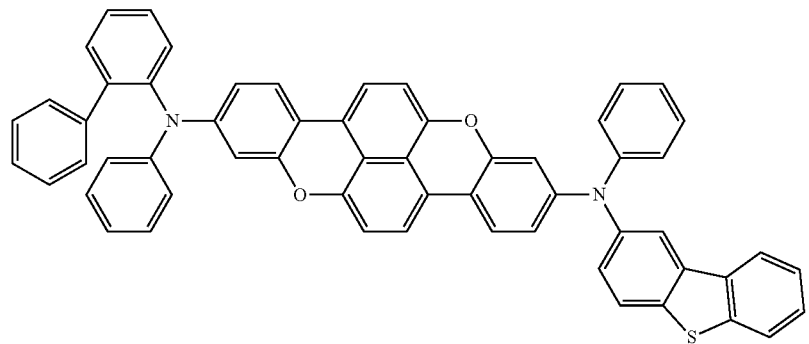

-continued
69
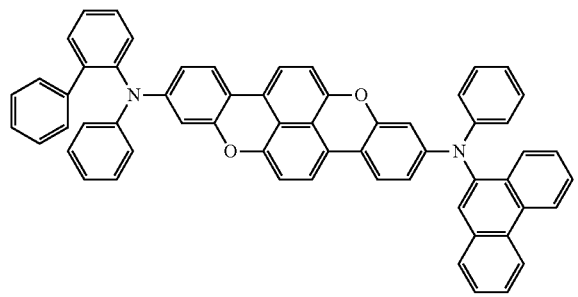
70
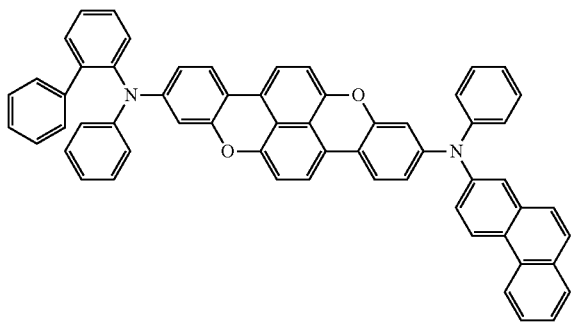
71
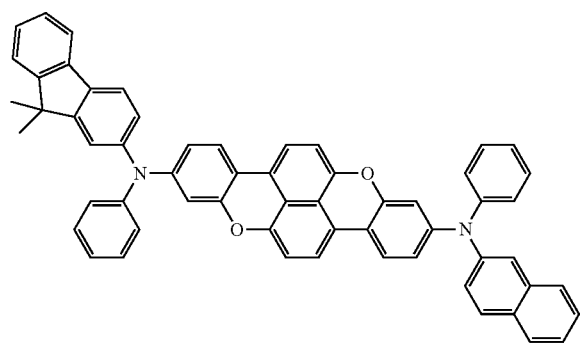
72
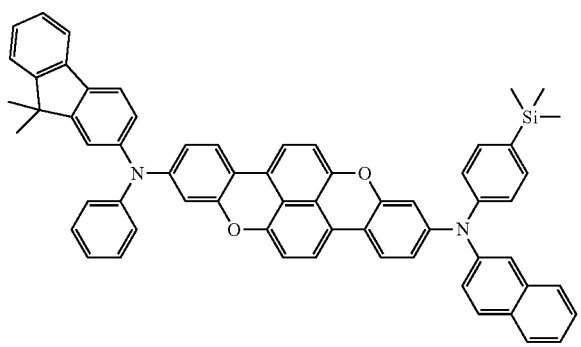
73
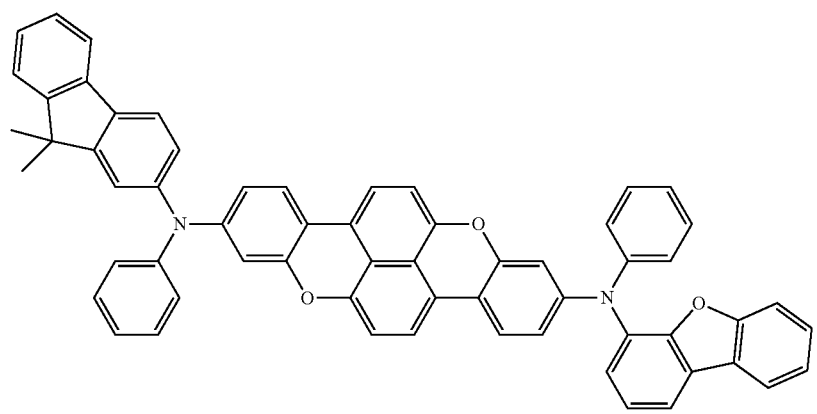
74
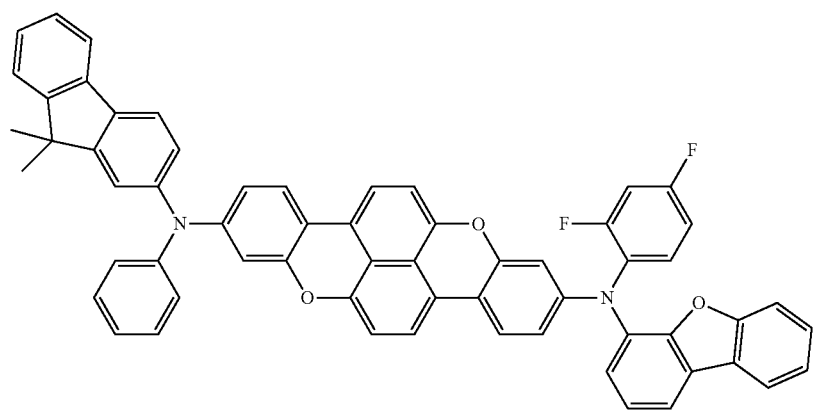

75
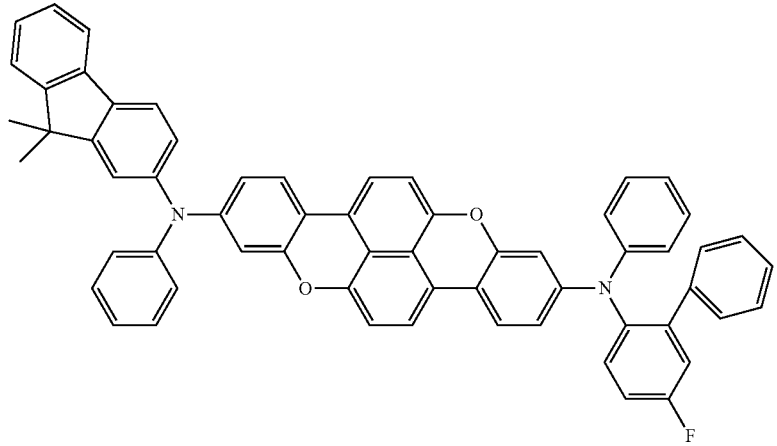
76
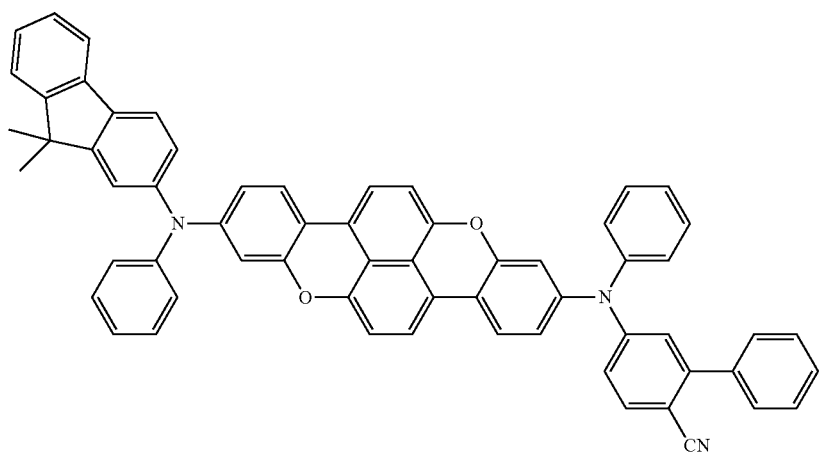
77
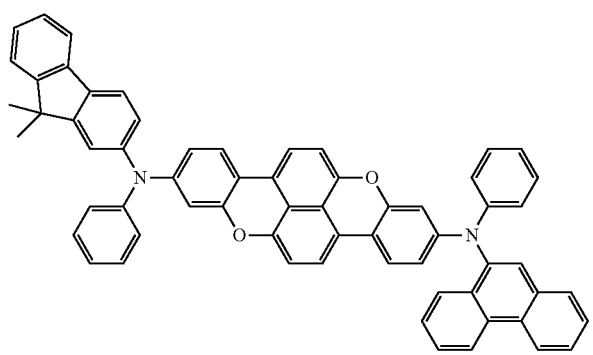
78
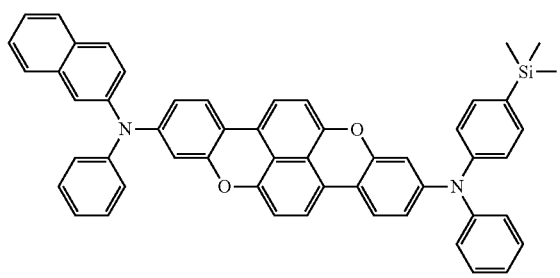
79
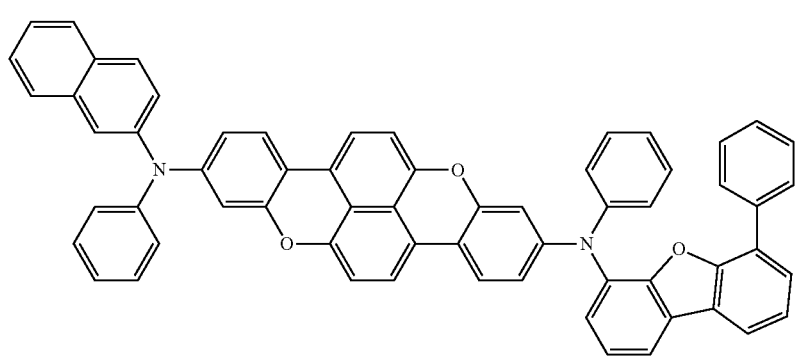

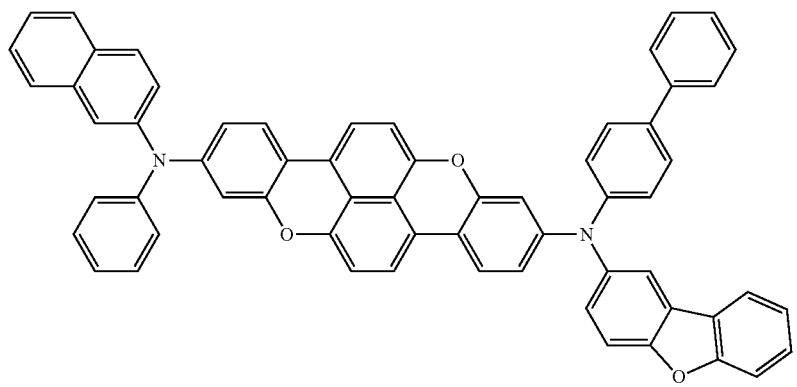
80
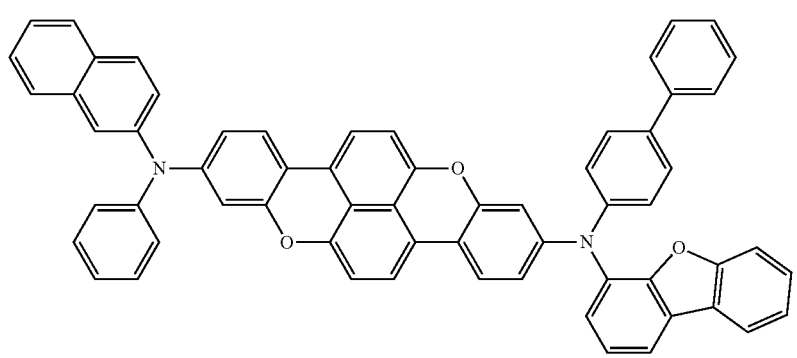
81
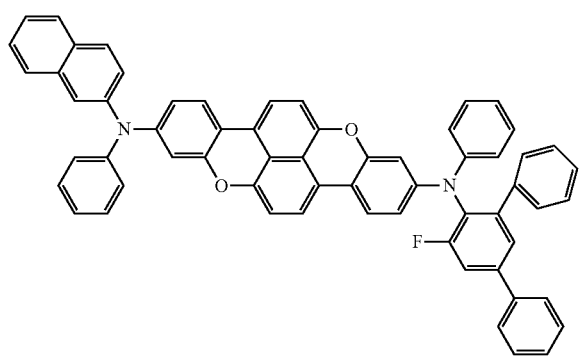
82
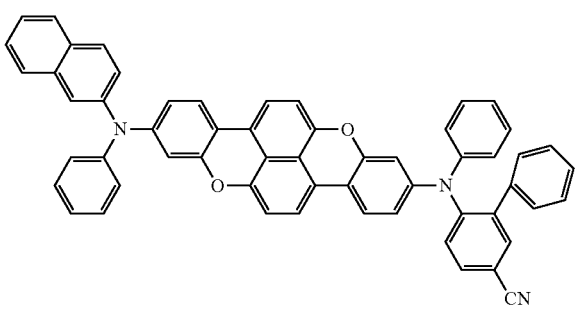
83
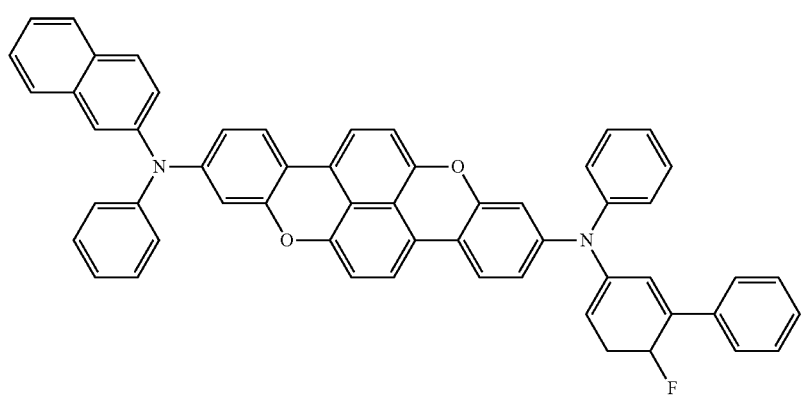
84

-continued
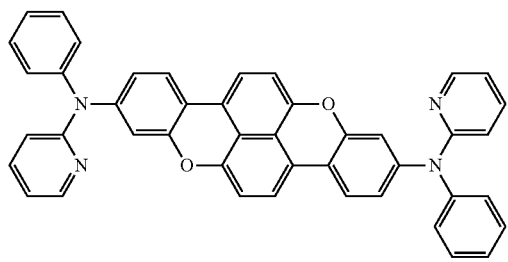
85
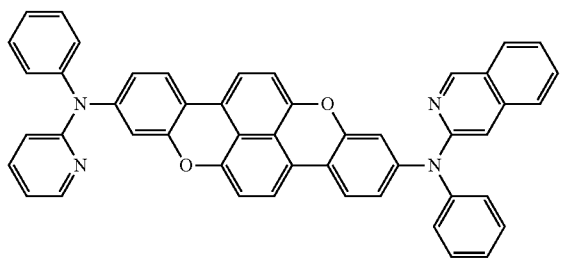
86
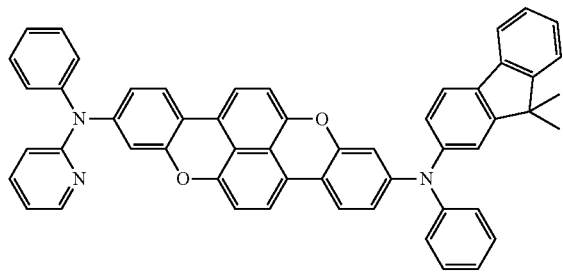
87
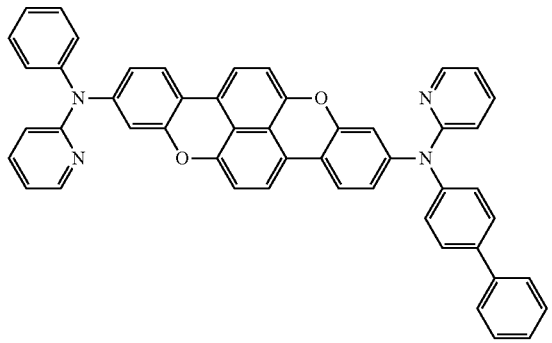
88
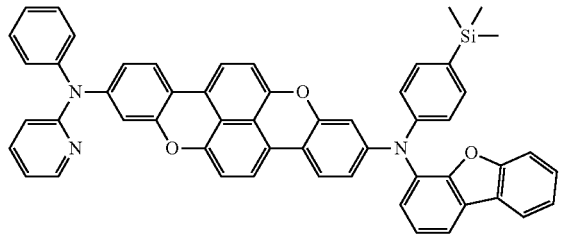
89
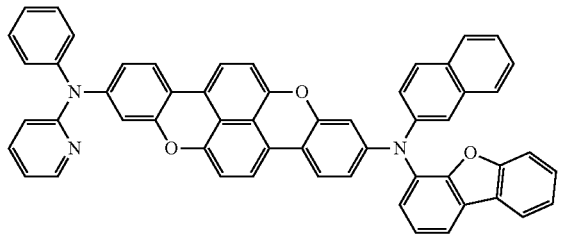
90
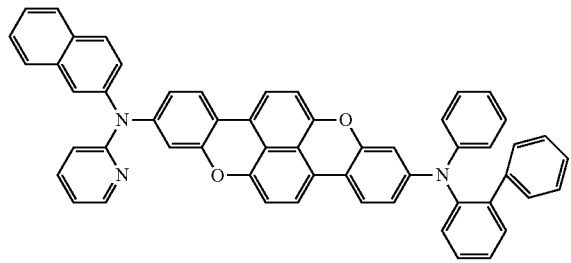
91
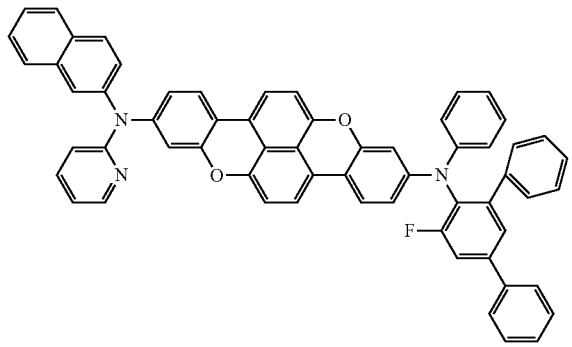
92
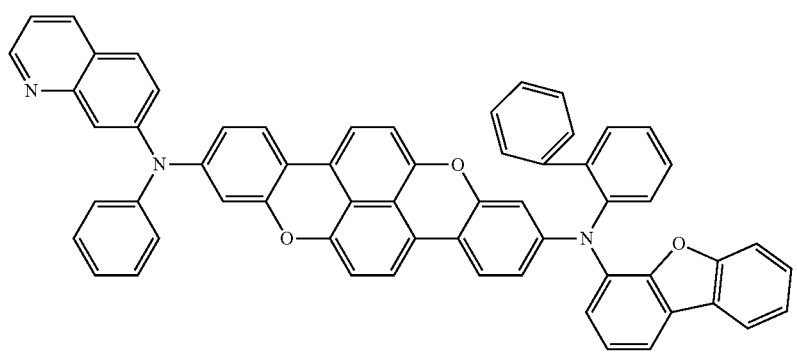
93

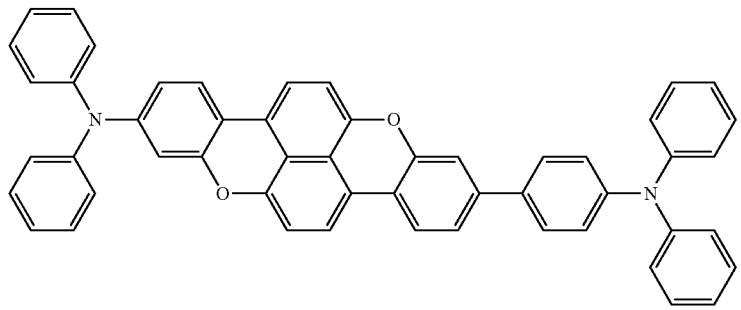

94

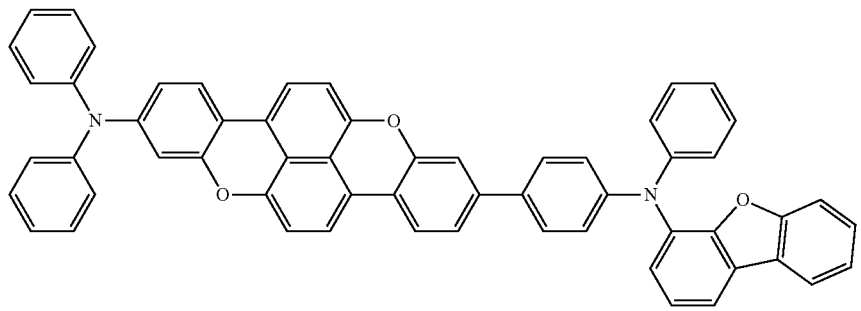

95

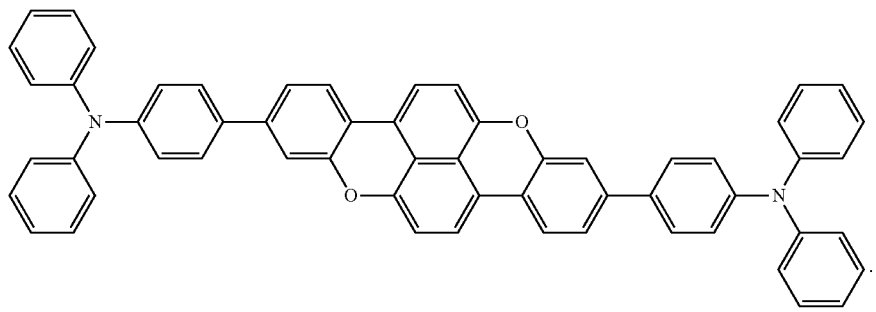

96

15. An organic light-emitting device, comprising:
a first electrode;
a second electrode opposite to the first electrode; and
an organic layer between the first electrode and the second electrode, the organic layer including an emission layer, wherein the organic layer includes at least one condensed cyclic compound as claimed in claim 1.

16. The organic light-emitting device as claimed in claim 15, wherein the organic layer includes:
a hole transport region between the first electrode and the emission layer, the hole transport region including at least one of a hole injection layer, a hole transport layer, a buffer layer, and an electron blocking layer, and
an electron transport region between the emission layer and the second electrode, the electron transport region including at least one of a hole blocking layer, an electron transport layer, and an electron injection layer.

17. The organic light-emitting device as claimed in claim 16, wherein the emission layer includes the at least one condensed cyclic compound.

18. The organic light-emitting device as claimed in claim 17, wherein:
the emission layer further includes a host,
the at least condensed cyclic compound is a dopant, and the host includes a compound represented by Formula 301A:

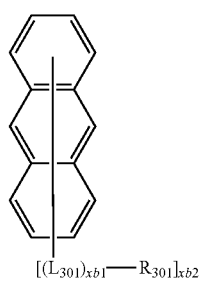

<Formula 301A> wherein, in Formula 301A,
$L_{301}$ is:
a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, or a chrysenylene group; or
a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, or a chrysenylene group, each substituted with a deuterium, —F, —Cl, —Br, —I, a hydroxyl group, a cyano group, a nitro group, an amino group, an amidino group, a hydrazine group, a hydrazone group, a carxb1 iso, 1, 2, or 3, and xb2 is 1, 2, 3, or 4.

19. The organic light-emitting device as claimed in claim 16, wherein the hole transport region includes at least one of a compound represented by Formula 201A and a compound represented by Formula 202A:

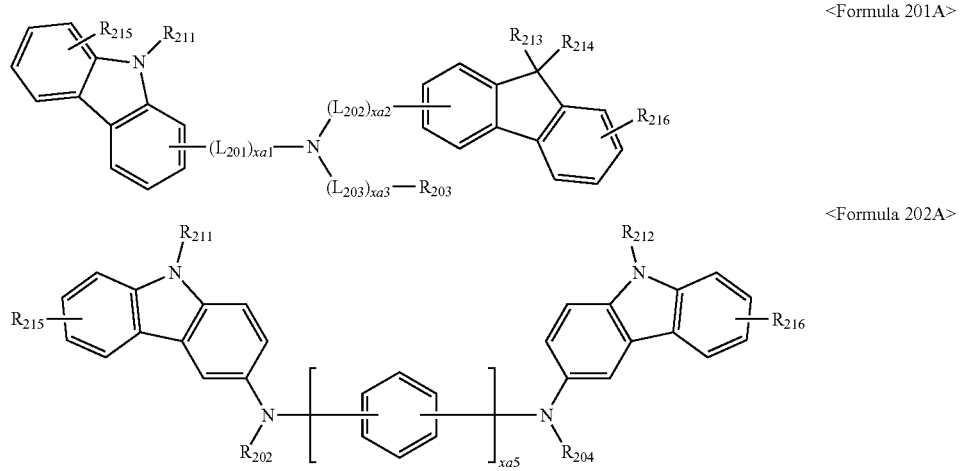

<Formula 201A>

<Formula 202A> boxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, or a chrysenyl group, $R_{301}$ is:

a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, or a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, or a chrysenyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, or a chrysenyl group, each substituted with a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, or a chrysenyl group, wherein, in Formulae 201A and 202A, $L_{201}$ to $L_{203}$ are each independently:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, or a triazinylene group; or a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, or a triazinylene group, each substituted with a deuterium, —F, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, xa1 to xa3 are each independently 0 or 1, $R_{203}$, $R_{211}$, and $R_{212}$ are each independently:
- a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or
- a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, each substituted with a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, $R_{213}$ and $R_{214}$ are each independently:
- a $C_1$-$C_{20}$ alkyl group or a $C_1$-$C_{20}$ alkoxy group;
- a $C_1$-$C_{20}$ alkyl group or a $C_1$-$C_{20}$ alkoxy group, each substituted with a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group,
- a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or
- a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, each substituted with a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, $R_{215}$ and $R_{216}$ are each independently:
- a hydrogen, a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, or a $C_1$-$C_{20}$ alkoxy group;
- a $C_1$-$C_{20}$ alkyl group or a $C_1$-$C_{20}$ alkoxy group, each substituted with a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group;
- a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or
- a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, each substituted with a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, and xa5 is 1 or 2.

20. The organic light-emitting device as claimed in claim 16, wherein the electron transport layer includes at least one of a compound represented by Formula 601 and a compound represented by Formula 602:

$$Ar_{601}\text{---}[(L_{601xe}\text{---}E_{601}]_{xe2}$$ <Formula 601>

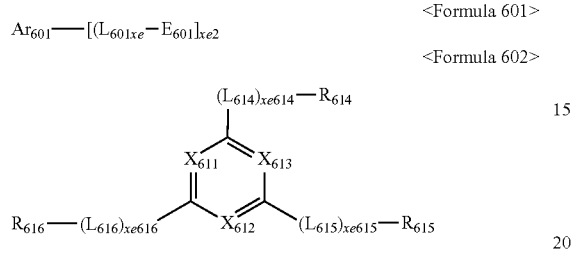

<Formula 602> wherein, in Formulae 601 and 602, $Ar_{601}$ is:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, or a chrysenylene group; or a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, or a chrysenylene group, each substituted with a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, or a chrysenyl group, $L_{611}$ to $L_{616}$ are each independently:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, or a triazinylene group; or a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, or a triazinylene group, each substituted with a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, $E_{601}$ is:

a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, or a dibenzocarbazolyl group; or a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, or a dibenzocarbazolyl group, each substituted with a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an obarenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, or a dibenzocarbazolyl group, xe1 is 0, 1, 2, or 3,
xe2 is 1, 2, 3, or 4,
$X_{611}$ is N or C-$(L_{611})_{xe611}$-$R_{611}$,
$X_{612}$ is N or C-$(L_{612})_{xe612}$-$R_{612}$,
$X_{613}$ is N or C-$(L_{613})_{xe613}$-$R_{613}$, at least one of $X_{611}$ to $X_{613}$ being N,
$R_{611}$ to $R_{616}$ are each independently:
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, each substituted with a deuterium, —F, —Cl, —Br, —I, a hydroxyl group, a cyano group, a nitro group, an amino group, an amidino group, a hydrazine group, a hydrazone group, a carboxylic group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, and
xe611 to xe616 are each independently 0, 1, 2, or 3.

\* \* \* \* \*